(12) United States Patent
Mellen et al.

(10) Patent No.: US 12,125,260 B2
(45) Date of Patent: *Oct. 22, 2024

(54) SYSTEMS AND METHODS FOR IDENTIFYING MORPHOLOGICAL PATTERNS IN TISSUE SAMPLES

(71) Applicant: 10X Genomics, Inc., Pleasanton, CA (US)

(72) Inventors: Jeffrey Clark Mellen, Martinez, CA (US); Jasper Staab, Honolulu, HI (US); Kevin J. Wu, San Francisco, CA (US); Neil Ira Weisenfeld, Lynnfield, MA (US); Florian Baumgartner, Stockholm (SE); Brynn Claypoole, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,963

(22) Filed: Jul. 20, 2023

(65) Prior Publication Data
US 2023/0394790 A1    Dec. 7, 2023

Related U.S. Application Data

(63) Continuation of application No. 18/047,620, filed on Oct. 18, 2022, now Pat. No. 11,756,286, which is a
(Continued)

(51) Int. Cl.
*G06V 10/762* (2022.01)
*G01N 1/30* (2006.01)
(Continued)

(52) U.S. Cl.
CPC .......... *G06V 10/762* (2022.01); *G01N 1/30* (2013.01); *G06T 7/0012* (2013.01); *G16B 15/00* (2019.02);
(Continued)

(58) Field of Classification Search
None
See application file for complete search history.

(56) References Cited

U.S. PATENT DOCUMENTS 5,231,580 A * 7/1993 Cheung ............... G06T 7/60
382/128
5,472,881 A    12/1995 Beebe et al.
(Continued)

FOREIGN PATENT DOCUMENTS

EP        1336662 A2    8/2003
WO    WO 2000/063437 A2    10/2000
(Continued)

OTHER PUBLICATIONS

10X Genomics, 2019, "Chromium Next GEM Single Cell 3' Reagent Kits v3.1 User Guide", Document No. CG000204, Rev D.
(Continued)

*Primary Examiner* — Tsung Yin Tsai

(57) ABSTRACT

A discrete attribute value dataset is obtained that is associated with a plurality of probe spots each assigned a different probe spot barcode. The dataset comprises spatial projections, each comprising images of a biological sample. Each image includes a corresponding plurality of discrete attribute values for the probe spots. Each such value is associated with a probe spot in the plurality of probes spots based on the probe spot barcodes. The dataset is clustered using the discrete attribute values, or dimension reduction components thereof, for a plurality of loci at each respective probe spot across the images of the projections thereby assigning each probe spot to a cluster in a plurality of clusters. Morphological patterns are identified from the spatial arrangement of the probe spots in the various clusters.

40 Claims, 38 Drawing Sheets
(24 of 38 Drawing Sheet(s) Filed in Color)

Related U.S. Application Data continuation of application No. 17/039,935, filed on Sep. 30, 2020, now Pat. No. 11,514,575.

(60) Provisional application No. 63/041,823, filed on Jun. 20, 2020, provisional application No. 62/980,077, filed on Feb. 21, 2020, provisional application No. 62/909,071, filed on Oct. 1, 2019.

(51) Int. Cl.
*G06T 7/00* (2017.01)
*G16B 15/00* (2019.01)

(52) U.S. Cl.
CPC .............. *G01N 2001/302* (2013.01); *G06T 2207/30024* (2013.01)

(56) References Cited

U.S. PATENT DOCUMENTS

| | | | |
|---|---|---|---|
| 5,599,675 | A | 2/1997 | Brenner |
| 5,610,287 | A | 3/1997 | Nikiforov et al. |
| 5,750,341 | A | 5/1998 | Macevicz |
| 5,807,522 | A | 9/1998 | Brown et al. |
| 5,837,860 | A | 11/1998 | Anderson et al. |
| 6,172,218 | B1 | 1/2001 | Brenner |
| 6,185,320 | B1* | 2/2001 | Bick ............ G06T 7/187 382/209 |
| 6,210,891 | B1 | 4/2001 | Nyren et al. |
| 6,258,568 | B1 | 7/2001 | Nyren |
| 6,266,459 | B1 | 7/2001 | Walt et al. |
| 6,274,320 | B1 | 8/2001 | Rothberg et al. |
| 6,278,794 | B1 | 8/2001 | Parekh |
| 6,306,597 | B1 | 10/2001 | Macevicz |
| 6,355,431 | B1 | 3/2002 | Chee et al. |
| 6,391,937 | B1 | 5/2002 | Beuhler et al. |
| 6,430,430 | B1* | 8/2002 | Gosche ............ G06T 7/155 128/923 |
| 6,737,236 | B1 | 5/2004 | Pieken et al. |
| 6,770,441 | B2 | 8/2004 | Dickinson |
| 6,859,570 | B2 | 2/2005 | Walt et al. |
| 6,969,488 | B2 | 11/2005 | Bridham et al. |
| 7,001,792 | B2 | 2/2006 | Sauer et al. |
| 7,057,026 | B2 | 6/2006 | Barnes et al. |
| 7,259,258 | B2 | 8/2007 | Kozlov et al. |
| 7,375,234 | B2 | 5/2008 | Sharpless et al. |
| 7,427,678 | B2 | 9/2008 | Pieken et al. |
| 7,709,198 | B2 | 5/2010 | Luo et al. |
| 7,877,213 | B2 | 1/2011 | Ghosh |
| 8,460,865 | B2 | 6/2013 | Chee et al. |
| 8,604,182 | B2 | 12/2013 | Luo et al. |
| 8,774,494 | B2 | 7/2014 | Staker |
| 8,951,726 | B2 | 2/2015 | Luo et al. |
| 9,359,641 | B2 | 6/2016 | Staker |
| 9,512,422 | B2 | 12/2016 | Barnard et al. |
| 9,593,365 | B2 | 3/2017 | Frisen et al. |
| 9,727,810 | B2 | 8/2017 | Fodor et al. |
| 9,783,841 | B2 | 10/2017 | Nolan et al. |
| 9,889,422 | B2 | 2/2018 | Smith et al. |
| 10,002,316 | B2 | 6/2018 | Fodor et al. |
| 10,041,949 | B2 | 8/2018 | Bendall et al. |
| 10,059,990 | B2 | 8/2018 | Boyden et al. |
| 10,138,509 | B2 | 11/2018 | Church et al. |
| 10,179,932 | B2 | 1/2019 | Church et al. |
| 10,347,365 | B2 | 7/2019 | Wong et al. |
| 10,366,777 | B2 | 7/2019 | Kyriazopoulou-Panagiotopoulou et al. |
| 10,832,796 | B2 | 11/2020 | Hubbell |
| 2005/0100900 | A1 | 5/2005 | Kawashima et al. |
| 2006/0188901 | A1 | 8/2006 | Barnes et al. |
| 2006/0240439 | A1 | 10/2006 | Smith et al. |
| 2006/0281109 | A1 | 12/2006 | Ost et al. |
| 2007/0166705 | A1 | 7/2007 | Milton et al. |
| 2007/0174007 | A1 | 7/2007 | Ghosh et al. |
| 2008/0280773 | A1 | 11/2008 | Fedurco |
| 2009/0026082 | A1 | 1/2009 | Rothberg et al. |
| 2009/0127589 | A1 | 5/2009 | Rothberg et al. |
| 2010/0111396 | A1* | 5/2010 | Boucheron ............ G06F 18/29 382/133 |
| 2010/0137143 | A1 | 6/2010 | Rothberg et al. |
| 2010/0282617 | A1 | 11/2010 | Rothberg et al. |
| 2011/0059865 | A1 | 3/2011 | Smith et al. |
| 2011/0150313 | A1* | 6/2011 | Su ............ G06T 7/238 382/132 |
| 2012/0270305 | A1 | 10/2012 | Reed et al. |
| 2013/0225420 | A1* | 8/2013 | Albertson ............ C12Q 1/6886 506/9 |
| 2013/0260372 | A1 | 10/2013 | Buemann et al. |
| 2014/0079923 | A1 | 3/2014 | George et al. |
| 2014/0378345 | A1 | 12/2014 | Hindson et al. |
| 2015/0376609 | A1 | 12/2015 | Hindson et al. |
| 2016/0062098 | A1* | 3/2016 | Brown ............ G02B 21/0076 600/431 |
| 2017/0016053 | A1 | 1/2017 | Beechem et al. |
| 2017/0253918 | A1 | 9/2017 | Kphman |
| 2018/0052081 | A1 | 2/2018 | Kohman |
| 2018/0105808 | A1 | 4/2018 | Mikkelsen et al. |
| 2018/0156784 | A1 | 6/2018 | Usmani et al. |
| 2018/0245142 | A1 | 8/2018 | So et al. |
| 2019/0032121 | A1 | 1/2019 | Daugharthy et al. |
| 2019/0203275 | A1 | 7/2019 | Frisen et al. |
| 2021/0097684 | A1 | 4/2021 | Mellen et al. |
| 2021/0155982 | A1 | 5/2021 | Yin et al. |

FOREIGN PATENT DOCUMENTS

| | | |
|---|---|---|
| WO | WO 2005/036451 A1 | 4/2005 |
| WO | WO 2005/065814 A1 | 7/2005 |
| WO | WO 2006/064199 A1 | 6/2006 |
| WO | WO 2007/010251 A2 | 1/2007 |
| WO | WO 2011/094669 A1 | 8/2011 |
| WO | WO 2011/127099 A1 | 10/2011 |
| WO | WO 2012/140224 A1 | 10/2012 |
| WO | WO 2014/060483 A1 | 4/2014 |
| WO | WO 2014/163886 A1 | 10/2014 |
| WO | WO 2014/210225 A1 | 12/2014 |
| WO | WO 2014/210233 A1 | 12/2014 |
| WO | WO 2015/161173 A1 | 10/2015 |
| WO | WO 2016/007839 A1 | 1/2016 |
| WO | WO 2016/162309 A1 | 10/2016 |
| WO | WO 2016/166128 A1 | 10/2016 |
| WO | WO 2017/019456 A2 | 2/2017 |
| WO | WO 2017/027368 A1 | 2/2017 |
| WO | WO 2017/144338 A1 | 8/2017 |
| WO | WO 2017/222453 A1 | 12/2017 |
| WO | WO 2018/045181 A1 | 3/2018 |
| WO | WO 2018/045186 A1 | 3/2018 |
| WO | WO 2018/057999 A1 | 3/2018 |
| WO | WO 2018/075693 A1 | 4/2018 |
| WO | WO 2018/091676 A1 | 5/2018 |
| WO | WO 2018/107054 A1 | 6/2018 |
| WO | WO 2018/136856 A1 | 7/2018 |
| WO | WO 2019/068880 A1 | 4/2019 |
| WO | WO 2019/075091 A1 | 4/2019 |
| WO | WO 2019/113533 A1 | 6/2019 |
| WO | WO 2020/123316 A2 | 6/2020 |

OTHER PUBLICATIONS

10X Genomics, 2017, "Chromium Single Cell 3' Reagent Kits v2 User Guide," Document No. CG00052 Rev B.

10X Genomics, 2020, "Chromium Single Cell V(D)J Reagents Kits User Guide," Document No. CG000086, Rev M.

10X Genomics, 2019, "Visium Spatial Gene Expression Solution," LIT000054 Rev C Visium Spatial Gene Expression Product Flyer.

10X Genomics, "What is the difference between Single Cell 3' and 5' Gene Expression libraries?", downloaded from the Internet on Jan. 21, 2021.

Beattie et al., "Advances in Genosensor Research", (1995) Clin. Chem. 45, 700-706.

(56) References Cited

OTHER PUBLICATIONS

Beier et al., "Versatile derivatisation of solid support media for covalent bonding on DNA-microchips", (1999) Nucleic Acids Research 27, 1970-1977.
Canzar and Stazberg, 2018, "Short Read Mapping: An Algorithmic Tour," Proc IEEE Inst. Electr Electron Eng., 105(3), 436-458.
Carter et al., "Stabilization of an optical microscope to 0.1 nm in three dimensions", Applied Optics 46:421-427, 2007. $35.
Chen et al., "RNA imaging. Spatially resolved, highly multiplexed RNA profiling in single cells", Science 348(6233):aaa6090, 2015.
Chen et al., "Nanoscale imaging of RNA with expansion microscopy", Nat. Methods 13:679-684, 2016.
Chrisey et al., "Covalent attachment of synthetic DNA to self-assembled monolayer films", (1996) Nucleic Acid Research 24, 3031-3039.
Cockroft et al., "A Single-Molecule Nanopore Device Detects DNA Polymerase Activity With Single-Nucleotide Resolution", J. Am. Chem. Soc. 130, 818-820 (2008).
Deamer et al., "Nanopores and nucleic acids: prospects for ultrarapid sequencing", Trends Biotechnol. 18, 147-151 (2000) $35.95.
Deamer et al., "Characterization of nucleic acids by nanopore analysis", Acc. Chem. Res. 35:817-825 (2002) $40.
Eagen, "Principles of Chromosome Architecture Revealed by Hi-C", Trends Biochem. Sci. (2018) 43(6): 469-478.
Fahy et al. "Design and synthesis of polyacrylamide-based oligonucleotide supports for use in nucleic acid diagnostics", (1993) Nucleic Acid Research 21, 1819-1826.
Gao et al., "Q&A: Expansion microscopy", BMC Biol. 15:50, 2017.
Gunderson et al., "Decoding randomly ordered DNA arrays", Genome Research 14:870-877 (2004).
Guo et al. "Direct fluorescence analysis of genetic polymorphisms by hybridization with oligonucleotide arrays on glass supports ", (1994) Nucleic Acid Research 22, 5456-5465.
Gupta et al., "Single-cell isoform RNA sequencing characterizes isoforms in thousands of cerebellar cells", Nature Biotechnol. 36:1197-1202, 2018.
Huang and Miller, "A Time-Efficient, Linear-Space Local Similarity Algorithm", Adv. Appl. Math, 12:337-57 (1991).
Jamur et al., "Permeabilization of cell membranes", Method Mol. Biol. 588:63-66, 2010.
Joos et al., "Covalent attachment of hybridizable oligonucleotides to glass supports", (1997) Analitical Biochemistry 247, 96-101. $35.95.
Koch et al., "Photochemical immobilization of anthraquinone conjugated oligonucleotides and PCR amplicons on solid surfaces", (2000) Bioconjugate Chem. 11, 474-483. $40.
Korlach et al., "Selective aluminum passivation for targeted immobilization of single DNA polymerase molecules in zero-mode waveguide nanostructures", Proc. Natl. Acad. Sci. USA (2008), 105, 1176-1181.
Lamture et al., "Direct detection of nucleic acid hybridization on the surface of a charge coupled device", (1994) Nucleic Acids Research 22, 2121-2125.
Lee et al., "Highly multiplexed subcellular RNA sequencing in situ" (2014) Science, 343(6177), 1360-1363.
Lee et al., "Fluorescent in situ sequencing (FISSEQ) of RNA for gene expression profiling in intact cells and tissues", Nat. Protoc. 10(3):442-458, 2015.
Levene et al., "Zero-mode waveguides for single-molecule analysis at high concentrations", Science (2003), 299, 682-686.
Li et al., "DNA molecules and configurations in a solid-state nanopore microscope", Nat. Mater. 2:611-615 (2003).
Liu et al., "Surface and interface control on photochemically initiated immobilization", (2006) Journal of the American Chemical Society 128, 14067-14072.
Lundquist et al., "Parallel confocal detection of single molecules in real time", Opt. Lett. (2008), vol. 33, No. 9, 1026-1028.
Ma B. et al., "PathHunter: faster and more sensitive homology search", Bioinformatics, Mar. 2002, vol. 18, Issue 3, pp. 440-445.

Macosko et al., "Highly Parallel Genome-wide Expression Profiling of Individual Cells Using Nanoliter Droplets", (2015) Cell 161, 1202-1214.
Miele et al., "Mapping cis- and trans-chromatin interaction networks using Chromosome Conformation Capture (3C)", Methods Mol Biol. (2009), 464.
Miller et al., "Basic concepts of microarrays and potential applications in clinical microbiology." Clinical microbiology reviews 22.4 (2009): 611-633.
Mitra et al., "Fluorescent in situ sequencing on polymerase colonies", (2003) Anal. Biochem., 320, 55-65.
Moffitt, "RNA Imaging with Multiplexed Error-Robust Fluorescence In Situ Hybridization (MERFISH)", (2016) Methods in Enzymology, 572, 1-49.
Nikforov et al., "The use of 96-well polystyrene plates for DNA hybridization-based assays: an evaluation of different approaches to oligonucleotide immobilization ", (1995) Analytical Biochemistry 227, 201-209.
Petti et al., "A general approach for detecting expressed mutations in AML cells using single cell RNA-sequencing", Nature Communications, (2019) 10:3660.
Raab et al., "Human tRNA genes function as chromatin insulators", Embo. J. (2012), 31(2): 330-350.
Rao, N. "Discover the genes that matter while preserving spatial information: The Visium Gene Expression Solution", Webinar presented at Cell Biology 2019 Sep. 26, 2019 (Sep. 26, 2019), p. 1 pp., Retrieved from the Internet: URL:https://www.labroots.com/webinar/discover-genes-matter-preserving-spatial-information-visium-gene-expression-solution XP054981474.
Rao, N. et al., "Envision New Dimensions Introducing the Visium Spatial Gene Expression Solution", Sep. 19, 2019 (Sep. 19, 2019), Retrieved from the Internet: https://10xgenomics.com/videos/seminars/introducing-the-visium-spatial-gene-expression-solution/ XP055756016 [retrieved on Aug. 5, 2022].
Rodrigues et al., "Slide-seq: A scalable technology for measuring genome-wide expression at high spatial resolution", Science 363(6434):1463-1467, 2019.
Rogers et al., "Use of a novel cross-linking method to modify adenovirus tropism", (1997) Gene Therapy 4, 1387-1392.
Rogers et al., "Immobilization of Oligonucleotides onto a Glass Support via Disulfide Bonds: A Method for Preparation of DNA Microarrays", (1999) Analytical Biochemistry 266, 23-30.
Ronaghi et al., "A sequencing method based on real-time pyrophosphate", Science 281 (5375), 363 (1998).
Ronaghi, "Pyrosequencing sheds light on DNA sequencing", Genome Res. 11(1), 3-11 (2001).
Ronaghi et al., "Real-time DNA sequencing using detection of pyrophosphate release", Anal. Biochem. 242(1), 84-9 (1996).
Running and Urdea, "A procedure for productive coupling of synthetic oligonucleotides to polystyrene microtiter wells for hybridization capture", (1990) BioTechnique 8, 276-279.
Shalon et al., "A DNA microarray system for analyzing complex DNA samples using two-color fluorescent probe hybridization", (1996) Genome Research, 639-645.
Shendure et al., "Accurate Multiplex Polony Sequencing of an Evolved Bacterial Genome", Science (2005), 309: 1728-1732.
Simonis et al., "Nuclear organization of active and inactive chromatin domains uncovered by chromosome conformation capture-on-chip (4C)", Nat. Genet. (2006), 38(11): 1348-1354.
Smith and Waterman, "Identification of Common Molecular Subsequences", J Mol. Biol., 147(1):195-97 (1981).
Söderberg et al., "Characterizing proteins and their interactions in cells and tissues using the in situ proximity ligation assay", Methods. (2008), 45(3): 227-32.
Soni et al., "Progress toward Ultrafast DNA Sequencing Using Solid-State Nanopores", Clin. Chem. 53, 1996-2001 (2007).
Stimpson et al., "Real-time detection of DNA hybridization and melting on oligonucleotide arrays by using optical wave guides", (1995) Proc. Natl. Acad. Sci. USA 92, 6379-6383.
Timofeev et al., "Regioselective immobilization of short oligonucleotides to acrylic copolymer gels", (1996) Nucleic Acids Research 24, 3142-3148.

(56) References Cited

OTHER PUBLICATIONS

Trejo et al., "Extraction-free whole transcriptome gene expression analysis of FFPE sections and histology-directed subareas of tissue", PLoS ONE 14(2):e0212031, 2019.

Uchida, 2013, "Image processing and recognition for biological images," Develop. Growth Differ. 55, 523-549, doi:10.1111/dgd.12054.

U.S. Appl. No. 62/979,889, entitled "Capturing Targeted Genetic Targets Using a Hybridization/Capture Approach," Feb. 21, 2020.

U.S. Appl. No. 63/022,988, entitled "Systems and Methods for Index Hopping Filtering," filed Feb. 4, 2020.

U.S. Appl. No. 63/041,823, entitled "Systems and Methods for Identifying Morphological Patterns in Tissue Samples," filed Jun. 20, 2020.

U.S. Appl. No. 63/041,825, entitled "Pipeline for Spatial Analysis of Analytes," filed Jun. 20, 2020.

Wang, C., "Integrative Analysis of Multi-Modality Data in Cancer", Jan. 1, 2015 (Jan. 1, 2015), Retrieved from the Internet: URL:https://etd.ohiolink.edu/letd.send_file?accession=osu1429791373&disposition=inline XP055355084.

Wang et al., "Three-dimensional intact-tissue sequencing of single-cell transcriptional states", (2018) Science, 361(6499) 5691.

Zhang et al., "Single-base mutational analysis of cancer and genetic diseases using membrane bound modified oligonucleotides", (1991) Nucleic Acids Research, 19, 3929-3933.

\* cited by examiner

202 — A visualization system 100 comprising one or more processing cores, a persistent memory and a non-persistent memory. The persistent memory and the non-persistent memory collectively storing instructions for performing the following method.

204 — Obtain a discrete attribute value dataset associated with a plurality of probe spots having a spatial arrangement, wherein each probe spot in the plurality of probe spots is assigned a unique barcode in a plurality of barcodes and the plurality of probe spots comprises at least 1000 probe spots, the discrete attribute value dataset comprising: (i) one or more spatial projections of a biological sample, (ii) one or more two-dimensional images, for a spatial projection in the one or more spatial projections, each two-dimensional image in the one or more two-dimensional images (a) taken of a first tissue section, obtained from the biological sample, overlaid on a substrate having the plurality of probe spots arranged in the spatial arrangement and (b) comprising at least 100,000 pixel values.

205 — Each locus 122 in the plurality of loci is a respective gene in a plurality of genes. Each discrete attribute value 124 is a count of transcript reads within the probe spot that map to a respective gene in the plurality of genes.

206 — Obtaining a corresponding cluster assignment in a plurality of clusters, of each respective probe spot in the plurality of probe spots of the discrete attribute value dataset, wherein the corresponding cluster assignment is based, at least in part, on the corresponding plurality of discrete attribute values of the respective probe spot, or a corresponding plurality of dimension reduction components derived, at least in part, from the corresponding plurality of discrete attribute values of the respective probe spot

208 — The clustering the dataset is performed on a computer system remote from the visualization system prior to storing the dataset in persistent memory.

210 — The clustering the dataset comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm.

212 — The clustering the dataset comprises k-means clustering, a fuzzy k-means clustering algorithm, or Jarvis-Patrick clustering.

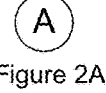

Figure 2A

SYSTEMS AND METHODS FOR IDENTIFYING MORPHOLOGICAL PATTERNS IN TISSUE SAMPLES

CROSS REFERENCE TO RELATED APPLICATIONS

This application is a continuation of U.S. patent application Ser. No. 18/047,620 filed Oct. 18, 2022, which is a continuation of U.S. patent application Ser. No. 17/039,935, filed Sep. 30, 2020, which claims priority to U.S. Provisional Patent Application No. 63/041,823, entitled "Systems and Methods for Identifying Morphological Patterns in Tissue Samples," filed Jun. 20, 2020, which is hereby incorporated by reference in its entirety. This application also claims priority to U.S. Provisional Patent Application No. 62/980,077, entitled "Systems and Methods for Visualizing a Pattern in a Dataset," filed Feb. 21, 2020, which is hereby incorporated by reference in its entirety. This application also claims priority to U.S. Provisional Patent Application No. 62/909,071, entitled "Systems and Methods for Visualizing a Pattern in a Dataset," filed Oct. 1, 2019, which is hereby incorporated by reference in its entirety.

TECHNICAL FIELD

This specification describes technologies relating to visualizing patterns in large, complex datasets, such as spatially arranged next generation sequencing data, and using the data to visualize patterns.

BACKGROUND

The relationship between cells and their relative locations within a tissue sample can be critical to understanding disease pathology. For example, such information can address questions regarding whether lymphocytes are successfully infiltrating a tumor or not, for example by identifying cell surface receptors associated with lymphocytes. In such a situation, lymphocyte infiltration would be associated with a favorable diagnosis whereas the inability of lymphocytes to infiltrate the tumor would be associated with an unfavorable diagnosis. Thus, the spatial relationship of cell types in heterogeneous tissue can be used to analyze tissue samples.

Spatial transcriptomics is a technology that allows scientists to measure gene activity in a tissue sample and map where the gene activity is occurring. Already this technology is leading to new discoveries that will prove instrumental in helping scientists gain a better understanding of biological processes and disease.

Spatial transcriptomics is made possible by advances in nucleic acid sequencing that have given rise to rich datasets for cell populations. Such sequencing techniques provide data for cell populations that can be used to determine genomic heterogeneity, including genomic copy number variation, as well as for mapping clonal evolution (e.g., evaluation of the evolution of tumors).

However, such sequencing datasets are complex and often large and the techniques used to localize gene expression to particular regions of a biological sample are labor intensive.

Consequently, there is a need for additional tools to enable a scalable approach to approaching spatial transcriptomics and spatial proteomics in a way that allows for the improved and less labor intensive analysis in order to determine genomic heterogeneity such as copy number variation, map clonal evolution, detect antigen receptors and/or identification of somatic variation in a morphological context.

SUMMARY

Technical solutions (e.g., computing systems, methods, and non-transitory computer readable storage mediums) for addressing the above-identified problems with discovery patterns in datasets are provided in the present disclosure. A tissue section (e.g., fresh-frozen tissue section) is imaged for histological purposes and placed on an array containing barcoded capture probes that bind to RNA. Tissue is fixed and permeabilized to release RNA to bind to adjacent capture probes, allowing for the capture of barcoded spatial gene expression information. Spatially barcoded cDNA is then synthesized from captured RNA and sequencing libraries prepared with the spatial barcodes intact. The libraries are then sequenced and data visualized to determine which genes are expressed, and where, as well as in what quantity. The present disclosure provides a number of tools for handling the vast amount of sequencing data such techniques produce and well as tools for identifying morphological patterns in the underlying tissue sample that are associated with specific biological conditions.

The following presents a summary of the present disclosure in order to provide a basic understanding of some of the aspects of the present disclosure. This summary is not an extensive overview of the present disclosure. It is not intended to identify key/critical elements of the present disclosure or to delineate the scope of the present disclosure. Its sole purpose is to present some of the concepts of the present disclosure in a simplified form as a prelude to the more detailed description that is presented later.

One aspect of the present disclosure provides a method for identifying a morphological pattern. The method comprises, at a computer system comprising one or more processing cores, a memory, and a display, obtaining a discrete attribute value dataset associated with a plurality of probe spots having a spatial arrangement. Each probe spot in the plurality of probe spots is assigned a unique barcode in a plurality of barcodes and the plurality of probe spots comprises at least 25, at least 50, at least 100, at least 150, at least 300, at least 400, or at 1000 probe spots. The discrete attribute value dataset comprises one or more spatial projections of a biological sample (e.g., tissue sample). The discrete attribute value dataset further comprises one or more two-dimensional images, for a first spatial projection in the one or more spatial projections. Each two-dimensional image in the one or more two-dimensional images is taken of a first tissue section, obtained from the biological sample, overlaid on a substrate (e.g., a slide, coverslip, semiconductor wafer, chip, etc.) having the plurality of probe spots arranged in the spatial arrangement. Also, each two-dimensional image in the one or more two-dimensional images comprises at least 100,000 pixel values. The discrete attribute value dataset further comprises a corresponding plurality of discrete attribute values for each respective probe spot in the plurality of probe spots obtained from spatial sequencing of the first tissue section. Each respective discrete attribute value in the corresponding plurality of discrete attribute values is for a different loci in a plurality of loci. Each such corresponding plurality of discrete attribute values comprises at least 500 discrete attribute values.

The method further comprises obtaining a corresponding cluster assignment in a plurality of clusters, of each respective probe spot in the plurality of probe spots of the discrete attribute value dataset. The corresponding cluster assignment is based, at least in part, on the corresponding plurality of discrete attribute values of the respective probe spot, or a corresponding plurality of dimension reduction components derived, at least in part, from the corresponding plurality of discrete attribute values of the respective probe spot.

The method further comprises displaying, in a first window on the display, pixel values of all or portion of a first two-dimensional image in the one or more two-dimensional images of the first projection.

The method further comprises overlaying on the first two-dimensional image and co-aligned with the first two-dimensional image (i) first indicia for each probe spot in the plurality of probe spots that have been assigned to a first cluster in the plurality of clusters and (ii) second indicia for each probe spot in the plurality of probe spots that have been assigned to a second cluster in the plurality of clusters, thereby identifying the morphological pattern.

In some embodiments, the one or more spatial projections is a plurality of spatial projections of the biological sample, the plurality of spatial projections comprises the first spatial projection for a first tissue section of the biological sample, and the plurality of spatial projections comprises a second spatial projection for a second tissue section of the biological sample. In some such embodiments, the one or more two-dimensional images for the first spatial projection comprises a first plurality of two-dimensional images, and the second spatial projection comprises a second plurality of two-dimensional images.

In some embodiments, each two-dimensional image in the first plurality two-dimensional images is taken of the first tissue section of the biological sample, and each two-dimensional image in the second plurality two-dimensional images is taken of a second tissue section of the biological sample.

In some embodiments, each two-dimensional image of the first plurality of two-dimensional images is displayed, co-aligned with the (i) first indicia for each probe spot in the plurality of probe spots that have been assigned to the first cluster and (ii) second indicia for each probe spot in the plurality of probe spots that have been assigned to the second cluster. In some such embodiments, the method further comprises, responsive to receiving user display instructions, displaying or removing from display one or more two-dimensional images in the first plurality of two-dimensional images.

In some embodiments, each respective two-dimensional image in the first plurality of two-dimensional images is acquired from the first tissue section using a different wavelength or different wavelength band.

In some embodiments the one or more spatial projections is a single spatial projection, the one or more two-dimensional images of the first spatial projection is a plurality of two-dimensional images, a first two-dimensional image in the plurality of two-dimensional images is a bright-field image of the first tissue section, a second two-dimensional image in the plurality of two-dimensional images is a first immunohistochemistry (IHC) image of the first tissue section taken at a first wavelength or a first wavelength range, and a third two-dimensional image in the plurality of two-dimensional images is a second immunohistochemistry (IHC) image of the first tissue section taken at a second wavelength or a second wavelength range that is different than the first wavelength or the first wavelength range. In some such embodiments, the first two-dimensional image is acquired using Haemotoxylin and Eosin, a Periodic acid-Schiff reaction stain, a Masson's trichrome stain, an Alcian blue stain, a van Gieson stain, a reticulin stain, an Azan stain, a Giemsa stain, a Toluidine blue stain, an isamin blue/eosin stain, a Nissl and methylene blue stain, a sudan black and/or osmium staining of the biological sample.

In some embodiments, the method further comprises storing the first two-dimensional image in a first schema, wherein the first schema comprises a first number of tiles and storing the first two-dimensional image in a second schema, wherein the second schema comprises a second number of tiles, where the second number of tiles is less than the first number of tiles. In some such embodiments, responsive to receiving display instructions for a user, the method further comprises switching from the first schema to the second schema in order to display all or a portion of the first two-dimensional image or switching from the second schema to the first schema in order to display all or a portion of the first two-dimensional image. In some embodiments, at least a first tile in the first number of tiles comprises a first predetermined tile size, at least a second tile in the first number of tiles comprises a second predetermined tile size, and at least a first tile in the second number of tiles comprises of a third predetermined tile size.

In some embodiments, the discrete attribute value dataset redundantly represents a first discrete attribute value for each respective locus in the plurality of loci of each probe spot in the plurality of probe spots and the corresponding second discrete attribute value for each respective probe spot in the plurality of probe spots for a first spatial projection in the one or more spatial projections in both a compressed sparse row format and a compressed sparse column format in which first and second discrete attribute values that have a null discrete attribute data value are discarded.

In some embodiments, the obtaining a corresponding cluster assignment comprises clustering all or a subset of the probe spots in the plurality of probe spots across the one or more spatial projections using the discrete attribute values assigned to each respective probe spot in each of the one or more spatial projections as a multi-dimensional vector, where the clustering is configured to load less than the entirety of the discrete attribute value dataset into a non-persistent memory during the clustering thereby allowing the clustering of the discrete attribute value dataset having a size that exceeds storage space in a non-persistent memory allocated to the discrete attribute value dataset. In some embodiments, the clustering of all or a subset of the probe spots comprises k-means clustering with K set to a predetermined value between one and twenty-five.

In some embodiments, each respective cluster in the plurality of clusters consists of a unique subset of the plurality of probe spots.

In some embodiments, at least one probe spot in the plurality of probe spots is assigned to more than one cluster in the plurality of clusters with a corresponding probability value indicating a probability that the at least one probe spot belongs to a respective cluster of the plurality of clusters.

In some embodiments, each locus in the plurality of loci is a respective gene in a plurality of genes, and each discrete attribute value in the corresponding plurality of discrete attribute values is a count of unique molecular identifier (UMI) that map to a corresponding probe spot and that also map to a respective gene in the plurality of genes. In some such embodiments, the discrete attribute value dataset represents a whole transcriptome sequencing experiment that quantifies gene expression in counts of transcript reads mapped to the plurality of genes. In some embodiments, the discrete attribute value dataset represents a targeted transcriptome sequencing experiment that quantifies gene expression in UMI counts mapped to probes in the plurality of probes.

In some embodiments, the first indicate is a first graphic or a first color, and the second indicate is a second graphic or a second color.

In some embodiments, each locus in the plurality of loci is a respective feature in a plurality of features, each discrete attribute value in the corresponding plurality of discrete attribute values is a count of UMI that map to a corresponding probe spot and that also map to a respective feature in the plurality of features, and each feature in the plurality of features is an open-reading frame, an intron, an exon, an entire gene, an mRNA transcript, a predetermined non-coding part of a reference genome, an enhancer, a repressor, a predetermined sequence encoding a variant allele, or any combination thereof.

In some embodiments, the plurality of loci comprises more than 50 loci, more than 100 loci, more than 250 loci, more than 500 loci, more than 1000 loci, or more than 10000 loci.

In some embodiments, each unique barcode encodes a unique predetermined value selected from the set $\{1, \ldots, 1024\}$, $\{1, \ldots, 4096\}$, $\{1, \ldots, 16384\}$, $\{1, \ldots, 65536\}$, $\{1, \ldots, 262144\}$, $\{1, \ldots, 1048576\}$, $\{1, \ldots, 4194304\}$, $\{1, \ldots, 16777216\}$, $\{1, \ldots, 67108864\}$, or $\{1, \ldots, 1 \times 10^{12}\}$.

In some embodiments, the plurality of loci include one or more loci on a first chromosome and one or more loci on a second chromosome other than the first chromosome.

In some embodiments, cells in the first tissue section that map to the probe spots of the first cluster are a first cell type and cells in the first tissue section that map to the probe spots of the second cluster are a second cell type. In some such embodiments, the first cell type is diseased cells and the second cell type is lymphocytes.

In some embodiments, cells in the first tissue section that map to the probe spots of the first cluster are a first tissue type and cells in the first tissue section that map to the probe spots of the second cluster are a second tissue type. In some such embodiments, the first tissue type is healthy tissue and the second tissue type is diseased tissue.

In some embodiments, the morphological pattern is a spatial arrangement of probe spots assigned to the first cluster relative to probe spots assigned to the second cluster.

In some embodiments, the method further comprises, in response to a first user selection of a first subset of probe spots using the displayed pixel values of the first two-dimensional image, assigning the first subset of probe spots to the first cluster, and, in response to receiving a second user selection of a second subset of probe spots using the displayed pixel values of the first two-dimensional image, assigning the second subset of probe spots to the second cluster.

In some embodiments, the method further comprises in response to a first user selection of a first subset of probe spots using displayed discrete attribute values of an active list of genes superimposed on the first two-dimensional image, assigning the first subset of probe spots to the first cluster, and, in response to a second user selection of a second subset of probe spots using displayed discrete attribute values of an active list of genes superimposed on the first two-dimensional image, assigning the second subset of probe spots to the second cluster.

In some embodiments, the one or more spatial projections is a plurality of spatial projections, the discrete attribute value dataset further comprises one or more two-dimensional images for the second spatial projection, each two-dimensional image in the one or more two-dimensional images of the second spatial projection (a) taken of a second tissue section, obtained from the biological sample, overlaid on a substrate having the plurality of probe spots arranged in the spatial arrangement and (b) comprising at least 100,000 pixel values. Further, the method further comprises in some such embodiments the display, in a second window on the display, pixel values of all or portion of a first two-dimensional image in the one or more two-dimensional images of the second projection. In some such embodiments, the method further comprises linking cluster selection, cluster creation, loci selection, cluster membership, or cluster indicia selection between the first window and the second window.

In some embodiments, a file size of the discrete attribute value dataset is more than 100 megabytes Another aspect of the present disclosure provides a computing system comprising at least one processor and memory storing at least one program to be executed by the at least one processor, the at least one program comprising instructions for identifying a morphological pattern by any of the methods disclosed above.

Still another aspect of the present disclosure provides a non-transitory computer readable storage medium storing one or more programs for identifying a morphological pattern. The one or more programs are configured for execution by a computer. The one or more programs collectively encode computer executable instructions for performing any of the methods disclosed above.

As disclosed herein, any embodiment disclosed herein when applicable can be applied to any aspect.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The implementations disclosed herein are illustrated by way of example, and not by way of limitation, in the figures of the accompanying drawings. Like reference numerals refer to corresponding parts throughout the several views of the drawings.

FIGS. 2A and 2B collectively illustrate an example method in accordance with an embodiment of the present disclosure, in which optional steps are indicated by dashed lines.

DETAILED DESCRIPTION

Figure 1A:
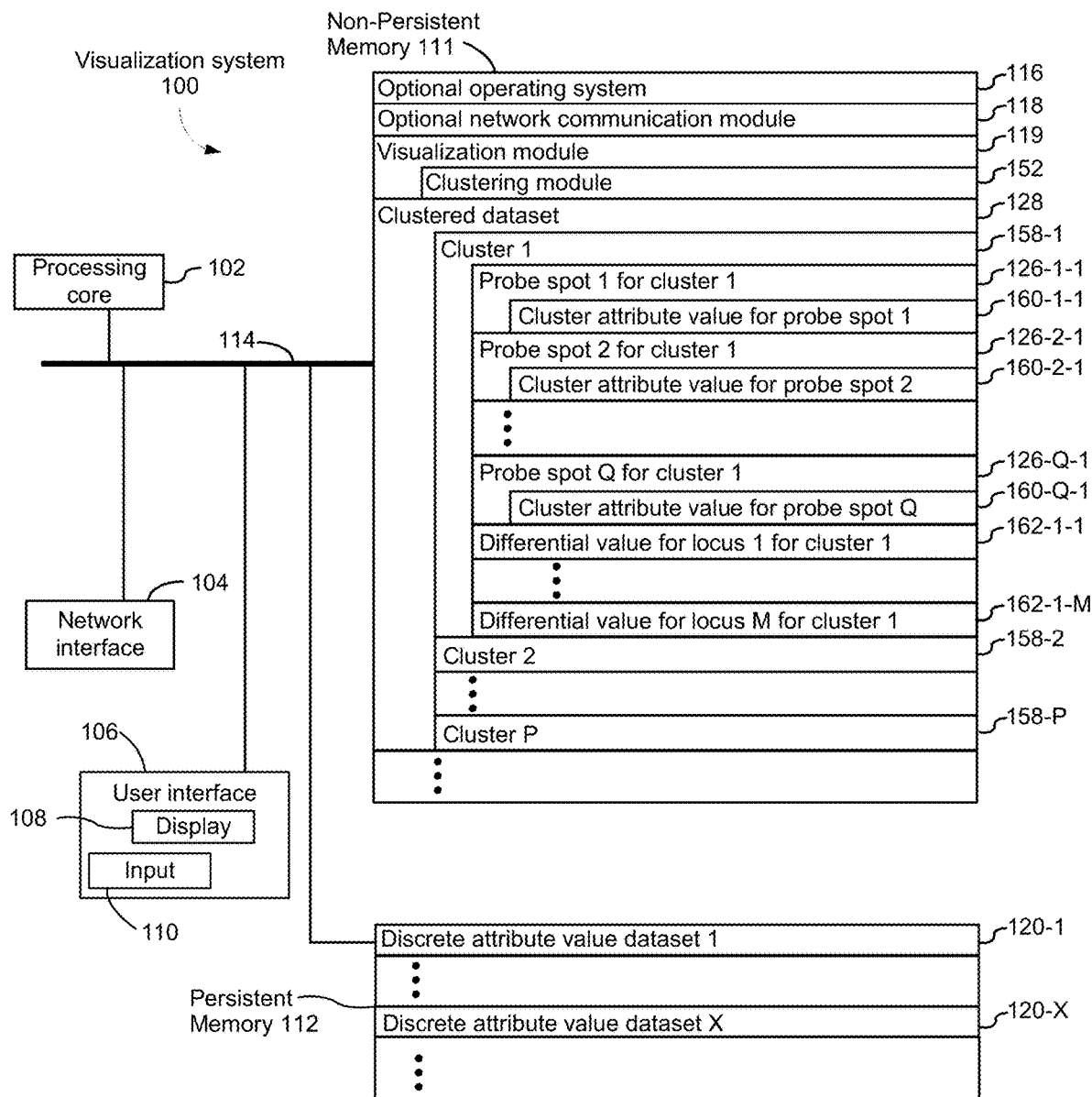
FIGS. 1A, 1B, and 1C are an example block diagram illustrating a computing device in accordance with some embodiments of the present disclosure.

The methods described herein provide for the ability to view spatial genomics data and proteomics data in the original context of one or more microscope images of a biological sample. In particular, in some embodiments, a tissue sample (e.g., fresh-frozen tissue, formalin-fixed paraffin-embedded, etc.) is placed onto a capture area of a substrate (e.g., slide, coverslip, semiconductor wafer, chip, etc.). Each capture area includes preprinted or affixed spots of barcoded capture probes, where each such probe spot has a corresponding unique barcode. The capture area is imaged and then cells within the tissue are permeabilized in place, enabling the capture probes to bind to RNA from cells in proximity to (e.g., on top and/or laterally positioned with respect to) the probe spots. In some embodiments, two-dimensional spatial sequencing is performed by obtaining barcoded cDNA and then sequencing libraries from the bound RNA, and the barcoded cDNA is then separated (e.g., washed) from the substrate. The sequencing libraries are run on a sequencer and sequencing read data is generated and applied to a sequencing pipeline.

Reads from the sequencer are grouped by barcodes and UMIs, aligned to genes in a transcriptome reference, after which the pipeline generates a number of files, including a feature-barcode matrix. The barcodes correspond to individual spots within a capture area. The value of each entry in the spatial feature-barcode matrix is the number of RNA molecules in proximity to (e.g., on top and/or laterally positioned with respect to) the probe spot affixed with that barcode, that align to a particular gene feature. The method then provides for displaying the relative abundance of features (e.g., expression of genes) at each probe spot in the capture area overlaid on the image of the original tissue. This enables users to observe patterns in feature abundance (e.g., gene or protein expression) in the context of tissue samples. Such methods provide for improved pathological examination of patient samples.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to detect a pattern in datasets. An example of such datasets are datasets arising from whole transcriptome sequencing pipelines that quantify gene expression at particular probe spots in counts of transcript reads mapped to genes. Details of implementations are now described in conjunction with the Figures.

General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharamoyces cerevisiae* or *Schizosaccharomyces pombe*; or a *Plasmodium falciparum*.

(ii) Nucleic Acid and Nucleotide.

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or nucleic acid sequence, is intended as a semantic identifier for the nucleic acid or sequence in the context of a method or composition, and does not limit the structure or function of the nucleic acid or sequence beyond what is expressly indicated.

(iv) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, a barcode can be or can include a "spatial barcode". In some embodiments, a barcode includes both a UMI and a spatial barcode. In some embodiments the UMI and barcode are separate entities. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. More details on barcodes and UMIs is disclosed in U.S. Provisional Patent Application No. 62/980,073, entitled "Pipeline for Analysis of Analytes," filed Feb. 21, 2020, which is hereby incorporated by reference.

Additional definitions relating generally to spatial analysis of analytes are found in U.S. Provisional Patent Application No. 62/886,233 entitled "SYSTEMS AND METHODS FOR USING THE SPATIAL DISTRIBUTION OF HAPLOTYPES TO DETERMINE A BIOLOGICAL CONDITION," filed Aug. 13, 2019, which is hereby incorporated herein by reference.

(v) Chip/Substrate

As used herein, the terms "chip" and "substrate" are used interchangeably and refer to any surface onto which capture probes can be affixed (e.g., a solid array, a bead, a coverslip, etc). More details on suitable substrates is disclosed in U.S. Provisional Patent Application No. 62/980,073, entitled "Pipeline for Analysis of Analytes," filed Feb. 21, 2020, which is hereby incorporated by reference.

(vi) Biological Samples.

As used herein, a "biological sample" is obtained from the subject for analysis using any of a variety of techniques including, but not limited to, biopsy, surgery, and laser capture microscopy (LCM), and generally includes tissues or organs and/or other biological material from the subject.

Biological samples can include one or more diseased cells. A diseased cell can have altered metabolic properties, gene expression, protein expression, and/or morphologic features. Examples of diseases include inflammatory disorders, metabolic disorders, nervous system disorders, neurological disorders and cancer. Cancer cells can be derived from solid tumors, hematological malignancies, cell lines, or obtained as circulating tumor cells.

System.

FIG. 1A is a block diagram illustrating a visualization system 100 in accordance with some implementations. The device 100 in some implementations includes one or more processing units CPU(s) 102 (also referred to as processors), one or more network interfaces 104, a user interface 106 comprising a display 108 and an input module 110, a non-persistent 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the visualization system 100 with other devices or a communication network;
- a visualization module 119 for selecting a discrete attribute value dataset 120 and presenting information about the discrete attribute value dataset 120, where the discrete attribute value dataset 120 comprises a corresponding discrete attribute value 124 (e.g., count of transcript reads mapped to a single locus) for each locus 122 (e.g., single gene) in a plurality of loci (e.g., a genome of a species) for each respective probe spot 126 (e.g., particular location on a substrate) in a plurality of probe spots (e.g., set of all locations on a substrate) for each image 125 for each spatial projection 121;
- an optional clustering module 152 for clustering a discrete attribute value dataset 120 using the discrete attribute values 124 for each locus 122 in the plurality of loci for each respective probe spot 126 in the plurality of probe spots for each image 125 for each spatial projection 121, or principal component values 164 derived therefrom, thereby assigning respective probe spots to clusters 158 in a plurality of clusters in a clustered dataset 128; and
- optionally, all or a portion of a clustered dataset 128, the clustered dataset 128 comprising a plurality of clusters 158, each cluster 158 including a subset of probe spots 126, and each respective cluster 158 including a differential value 162 for each locus 122 across the probe spots 126 of the subset of probe spots for the respective cluster 158.

In some implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

FIG. 1A illustrates that the clustered dataset 128 includes a plurality of clusters 158 comprising cluster 1 (158-1), cluster 2 (158-2) and other clusters up to cluster P (158-P), where P is a positive integer. Cluster 1 (158-1) is stored in association with probe spot 1 for cluster 1 (126-1-1), probe spot 2 for cluster 1 (126-2-1), and subsequent probe spots up to probe spot Q for cluster 1 (126-Q-1), where Q is a positive integer. As shown for cluster 1 (158-1), the cluster attribute value for probe spot 1 (160-1-1) is stored in association with the probe spot 1 for cluster 1 (126-1-1), the cluster attribute value for the probe spot 2 (160-2-1) is stored in association with the probe spot 2 for cluster 1 (126-2-1), and the cluster attribute value for the probe spot Q (160-Q-1) is stored in association with the probe spot Q for cluster 1 (126-Q-1). The clustered dataset 128 also includes differential value for locus 1 for cluster 1 (162-1-1) and subsequent differential values up to differential value for locus M for cluster 1 (162-1-M). Cluster 2 (158-2) and other clusters up to cluster P (158-P) in the clustered dataset 128 can include information similar to that in cluster 1 (158-1), and each cluster in the clustered dataset 128 is therefore not described in detail. A discrete attribute value dataset 120, which is store in the persistent memory 112, includes discrete attribute value dataset 120-1 and other discrete attribute value datasets up to discrete attribute value dataset 120-X.

Figure 1B:
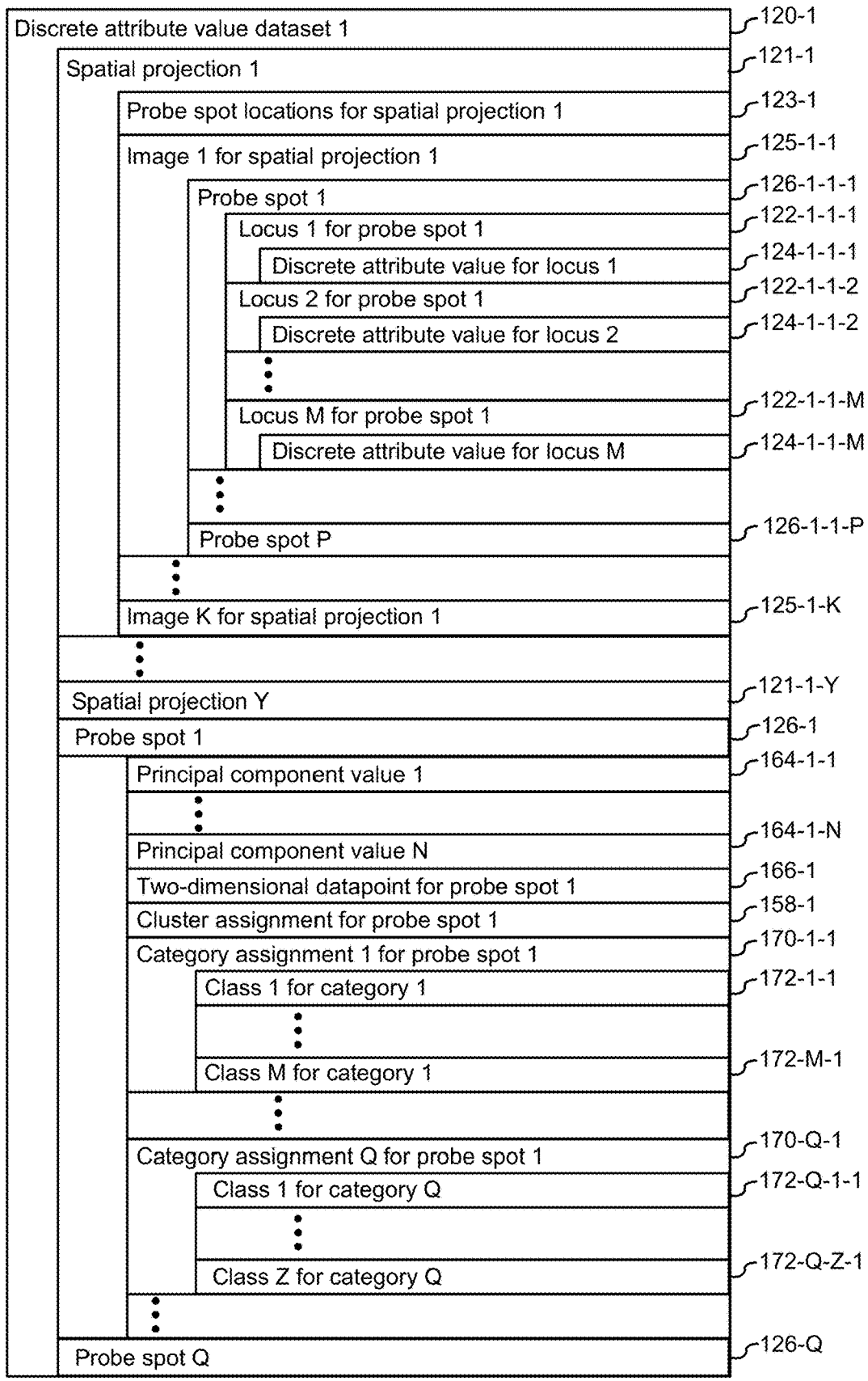

Referring to FIG. 1B, persistent memory 112 stores one or more discrete attribute value datasets 120. Each discrete attribute value dataset 120 comprises one or more spatial projections 121. In some embodiments, a discrete attribute value dataset 120 comprises a single spatial projection 121. In some embodiments, a discrete attribute value dataset 120 comprises a plurality of spatial projections. Each spatial projection 121 has an independent set of images 125, and a distinct set of probe locations 123. However, in typical embodiments, a discrete attribute value dataset 120 contains a single feature barcode matrix. In other words, the probe set used in each of the spatial projections 125 in a particular single given discrete attribute value dataset 120 are the same. Moreover, the probe set used in each of the images of a particular spatial projection 125 are the same. Accordingly, in some embodiments, the probes of a probe set contain a suffix, or other form of indicator, that indicates which spatial projection 121 a given probe spot (and subsequent measurements) originated. For instance, the barcode (probe) ATAAA-1 from spatial projection (capture area) 1 (121-1-1) will be different from ATAAA-2 from spatial projection (capture area) 2 (121-1-2).

In some embodiments, an image 125 is a bright-field microscopy image, in which the imaged sample appears dark on a bright background. In some such embodiments, the sample has been stained. For instance, in some embodiments the sample has been stained with Haemotoxylin and Eosin and the image 125 is a bright-field microscopy image. In some embodiments the sample has been stained with a Periodic acid-Schiff reaction stain (stains carbohydrates and carbohydrate rich macromolecules a deep red color) and the image is a bright-field microscopy image. In some embodiments the sample has been stained with a Masson's trichrome stain (nuclei and other basophilic structures are stained blue, cytoplasm, muscle, erythrocytes and keratin are stained bright-red, collagen is stained green or blue, depending on which variant of the technique is used) and the image is a bright-field microscopy image. In some embodiments the sample has been stained with an Alcian blue stain (a mucin stain that stains certain types of mucin blue, and stains cartilage blue and can be used with H&E, and with van Gieson stains) and the image is a bright-field microscopy image. In some embodiments the sample has been stained with a van Gieson stain (stains collagen red, nuclei blue, and erythrocytes and cytoplasm yellow, and can be combined with an elastin stain that stains elastin blue/black) and the image is a bright-field microscopy image. In some embodiments the sample has been stained with a reticulin stain, an Azan stain, a Giemsa stain, a Toluidine blue stain, an isamin blue/eosin stain, a Nissl and methylene blue stain, and/or a sudan black and osmium stain and the image is a bright-field microscopy image. In some embodiments, the sample has been stained with an immunofluorescence (IF) stain (e.g., an immunofluorescence label conjugated to an antibody). In some embodiments, biological samples are stained as described in I. Introduction; (d) Biological samples; (ii) Preparation of biological samples; (6) staining of U.S. Provisional Patent Application No. 62/938,336, entitled "Pipeline for Analysis of Analytes," filed Nov. 21, 2019, which is hereby incorporated by reference in its entirety.

In some embodiments, rather than being a bright-field microscopy image of a sample, an image 125 is an immunohistochemistry (IHC) image. IHC imaging relies upon a staining technique using antibody labels. One form of immunohistochemistry (IHC) imaging is immunofluorescence (IF) imaging. In an example of IF imaging, primary antibodies are used that specifically label a protein in the biological sample, and then a fluorescently labelled secondary antibody or other form of probe is used to bind to the primary antibody, to show up where the first (primary) antibody has bound. A light microscope, equipped with fluorescence, is used to visualize the staining. The fluorescent label is excited at one wavelength of light, and emits light at a different wavelength. Using the right combination of filters, the staining pattern produced by the emitted fluorescent light is observed. In some embodiments, a biological sample is exposed to several different primary antibodies (or other forms of probes) in order to quantify several different proteins in a biological sample. In some such embodiments, each such respective different primary antibody (or probe) is then visualized with a different fluorescence label (different channel) that fluoresces at a unique wavelength or wavelength range (relative to the other fluorescence labels used). In this way, several different proteins in the biological sample can be visualized.

More generally, in some embodiments of the present disclosure, in addition to brightfield imaging or instead of brightfield imaging, fluorescence imaging is used to acquire one or more spatial images of the sample. As used herein the term "fluorescence imaging" refers to imaging that relies on the excitation and re-emission of light by fluorophores, regardless of whether they're added experimentally to the sample and bound to antibodies (or other compounds) or simply natural features of the sample. The above-described IHC imaging, and in particular IF imaging, is just one form of fluorescence imaging. Accordingly, in some embodiments, each respective image 125 in a single spatial projection (e.g., of a biological sample) represents a different channel in a plurality of channels, where each such channel in the plurality of channels represent an independent (e.g., different) wavelength or a different wavelength range (e.g., corresponding to a different emission wavelength). In some embodiments, the images 125 of a single spatial projection will have been taken of a tissue (e.g., the same tissue section) by a microscope at multiple wavelengths, where each such wavelength corresponds to the excitation frequency of a different kind of substance (containing a fluorophore) within or spatially associated with the sample. This substance can be a natural feature of the sample (e.g., a type of molecule that is naturally within the sample), or one that has been added to the sample. One manner in which such substances are added to the sample is in the form of probes that excite at specific wavelengths. Such probes can be directly added to the sample, or they can be conjugated to antibodies that are specific for some sort of antigen occurring within the sample, such as one that is exhibited by a particular protein. In this way, a user can use the spatial projection, comprising a plurality of such images 125 to be able to see capture spot data mapped to (e.g., on top of) fluorescence image data, and to look at the relation between gene (or antibody) expression against another cellular marker, such as the spatial abundance of a particular protein that exhibits a particular antigen. In typical embodiments, each of the images 125 of a given spatial projection will have the same dimensions and position relative to a single set of capture spot locations associated with the spatial projection. Each respective spatial projection in a discrete attribute value dataset will have its own set of capture spot locations associated with the respective spatial projection. Thus, for example, even though a first and second spatial projection in a given discrete attribute dataset make use of the same probe set, they will both have their own set of capture spot locations for this probe set. This is because, for example, each spatial projection represents images that are taken from an independent target (e.g., different tissue sections, etc.).

In some embodiments, both a bright-field microscopy image and a set of fluorescence images (e.g., immunohistochemistry images) are taken of a biological sample and are in the same spatial projection for the biological sample.

In some embodiments, a biological sample is exposed to several different primary antibodies (or other forms of probes) in order to quantify several different proteins in a biological sample. In some such embodiments, each such respective different primary antibody (or probe) is then visualized with a corresponding secondary antibody type that is specific for one of the types of primary antibodies. Each such corresponding secondary antibody type is labeled with a different fluorescence label (different channel) that fluoresces at a unique wavelength or wavelength range (relative to the other fluorescence labels used). In this way, several different proteins in the biological sample can be visualized. Accordingly, in some embodiments, each respective image 125 in a single spatial projection 121 represents a different channel in a plurality of channels, where each such channel in the plurality of channels represent an independent (e.g., different) wavelength or a different wavelength range (corresponding to a different fluorescence label). Such an architecture supports visualization of probe spots mapped to (e.g., on top of) immunofluorescent images for the reasons discussed above. In some embodiments, the images 125 of a single spatial projection 121 will have been taken of a tissue by a microscope at multiple wavelengths, where each such wavelength corresponds to the excitation frequency of a probe bound to some sort of marker, typically a protein. In this way, a user can use the spatial projection 121, comprising a plurality of such images 125 to be able to see probe spot data mapped to (e.g., on top of) fluorescent image data, and to look at the relation between gene (or protein) expression against another cellular marker. In typical embodiments, each of the images 125 of a given spatial projection 121 will have the same dimensions and position relative to a single set of probe spot locations associated with the spatial projection. Each respective spatial projection in a discrete attribute value dataset 120 will have its own set of probe spot locations associated with the respective spatial projection. Thus, for example, even though a first and second spatial projection in a given discrete attribute dataset 121 make use of the same probe set, they will both have their own set of probe spot locations for this probe set. This is because, for example, each spatial projection represents images that are taken from an independent target (e.g., different tissue sections, etc.). Example probe spot dimensions and density is disclosed in U.S. Provisional Application No. 62/938,336, entitled "Pipeline for Analysis of Analytes," filed Nov. 21, 2019, which is hereby incorporated by reference, where the term "capture spot" is used interchangeably with the term "probe spot."

In some embodiments, both a bright-field microscopy image and a set of fluorescence images (e.g., immunohistochemistry images) are taken of a biological sample and are in the same spatial projection 121.

As illustrated in FIG. 1B, in some embodiments, an image 125 comprises, for each respective probe spot 126 in a plurality of probe spots (associated with the corresponding dataset), a discrete attribute value 124 for each locus 122 in a plurality of loci. For example, as shown in FIG. 1B, a discrete attribute value dataset 120-1 (shown by way of example) includes information related to probe spot 1 (126-1-1-1), probe spot 2 (126-1-1-2) and other probe spots up to probe spot Y (126-1-1-Y) for each image 125 of each spatial projection 121.

As shown for probe spot 1 (126-1-1-1) of image 125-1-1 of spatial projection 121-1, the probe spot 1 (126-1-1-1) includes a discrete attribute value 124-1-1-1 of locus 1 for probe spot 1 (122-1-1-1), a discrete attribute value 124-1-1-2 of locus 2 for probe spot 1 (122-1-1-1), and other discrete attribute values up to discrete attribute value 124-1-1-M of locus M for probe spot 1 (122-1-1-1). In some embodiments, each locus is a different locus in a reference genome. More generally, each locus is a different feature (e.g., antibody, location in a reference genome, etc.).

In some embodiments, the dataset further stores a plurality of principal component values 164 and/or a two-dimensional data point and/or a category 170 assignment for each respective probe spot 126 in the plurality of probe spots. FIG. 1B illustrates, by way of example, principal component value 1 164-1-1 through principal component value N 164-1-N stored for probe spot 126-1, where N is positive integer.

In the embodiment illustrated in FIG. 1B, the principal components are computed for the discrete attribute values of each respective probe spot, from each image 125, for each spatial projection 121 of the discrete attribute dataset 120. Thus, for example, if there are five images of a first spatial projection and six images of a second spatial projection, the principal component is taken across the variance observed in the discrete attribute value of the probe spot in each of the eleven images, where the assumption is made that the equivalent probe spot is known in the two projections. In some alternative embodiments, the principal components are computed for only a subset of the discrete attribute values of a probe spot across each spatial projection 121 of the discrete attribute dataset 120. In other words, the discrete attribute value for the probe spot in only a subset of the images is used. For instance, in some embodiments, the principal components are computed for a select set of loci 124 (rather than all the loci), from each image 125, across each spatial projection 121 of the discrete attribute dataset 120. In some embodiments, the principal components are computed for the discrete attribute values of the probe spot, from a subset of images, across each spatial projection 121 of the discrete attribute dataset 120.

In some alternative embodiments, the principal components are computed for the discrete attribute values of each instance of a probe spot across each image 125 for a single spatial projection 121 of the discrete attribute dataset 120. In some alternative embodiments, the principal components are computed for the discrete attribute values of each instance of a probe spot across each image 125 across a subset of the spatial projections 121 of the discrete attribute dataset 120. In some embodiments, a user selects this subset.

In some alternative embodiments, the principal components are computed for the discrete attribute values of each instance of a probe spot across a subset of the images 125 across each spatial projection 121 of the discrete attribute dataset 120. For instance, in some embodiments, a single channel (single image type) is user selected and the principal components are computed for the discrete attribute values of each instance of a probe spot across this single channel across each spatial projection 121 of the discrete attribute dataset 120.

FIG. 1B also illustrates how, in some embodiments, each probe spot is given a cluster assignment 158 (e.g., cluster assignment 158-1 for probe spot 1). In some embodiments, such clustering clusters based on discrete attribute values across all the images of all the spatial projections of a dataset. In some embodiment, some subset of the images, or some subset of the projections is used to perform the clustering.

FIG. 1B also illustrates one or more category assignments 170-1, . . . 170-Q, where Q is a positive integer, for each probe spot (e.g., category assignment 170-1-1, . . . 170-Q-1, for probe spot 1). In some embodiments, a category assignment includes multiple classes 172 (e.g., class 172-1, . . . , 172-M, such as class 172-1-1, . . . , 172-M-1 for probe spot 1, where M is a positive integer).

In some alternative embodiments, the discrete attribute value dataset 120 stores a two-dimensional data point 166 for each respective probe spot 126 in the plurality of probe spots (e.g., two-dimensional data point 166-1 for probe spot 1 in FIG. 1B) but does not store the plurality of principal component values 164.

In some embodiments, each probe spot represents a plurality of cells. In some embodiments, each probe spot represents a different individual cell (e.g., for liquid biopsy analysis where cells are clearly distinct on a substrate). In some embodiments, each locus represents a number of mRNA measured in the different probe spot that maps to a respective gene in the genome of the cell, and the dataset further comprises the total RNA counts per probe spot.

Figure 1C:
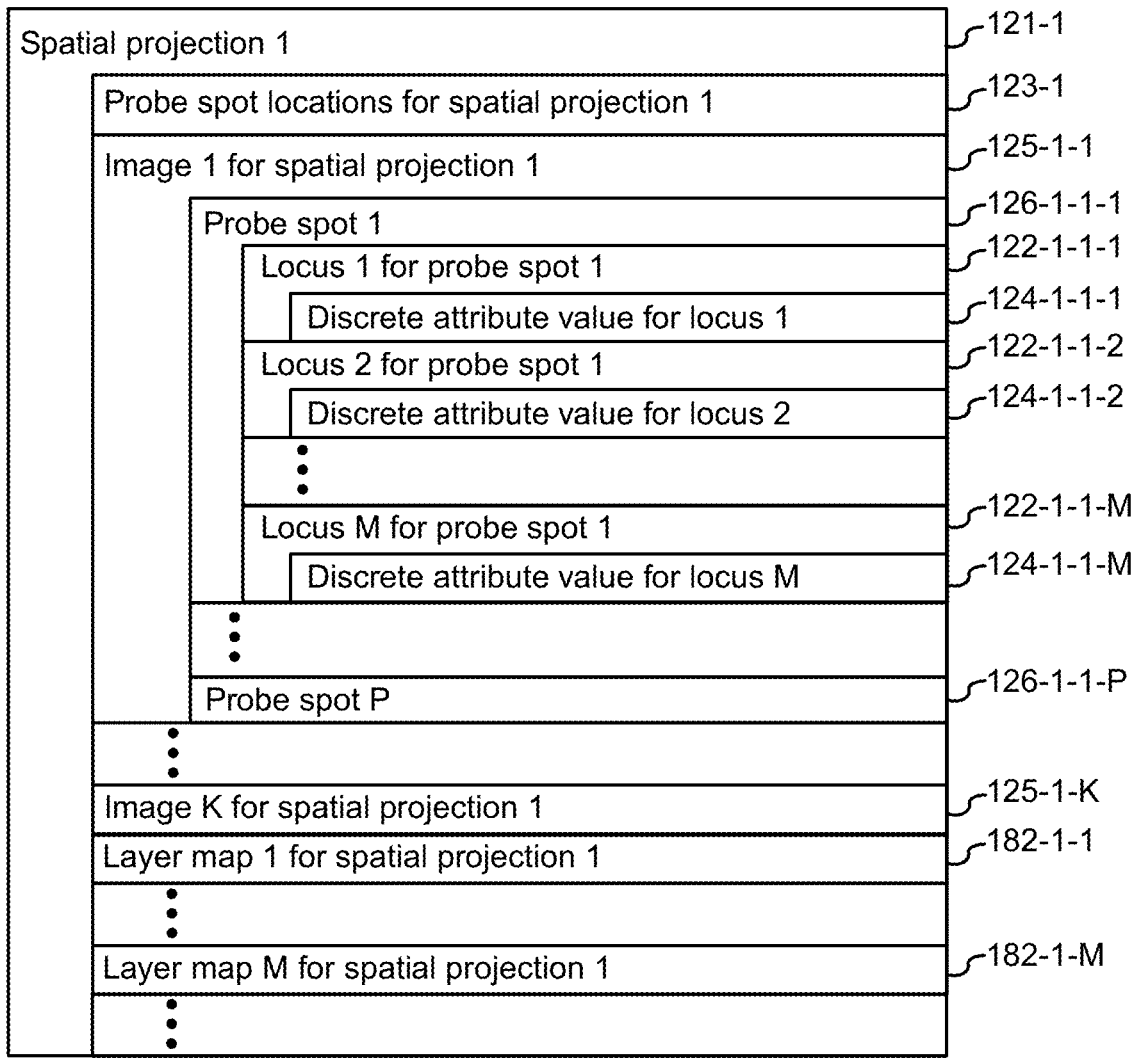

Referring to FIG. 1C, in some embodiments, one or more spatial projections each comprise one or more layer maps 182. In some embodiments, a layer map 182 is in the form of a binary map/probability map. In some embodiments, a layer map 182 is in the same space (orientation) as the one or more images 125 of the spatial projection 121 of a discrete attribute value dataset 120. The layer maps 182 provide a way to import various kinds of data into the visualization module 119 for co-display with images 125 of spatial projections 121 within a discrete attribute value dataset 120. For example, in the case where there is software external to the visualization module 119 that measures signal intensity in an image 125, such signal intensity measurements can be imported as a layer map 182. In some such embodiments, the layer map 182 comprises a two-dimensional array of pixel values, where the two-dimensional array has the same dimensions (pixelspace) as the two-dimensional array of pixel values of images 125 of the corresponding spatial projection 121. In such embodiments, each pixel in the layer map 125 contains information on measured signal intensity. In some embodiments, there are a plurality of layer maps 182 for a single corresponding spatial projection 121, where each layer map 182 in the plurality of layer maps represents a different type of measurement or processing of an image 125 of a spatial projection 121. For instance, in some such embodiments, each layer map 182 represents an analysis of a different stain, or a different combination of stains in a plurality of stains. In some such embodiments, each such stain or combination of stains is coded into the corresponding layer map and defines a tissue type and the probability of a specific tissue type by the greyscale value/color assigned to each specific pixel in the respective layer map 182. Because the pixelspace of the information in the respective layer map is the same as the one or more images 125 in the spatial projection 121 of the corresponding discrete attribute value dataset, each layer map 182 is readily overlayed onto the one or more images 125 of the corresponding discrete attribute value dataset. Moreover, additional operations can be performed to utilize the image coded in the layer map 182 such as selecting clusters based on a probability threshold. In some embodiments, the information coded into the pixelspace of a layer map 182 is the result of processing of the native pixel values of a corresponding image 125 in the discrete attribute value dataset. In such embodiments, a layer map 182 may represent a transformation of the corresponding image 125, where the transformation is a cell segmentation of probe spots in the corresponding image 125 based on different combinations of fluorescent markers present in the in the corresponding image 125, identification of tissue structures (e.g., glands) in the corresponding image 125, and/or identification of pathology (healthy vs diseased) in the corresponding image 125. In some embodiments, the layer map 182 represents a transformation of the corresponding image 125, where the transformation is an output of a trained machine learning algorithm, in which the corresponding images 125 is the input to the trained machine learning algorithm, and where the machine learning algorithm has been trained using on annotated training sets of images. Non-limiting examples of such machine learning algorithms for processing images are disclosed in U.S. Provisional Patent Application No. 62/977,565, entitled "Systems and Methods for Machine Learning Patterns in Biological Samples," filed February 2020, which is hereby incorporated by reference.

In some embodiments, a layer map 182 is derived from more than one image 125 of a corresponding spatial projection. For instance, in some embodiments, a layer map is derived from two images of a corresponding spatial projection. As one example, in some embodiments, a layer map comprises a Boolean combination of the corresponding pixel values of two images 125, for instance the summation or subtraction of the corresponding pixel values from the two images. As another example, in some embodiments, a layer map comprises a Boolean combination of the corresponding probe spot values (e.g., discrete attribute values 124) of two images 125, for instance the summation or subtraction of the corresponding pixel values from the two images for each locus for each probe spot.

Although FIGS. 1A, 1B, and 1C depict a "visualization system 100," the figures are intended more as functional description of the various features that may be present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules may be in persistent memory 112. Further, while discrete attribute value dataset 120 is depicted as resident in persistent memory 112, a portion of discrete attribute value dataset 120 is, in fact, resident in non-persistent memory 111 at various stages of the disclosed methods.

Methods.

Figure 2B:
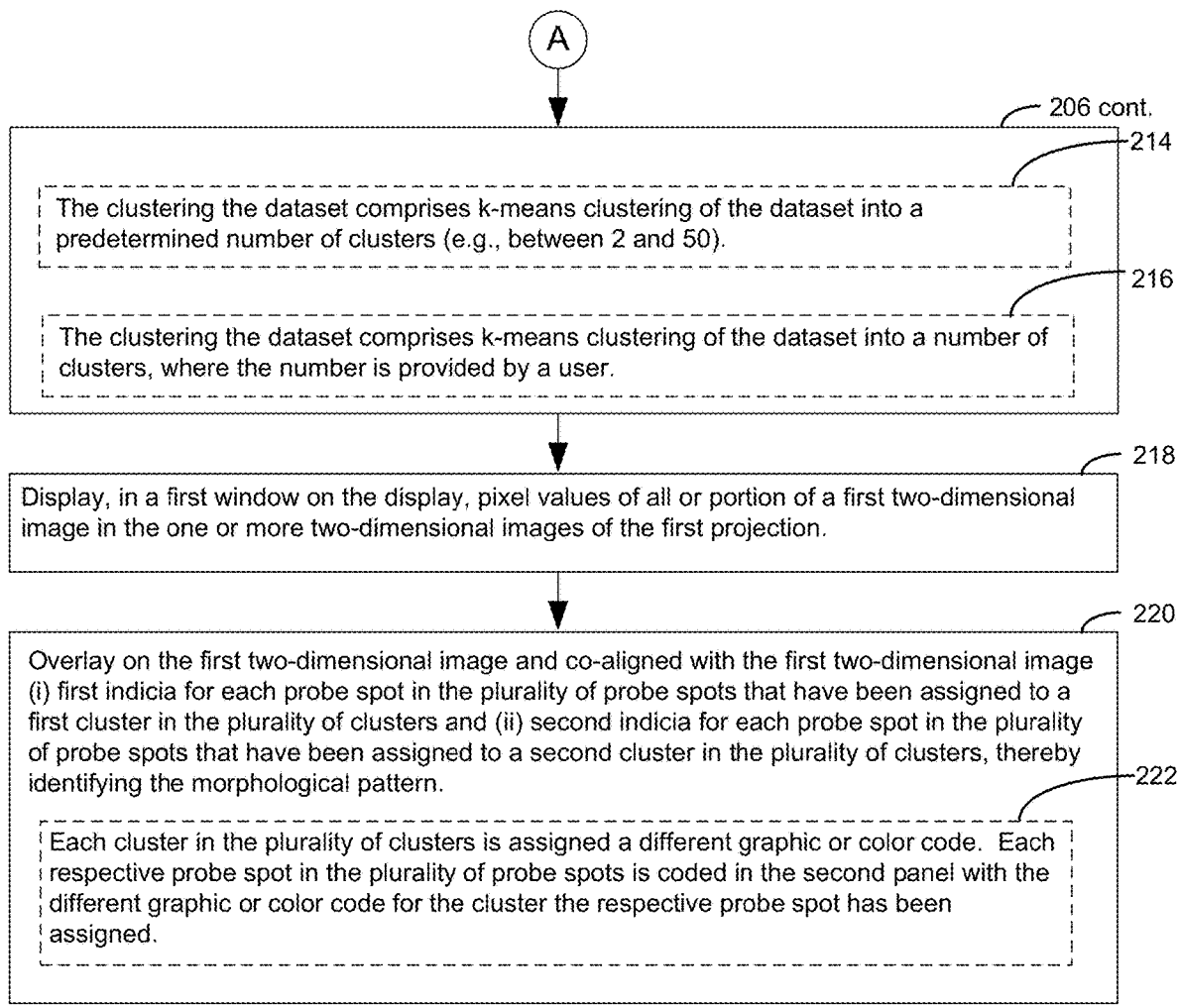

While a system in accordance with the present disclosure has been disclosed with reference to FIGS. 1A, 1B, and 1C a method in accordance with the present disclosure is now detailed with reference to FIGS. 2A, 2B, and 2C.

Block 202. One aspect of the present disclosure provides a visualization system 100. The visualization system 100 comprises one or more processing cores 102, a non-persistent memory 111 and a persistent memory 111, the persistent memory and the non-persistent memory collectively storing instructions for performing a method. A non-limiting example of a visualization system is collectively illustrated in FIGS. 1A, 1B, and 1C. As discussed above, it will be appreciated that the persistent memory and/or the non-persistent memory can be on a single computer, distributed across a network of computers, be represented by one or more virtual machines, or be part of a cloud computing architecture.

Block 204—Obtain a discrete attribute value dataset. A method in accordance with the systems and methods of the present disclosure comprises obtaining a discrete attribute value dataset associated with a plurality of probe spots having a spatial arrangement, where each probe spot in the plurality of probe spots is assigned a unique barcode in a plurality of barcodes and the plurality of probe spots comprises at least 1000 probe spots. The discrete attribute value dataset comprises: (i) one or more spatial projections 121 of a biological sample and (ii) one or more two-dimensional images 125, for a spatial projection in the one or more spatial projections. Each two-dimensional image in the one or more two-dimensional images is (a) taken of a first tissue section, obtained from the biological sample, overlaid on a substrate having the plurality of probe spots arranged in the spatial arrangement and (b) comprises at least 100,000 pixel values. In some embodiments, each two-dimensional image comprises at least 200,000 pixel values, at least 300,000 pixel values, at least 500,000 pixel values at least 1 million pixel values, at least 1 million pixel values, at least 2 million pixel values, at least 3 million pixel values, at least 4 million pixel values, at least 5 million pixel values, or at least 8 million pixel values.

The discrete attribute value dataset comprises (iii) a corresponding plurality of discrete attribute values 124 for each respective probe spot 126 in the plurality of probe spots obtained from two-dimensional spatial sequencing of the first tissue section. Each respective discrete attribute value in the corresponding plurality of discrete attribute values is for a different loci in a plurality of loci. In some embodiments, each corresponding plurality of discrete attribute values comprises at least 25 discrete attribute values, at least 50 discrete attribute values, at least 100 discrete attribute values, at least 500 discrete attribute values, or at least 1000 discrete attribute values.

Referring to FIG. 1B, the discrete attribute value dataset 120 comprises a corresponding discrete attribute value 124 for each locus 122 in a plurality of loci for each respective probe spot 126 in a plurality of probe spots for each image in a set of images for each spatial projection in the set of spatial projections. In some embodiments, in which there are multiple images in a single projection, it is possible for there to be only a single set of discrete attribute values. In other words, in such embodiments, the discrete attribute value dataset 120 comprises a corresponding discrete attribute value 124 for each locus 122 in a plurality of loci for each respective probe spot 126 in a plurality of probe spots for a respective spatial projection in a set of spatial projections, where the respective spatial projection may have any number of images (e.g., one image, two images, etc.).

In some embodiments, a discrete attribute value dataset 120 has a file size of more than 1 megabytes, more than 5 megabytes, more than 100 megabytes, more than 500 megabytes, or more than 1000 megabytes. In some embodiments, a discrete attribute value dataset 120 has a file size of between 0.5 gigabytes and 25 gigabytes. In some embodiments, a discrete attribute value dataset 120 has a file size of between 0.5 gigabytes and 100 gigabytes.

In some embodiments, each set of images is, in fact, a single image. In some embodiments, each set of images is, in fact, a plurality of images. In some embodiments, each set of images has an independent number of images meaning that there is no requirement that each spatial projection 121 in a discrete attribute dataset 120 has the same number of images. In some embodiments, the set of images of a particular spatial projection consists of 1, 2, 3, 4, 5, 6, 7, 8, 9, 10, 11, 12, 13, 14, 15, 16, 17, 18, 19, 20, or more than 20 images.

In some embodiments, one or more of the images include an image of other analytes, such as proteins in a biological sample.

In some embodiments, images in the set of images are acquired by exciting a target sample using a different wavelength or a different wavelength ranges.

In some embodiments, an image is acquired using transmission light microscopy (e.g., bright field transmission light microscopy, dark field transmission light microscopy, oblique illumination transmission light microscopy, dispersion staining transmission light microscopy, phase contrast transmission light microscopy, differential interference contrast transmission light microscopy, emission imaging, etc.). See, for example, Methods in Molecular Biology, 2018, *Light Microscopy Method and Protocols*, Markaki and Harz eds., Humana Press, New York, New York, ISBN-13: 978-1493983056, which is hereby incorporated by reference.

In some embodiments, each of the images in the set of images for a spatial projection is acquired by using a different bandpass filter that blocks out light other than a particular wavelength or set of wavelengths. In some embodiments, the set of images of a projection are images created using fluorescence imaging, for example, by making use of various immunohistochemistry (IHC) probes that excite at various different wavelengths. See, for example, Day and Davidson, 2014, "The Fluorescent Protein Revolution (In Cellular and Clinical Imaging)," CRC Press, Taylor & Francis Group, Boca Raton, Florida; "Quantitative Imaging in Cell Biology" Methods in Cell Biology 123, 2014, Wilson and Tran, eds.; Advanced Fluorescence Reporters in Chemistry and Biology II: Molecular Constructions, Polymers and Nanoparticles (Springer Series on Fluorescence), 2010, Demchenko, ed., Springer-Verlag, Berlin, Germany; Fluorescence Spectroscopy and Microscopy: Methods and Protocols (Methods in Molecular Biology) 2014th Edition, 2014, Engelborghs and Visser, eds., HumanPress; Maniatis, 2019, "Spatiotemporal Dynamics of Molecular Pathology in Amyotrophic Lateral Sclerosis," Science 364(6435), pp. 89-93, each of which is hereby incorporated by reference for their disclosure on fluorescence imaging.

In some embodiments, each set of images (e.g., each spatial projection) corresponds to a different tissue section in a collection of tissue sections taken from a biological sample, As the above disclosure indicated, IHC images are multispectral, meaning that instead of a single, visible-light spectrum image (which is supported by the present disclosure), with IHC a tissue is excited at different wavelengths and then each respective image 125 in a set of images for a given spatial projection 121 are collected at a specific excitation. As such, each of the images 125 in the set of images of a spatial projection 121 are co-aligned and represent the same region of interest of a biological target (e.g., the same tissue section or a sub-portion of the tissue section). Many works use multiple such "colors" and so each respective spatial projection (e.g., each tissue section or sub-portion of the tissue section) is inputted into the disclosed discrete attribute value dataset 120 with 1, 2, 3, 4, . . . Q different images 125 associated with it, where Q is a positive integer.

As disclosed in U.S. Provisional patent application Ser. No. 16/992,569, entitled "Systems and Methods for Using the Spatial Distribution of Haplotypes to Determine a Biological Condition," filed Aug. 13, 2020, which is hereby incorporated by reference, in some embodiments, the substrates have printed visible "fiducial" marks that the disclosed visualization module 119 identifies in brightfield images and performs alignment of the printed array pattern to the substrate. In some embodiments, a manual alignment tool in the disclosed visualization module 119 is used, where the end user is guided through steps to identify these marks. See, for example, U.S. Provisional Patent Application Nos. 62/938,967, entitled "Systems and Methods for Spatial Analysis of Analytes Using Fiducial Alignment," filed Nov. 22, 2019, and 62/938,336, entitled "Pipeline for Analysis of Analytes," filed Nov. 21, 2019, each of which is hereby incorporated by reference. For IHC, these fiducial marks are typically "lit-up" (excited) so that they are visible in the images 125.

In some embodiments, the visualization module 119, or a software module thereof, prepares data for the visualization module 119 using automatic segmentation of tissue images from H&E stained images. See, for example, U.S. Provisional Patent Application No. 62/937,066, entitled "Systems and Methods for Binary Tissue Classification," filed Nov. 18, 2019, which is hereby incorporated by reference.

Figure 3:
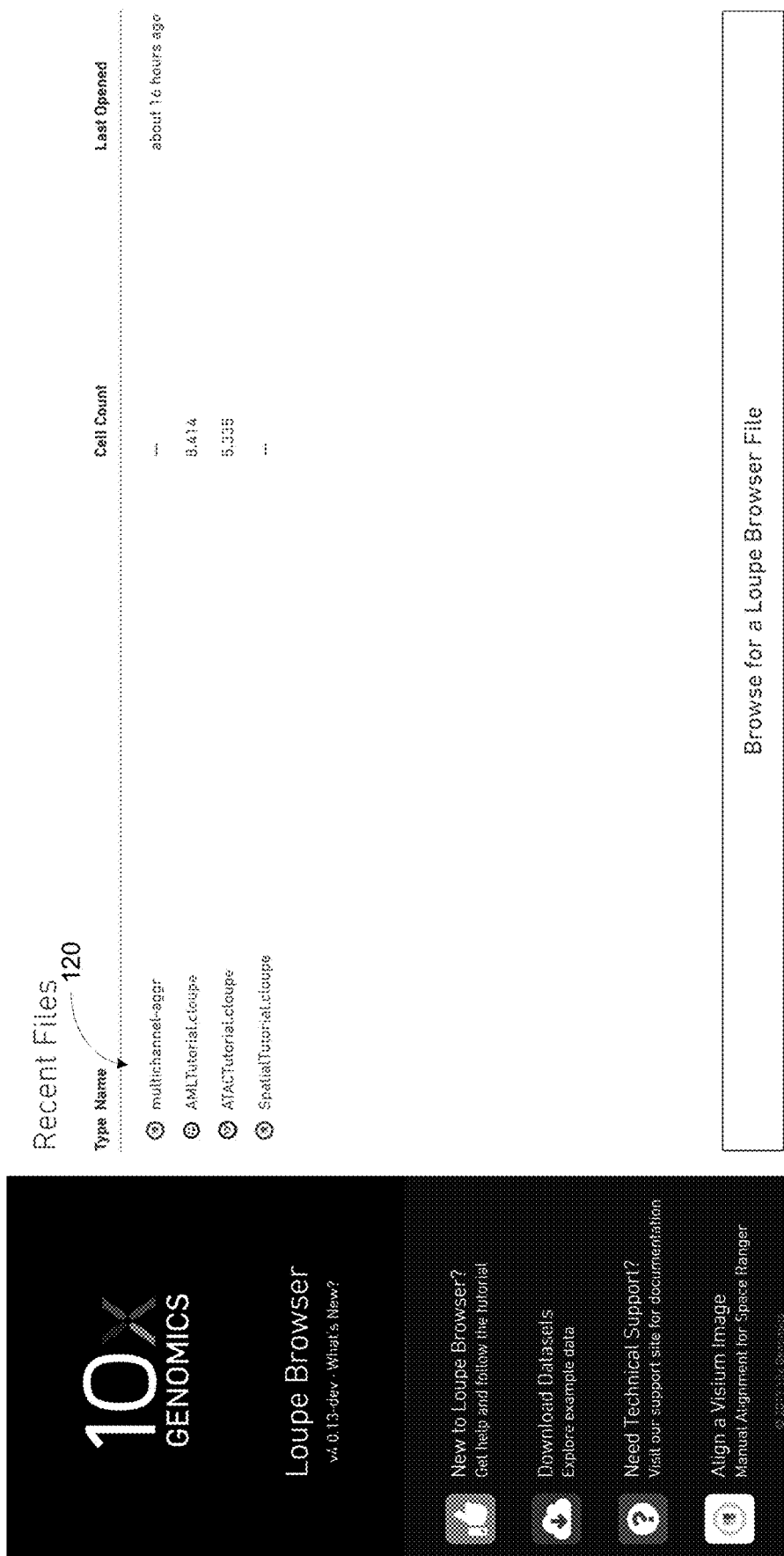
FIG. 3 illustrates a user interface for obtaining a dataset in accordance with some embodiments.

FIG. 3 illustrates the selection of a particular discrete attribute value dataset 120 using visualization module 119. In particular, FIG. 3 illustrates how, in some embodiments, the visualization module 119 provides some information regarding a given discrete attribute value dataset 120 such as its name and the last time the discrete attribute value dataset was accessed.

Referring to block 205, in some embodiments, each locus 122 in the plurality of loci is a respective gene in a plurality of genes. In some embodiments, each discrete attribute value 124 is a count of transcript reads (e.g., number of different UMI across a plurality of sequence reads that each have the spatial bar code of a given probe spot) within a the given probe spot that map to a respective gene in the plurality of genes. In such embodiments, each probe spot 126 corresponds to a single spatial region. In some embodiments, one hundred thousand or more, one million or more, ten million or more, or one hundred million or more sequence reads collected from a single tissue sample associated with an image in a projection are used to determine the unique UMI count (discrete attribute value) on a loci by loci and probe spot by probe spot basis in the discrete attribute value dataset 120. In some embodiments, the sequence reads for a respective image are 3'-end or 5'-end paired sequence reads.

In some embodiments, the discrete attribute value dataset 120 represents a whole transcriptome sequencing experiment that quantifies gene expression from a probe spot in counts of transcript reads mapped to the genes.

In some embodiments, a discrete attribute value dataset 120 represents a sequencing experiment in which baits are used to selectively filter and pull down a gene set of interest as disclosed, for example, in U.S. Provisional Patent Application No. 62/979,889, entitled "Capturing Targeted Genetic Targets Using a Hybridization/Capture Approach," filed Feb. 21, 2020, which is hereby incorporated by reference.

Figure 5:
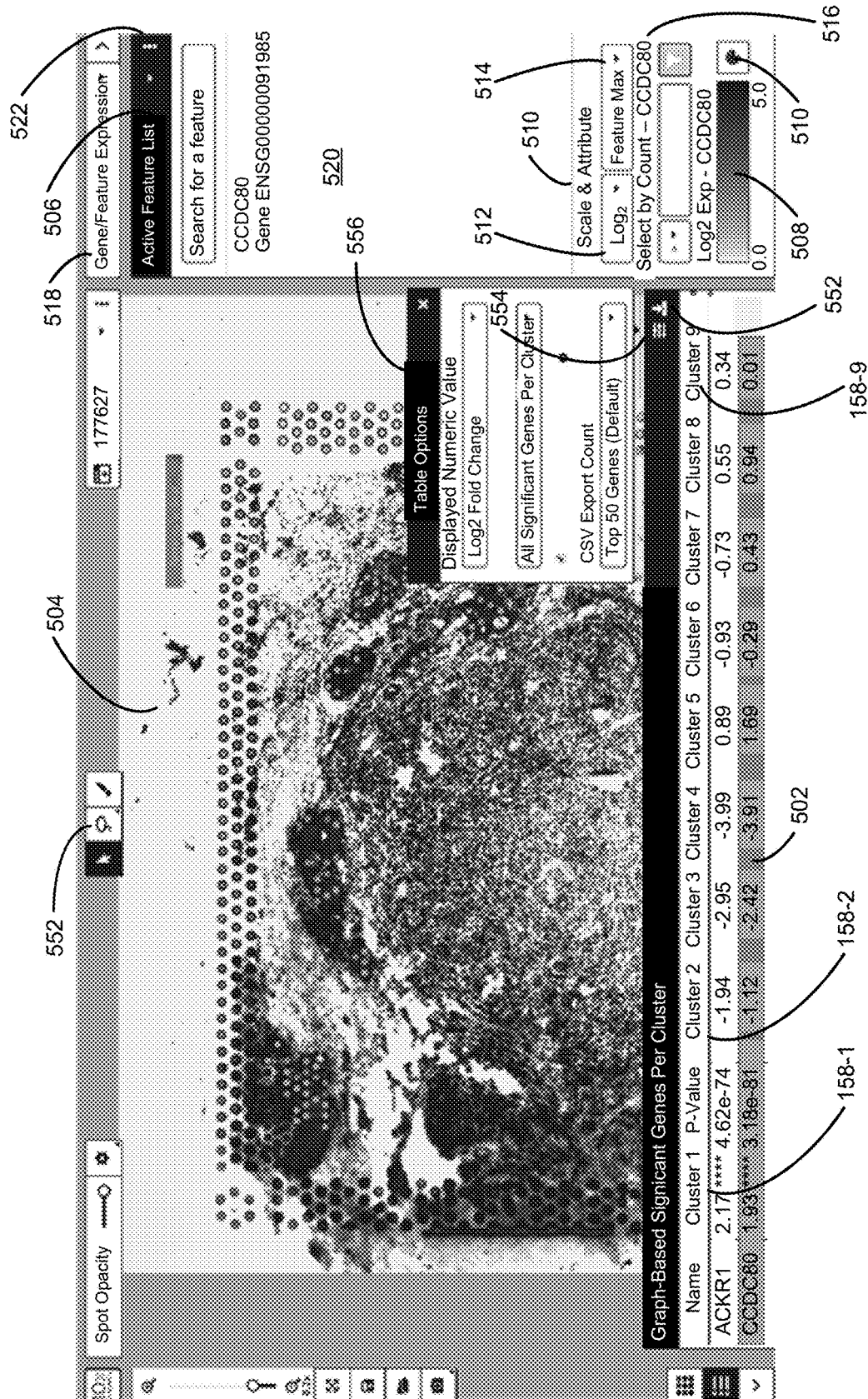
FIG. 5 illustrates an example display in which a table that comprises the differential value for each respective locus in a plurality of loci for each cluster in a plurality of clusters is displayed in a first panel while each respective probe spot in a plurality of probe spots is displayed in a second panel in accordance with some embodiments.
Figure 19:
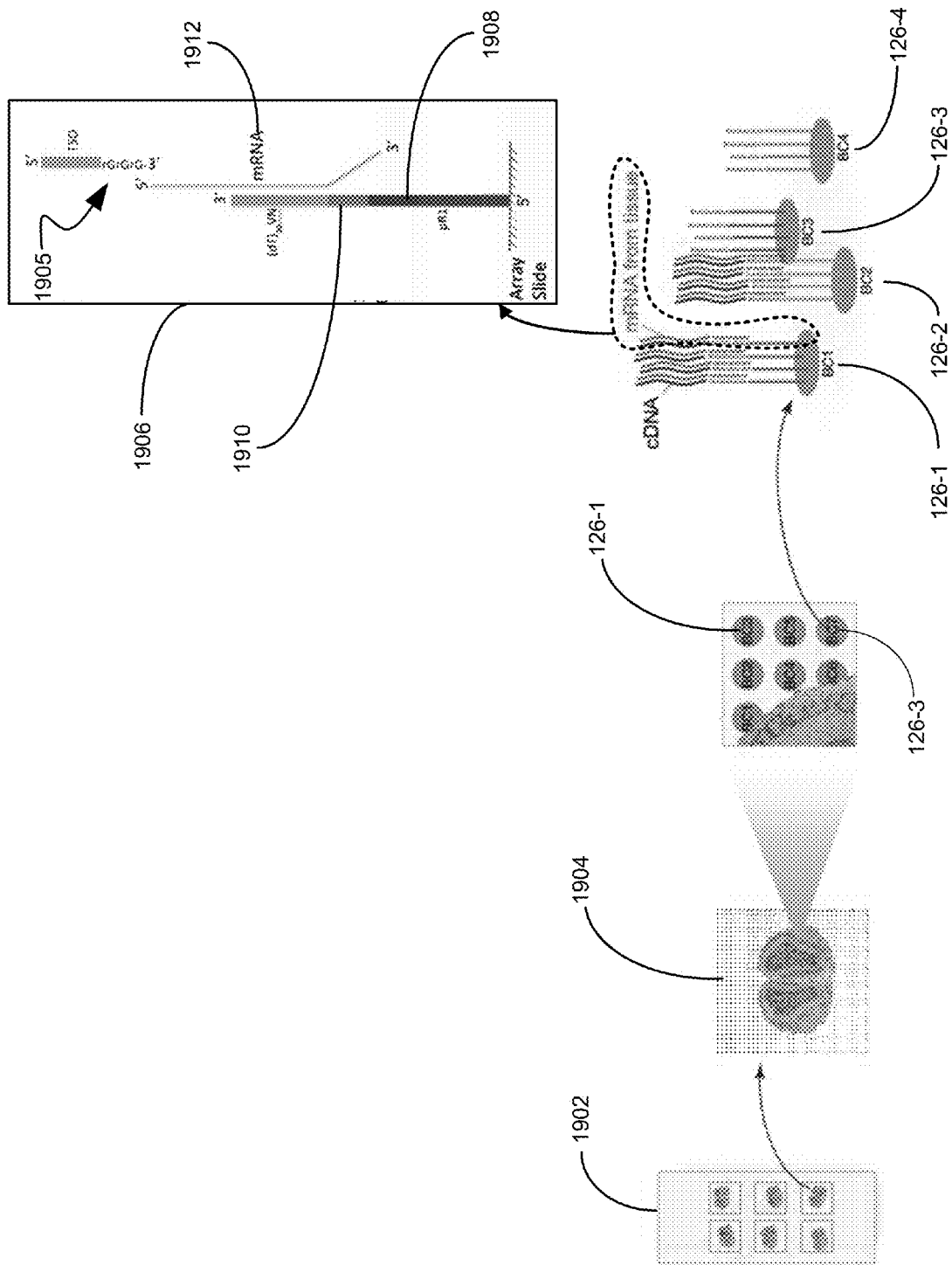
FIG. 19 illustrates details of a spatial probe spot and capture probe in accordance with an embodiment of the present disclosure.

Examples of measurement techniques for spatial probe spot based sequencing are disclosed in United States Provisional Patent Application Nos. 62/886,233, entitled "Systems and Methods for Using the Spatial Distribution of Haplotypes to Determine a Biological Condition," filed Aug. 13, 2019, and 62/938,336, entitled "Pipeline for Analysis of Analytes," filed Nov. 21, 2019, each of which is hereby incorporated by reference. As such, in some embodiments, each locus in a particular probe spot in the plurality of probe spots is barcoded with a respective barcode that is unique to the particular probe spot. FIG. 19 illustrates. In FIG. 19, a substrate 1902 containing marked capture areas (e.g., 6.5× 6.5 mm) 1904 are used where tissue sections of a biological sample are placed and imaged to form images 125. Each capture area 1904 contains a number (e.g., 5000 printed regions) of barcoded mRNA capture probes, each such region referred to herein as probe spots 126 with dimensions of 100 μm or less (e.g., 55 μm in diameter and a center-to-center distance of 200 μm or less (e.g., 100 μm). Tissue is permeabilized and mRNAs are hybridized to the barcoded capture probes 1905 located proximally and/or directly underneath. As shown in more detail in panel 1906, for a particular capture probe 1905, cDNA synthesis connects the spatial barcode 1908 and the captured mRNA 1912, and sequencing reads, in the form of UMI counts, are later overlaid with the tissue image 125 as illustrated in FIG. 5. In FIG. 5, for each respective probe spot, the corresponding UMI counts, in $\log_2$ space, mapping onto the gene CCDC80 are overlaid on the image 125. Returning to FIG. 19, for each respective probe spot 126, there are thousands or millions of capture probes 1905, with each respective capture probe 1905 containing the spatial barcode 1908 corresponding to the respective probe spot 126, and a unique UMI identifier 1910. The mRNA 1912 from the tissue sample binds to the capture probe 1905 and the mRNA sequence, along with the UMI 1910 and spatial barcode 1908 are copied in cDNA copies of the mRNA thereby ensuring that the spatial location of the mRNA within the tissue is captured at the level of probe spot 126 resolution. More details on capture probes, including spatial barcodes and unique molecular identifiers, is disclosed in U.S. Provisional Patent Application No. 62/980,073, entitled "Pipeline for Analysis of Analytes," filed Feb. 21, 2020, which is hereby incorporated by reference.

In more detail regarding tissue preparation and analysis, in some embodiments, a biological sample is harvested from a subject (e.g., via surgical biopsy, whole subject sectioning) or grown in vitro on a growth substrate or culture dish as a population of cells, and prepared for analysis as a tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick. In some embodiments, each such tissue sample is prepared by perfusing a biological sample (e.g., a tissue biopsys, a mouse, an organ, a tumor, etc.) with a buffer (e.g., 1× phosphate buffered saline) followed by dissection of a desired region. The desired region is then embedded, for example in Optimal Cutting Temperature (OCT, Fisher Healthcare, USA). The embedded sample is then subjected to a freezing bath (e.g., dry ice with prechilled ethanol) until freezing and stored (e.g., at −80° C.). From this, tissue sections (e.g., cryosections) are cut and placed onto substrates. In some embodiments, the cryosections have a thickness of between 5 μm and 100 μm. In some embodiments, the cryosections have a thickness of 10 μm.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 11, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analyzed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed (e.g., successively or independently) to obtain three-dimensional information about the biological sample. In some embodiments, tissue sections are analyzed independently, compiled into serial sections using a data sorting process, and mapped together to reconstruct the information about the biological sample.

In some embodiments, the biological sample can be prepared using formalin-fixation and paraffin-embedding (FFPE), which are established methods. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetraoxide, propidium iodide, rhodamine, safranine and/or an immunofluorescence stain.

The sample can be stained using hematoxylin and eosin (H&E) staining techniques, using Papanicolaou staining techniques, Masson's trichrome staining techniques, silver staining techniques, Sudan staining techniques, immunofluorescence (IF) staining techniques (e.g., an immunofluorescence label conjugated to an antibody), and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347(6221):543-548, 2015, the entire contents of which are incorporated herein by reference.

In some embodiments, a biological sample embedded in a hydrogel can be isometrically expanded. Isometric expansion methods that can be used include hydration, a preparative step in expansion microscopy, as described in Chen et al., Science 347(6221):543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with capture probes, as will be discussed in greater detail in a subsequent section.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

In some embodiments, the biological sample is attached to a substrate (e.g., a slide, a coverslip, a semiconductor wafer, a chip, etc.). Attachment of the biological sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

In some embodiments, a tissue sample is flash-frozen, sliced thinly (e.g., to enable visible imaging), and placed onto a substrate. In some embodiments, a tissue sample is fixed (e.g., formalin-fixed paraffin-embedded). In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., or −80° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

In some embodiments, each substrate is preprinted with barcoded capture probes (e.g., one type of barcode is printed at each probe spot in the plurality of probe spots) in at least one capture area. In some embodiments, each probe spot in the plurality of probe spots has a corresponding respective barcode, where each barcode is uniquely identifiable. The location of each barcode is known with regard to each other barcode (e.g., barcodes are spatially coded). An example of such measurement techniques for spatial probe spot based sequencing is disclosed in United States Provisional Patent Application Nos. 62/886,233, entitled "Systems and Methods for Using the Spatial Distribution of Haplotypes to Determine a Biological Condition," filed Aug. 13, 2019, and 62/938,336, entitled "Pipeline for Analysis of Analytes," filed Nov. 21, 2019, each of which is hereby incorporated by reference.

In some embodiments, the substrate includes at least one capture area (e.g., location preprinted with barcoded capture probes), where each capture area includes a respective plurality of preprinted spots of barcoded capture probes. In some embodiments, a substrate includes at least 2 capture areas, at least 3 capture areas, at least 4 capture areas, at least 5 capture areas, at least 6 capture areas, at least 7 capture areas, or at least 8 capture areas. In some embodiments, each capture area is further identified by a respective plurality of fiduciary dots (e.g., preprinted in a pattern, such as a rectangle, around the corresponding capture area).

Subsequently, one or more sections of tissue are imaged (e.g., with a light microscope) on the substrate. In some embodiments, for each tissue section, the resulting image files are stored in persistent memory (e.g., for input into a visualization module). In some embodiments, the plurality of fiduciary dots corresponding to a respective capture area is aligned across the one or more resulting image files (e.g., to improve alignment of the probe spots across the resulting image files). Fiduciary dots are stationary with respect to a substrate. In some embodiments, fiduciary dots are used as described by Lee et al. 2012, "Using fixed fiduciary markers for stage drift correction," Opt Express 20(11): 12177-12183.

After the tissue is imaged, in some embodiments, the tissue itself is permeabilized to permit each respective set of capture probes to penetrate cell membranes and bind to RNA from respective cells in the tissue that are located above each probe spot. See, for example, Maniatis, 2019, "Spatiotemporal Dynamics of Molecular Pathology in Amyotrophic Lateral Sclerosis," Science 364(6435), pp. 89-93, which is hereby incorporated by reference.

In some embodiments, a biological sample is permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference. Any suitable method for sample permeabilization can generally be used in connection with the samples described herein.

In some embodiments, where a diffusion-resistant medium is used to limit migration of analytes or other species during the analytical procedure, the diffusion-resistant medium can include at least one permeabilization reagent. For example, the diffusion-resistant medium can include wells (e.g., micro-, nano-, or picowells) containing a permeabilization buffer or reagents. In some embodiments, where the diffusion-resistant medium is a hydrogel, the hydrogel can include a permeabilization buffer. In some embodiments, the hydrogel is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (e.g. hydrogel) is covalently attached to a solid substrate (e.g., an acrylated glass slide). In some embodiments, the hydrogel can be modified to both contain capture probes and deliver permeabilization reagents. For example, a hydrogel film can be modified to include spatially-barcoded capture probes. The spatially-barcoded hydrogel film is then soaked in permeabilization buffer before contacting the spatially-barcoded hydrogel film to the sample. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, where a target analyte diffuses through the permeabilization reagent/buffer and to the spatially-barcoded capture probes. In some embodiments, resolution loss may be proportional to gap thickness (e.g., the amount of permeabilization buffer between the sample and the capture probes).

In some embodiments, permeabilization solution can be delivered to a sample through a porous membrane. In some embodiments, a porous membrane is used to limit diffusive analyte losses, while allowing permeabilization reagents to reach a sample. Membrane chemistry and pore size can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, a porous membrane is sandwiched between a spatially-barcoded array and the sample, where permeabilization solution is applied over the porous membrane. The permeabilization reagents diffuse through the pores of the membrane and into the tissue.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS).

As described herein, in some embodiments, cDNA and then sequencing libraries are created from the bound RNA, and the barcoded cDNA is then removed or separated (e.g., washed) from the substrate and collected for sequencing. The sequencing libraries are run on a sequencer, and sequencing read data (e.g., genomic and/or proteomic) is generated. In some embodiments, the method then proceeds with sequencer, grouping sequence reads by barcodes and UMIs, and aligning them to genes in a transcriptome reference, after which the pipeline generates a number of files, including a feature-barcode matrix. In some such embodiments, the transcriptome reference has sequences for 10 or more genes, 25 or more genes, 50 or more genes, 500 or more genes, 750 or more genes, 1000 or more genes, 2000 or more genes, 5000 or more genes or 10000 or more genes to which each sequence read is aligned against. In some embodiments, in the feature-barcode matrix, each entry corresponds to a number of RNA molecules proximal to (e.g., on top of) a respective probe spot (e.g., each RNA molecule has been bound by a barcode corresponding to the respective probe spot) that align to a particular locus (e.g., gene feature).

Figure 9A:
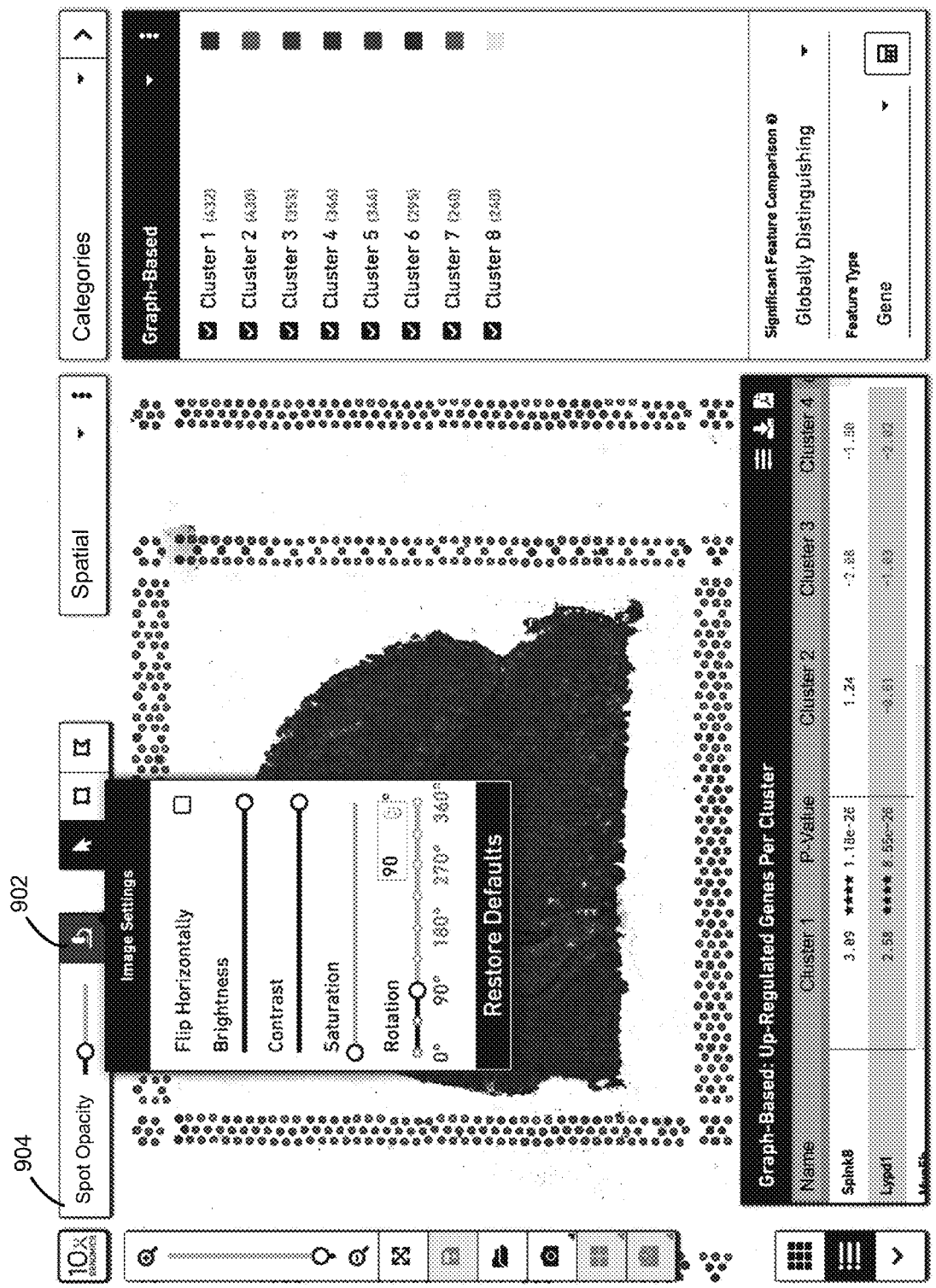
FIGS. 9A and 9B collectively illustrate examples of the image settings available for fine-tuning the visualization of the probe spot localizations, in accordance with some embodiments of the present disclosure.
Figure 9B:
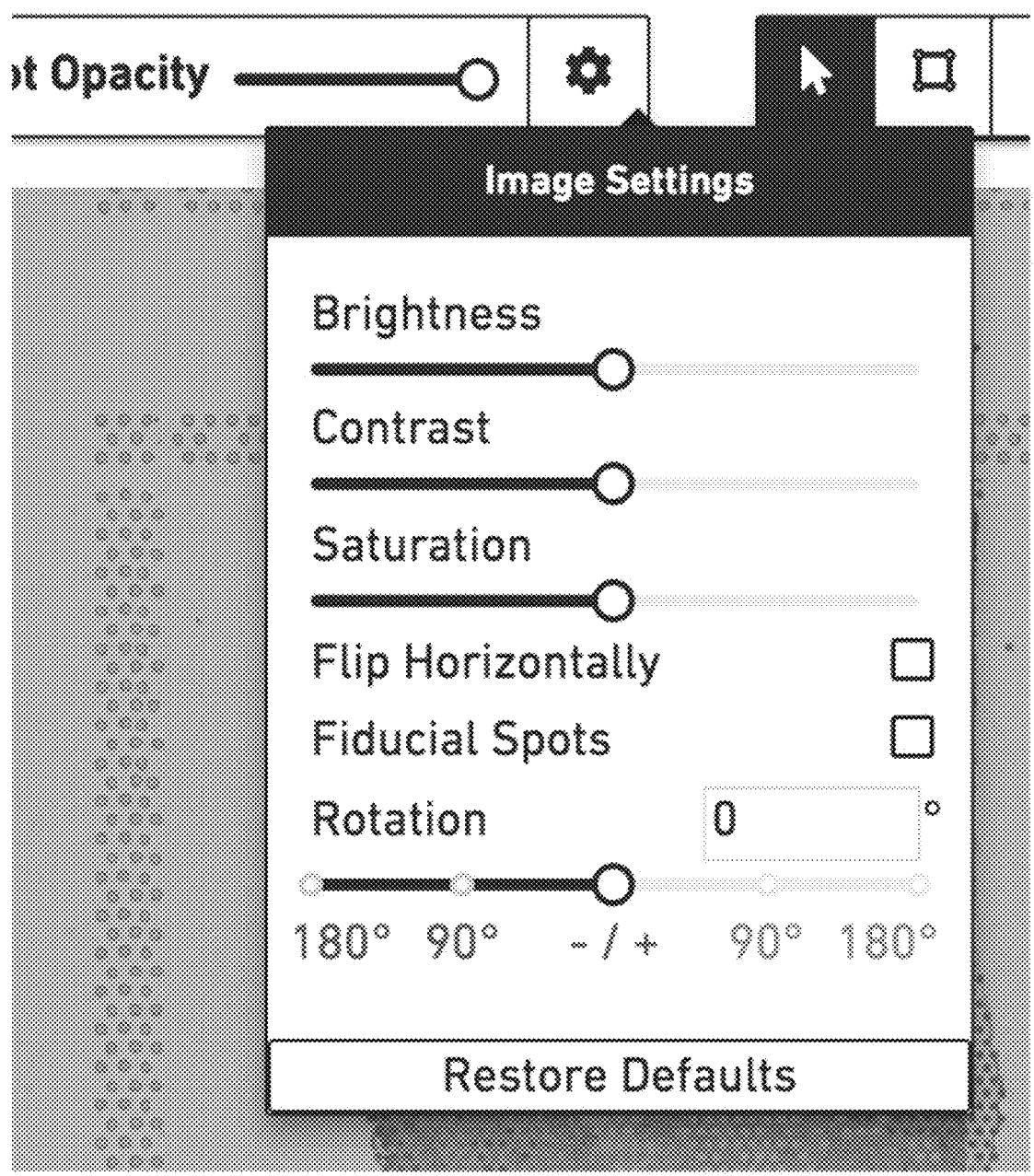
Figure 14:
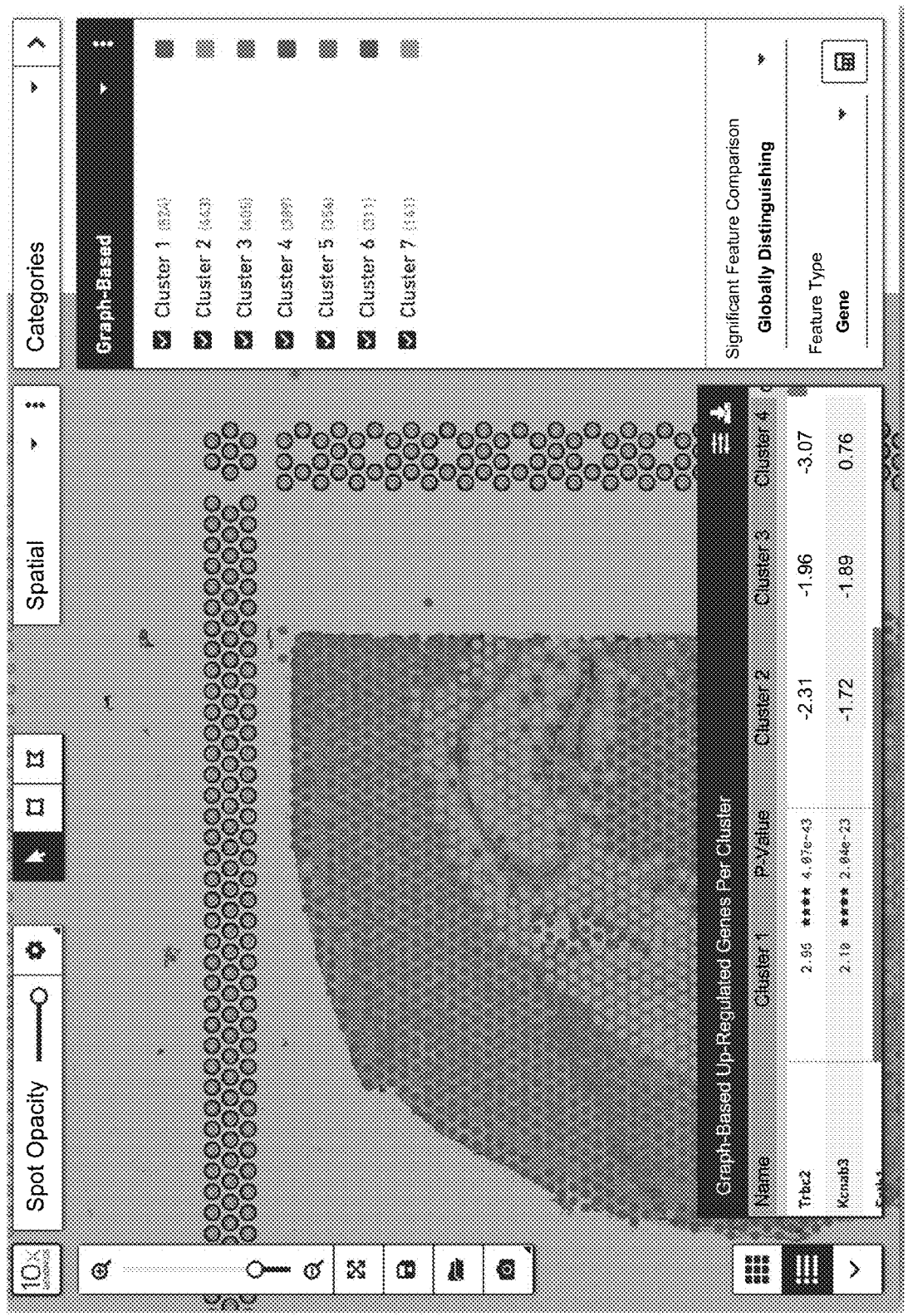
FIG. 14 illustrates black circles that approximate the sizes of the fiduciary markers superimposed on an image, where the image includes visible spots in the locations of the fiduciary markers on the substrate, and thus alignment of the black circles with the visible spots provide a measure of confidence that the barcoded spots are in the correct position relative to the image, in accordance with and embodiment of the present disclosure.

In some embodiments, each capture area of an image 125 is indicated (e.g., outlined) by a plurality of printed fiduciary dots (e.g., to identify the location of each capture area). In some embodiments, each plurality of printed fiduciary dots (e.g., dots 706 in FIG. 7) is printed into a corresponding rectangle outlining each capture area. The fiduciary positions are stored in the discrete attribute value dataset 120 (e.g., a .cloupe file) as an additional projection, akin to the other spots in a .cloupe dataset. These fiduciary positions are viewable for spatial datasets by selecting "Fiduciary Spots" from the Image Settings panel, discussed herein, as shown in FIG. 9B. When selected, circles, or other closed-form geometric indicia such as rectangles stars, etc., that approximate the sizes of the fiduciary markers are superimposed on the image. Since the substrate creation process leaves visible spots in the locations of the fiduciary markers it follows that these fiduciary locations should ideally line up with the markers visible in the image, as shown for example in FIG. 14. When they do, this provides confidence that the barcoded spots are in the correct position relative to the image. When they do not, they should prompt a user to attempt to realign the image. In some embodiments, fiduciary spots will appear as a single color of spots, or two colors of spots: the corner spots and remaining frame spots, atop the image. In some embodiments, fiduciary spots are toggleable in image settings.

In some embodiments, the discrete attribute value 124 of each locus 122 in a particular probe spot 126 in the plurality of probe spots is determined in conjunction with probe spot 126 spatial identity on a substrate. In the case where each probe spot 126 is a probe spot and each locus is an mRNA that maps to a particular gene, such embodiments provide the ability to explore the heterogeneity between probe spots, which is one form of pattern analysis afforded by the systems and methods of the present disclosure. In some such embodiments, because mRNA abundance is measured, it is possible that the mRNA abundance in the probe spot sample varies vastly from probe spot to probe spot. As such, the disclosed systems and methods enable the profiling of which genes are being expressed and at what levels in each of the probe spots and to use these gene profiles (records of discrete attribute values 124), or principal components derived therefrom, to cluster probe spots and identify sets of related probe spots. For instance, the disclosed systems and methods permit the identification of similar gene profiles in different regions of tissue, different organs, or with regard to other sources of probe spot heterogeneity.

As such, in some embodiments, each locus 122 associated with a corresponding probe spot represents one or more mRNA (e.g., one or more mRNAs that map to a gene in a reference genome for the subject from which the tissue was sampled) and the discrete attribute value 124 is a number of copies of the mRNA that have been measured in each probe spot.

In some such embodiments, the discrete attribute value dataset 120 includes discrete attribute values for 5 or more, 10 or more, 25 or more, 35 or more, 50 or more, 100 or more, 250 or more 500 or more, 1000 or more, 3000 or more, 5000 or more, 10,000 or more, or 15,000 or more different mRNAs, in each probe spot of each image 125 of each spatial projection 121 represented by the dataset. In some embodiments, each such mRNA represents a different gene and thus the discrete attribute value dataset 120 includes discrete attribute values for 5 or more, or more, 25 or more, 35 or more, 50 or more, 100 or more, 250 or more, 500 or more, 1000 or more, 3000 or more, 5000 or more, 10,000 or more, or 15,000 or more different genes in each probe spot of each image 125 of each spatial projection 121 represented by the dataset. In some embodiments, each such mRNA represents a different gene and the discrete attribute value dataset 120 includes discrete attribute values for between 5 and 20,000 different genes, or variants of different genes or open reading frames of different genes, in each probe spot of each image 125 of each spatial projection 121 represented by the dataset. More generally, in some such embodiments, the discrete attribute value dataset 120 includes discrete attribute values for 5 or more, 10 or more, 25 or more, 35 or more, 50 or more, 100 or more, 250 or more 500 or more, 1000 or more, 3000 or more, 5000 or more, 10,000 or more, or 15,000 or more different analytes, in each probe spot of each image 125 of each spatial projection 121 represented by the dataset, where each such analyte is a different gene, protein, cell surface feature, mRNA, intracellular protein, metabolite, V(D)J sequence, immune cell receptor, or perturbation agent. For general disclosure on how such analytes are spatially quantified, see, U.S. Provisional Patent Application No. 62/980,073, entitled "Pipeline for Analysis of Analytes," filed Feb. 21, 2020, which is hereby incorporated by reference. For general disclosure on how ATAC is spatially quantified using, for example clustering and/or t-SNE (where such cluster and/or t-SNE plots can be displayed in linked windows), see, United States Publication No. US-2020105373-A1 entitled "Systems and Methods for Cellular Analysis Using Nucleic Acid Sequencing" which is hereby incorporated by reference. For general disclosure on how V(D)J sequences are spatially quantified using, for example clustering and/or t-SNE (where such cluster and/or t-SNE plots can be displayed in linked windows), see, U.S. patent application Ser. No. 15/984,324, entitled "Systems and Methods for Clonotype Screening," filed May 19, 2018, which is hereby incorporated by reference.

In some embodiments, mRNA for more than 50, more than 100, more than 500, or more 1000 different genetic loci are localized to a single probe spot, and for each such respective genetic loci, one or more UMI are identified, meaning that there were one or more mRNA genetic loci encoding the respective genetic loci. In some embodiments, more than ten, more than one hundred, more than one thousand, or more than ten thousand UMI for a respective genetic loci are localized to a single probe spot.

In some embodiments, the discrete attribute value dataset 120 includes discrete attribute values for the mRNAs of 500 or more probe spots, 5000 or more probe spots, 100,000 or more probe spots, 250,000 or more probe spots, 500,000 or more probe spots, 1,000,000 or more probe spots, 10 million or more probe spots, or 50 million or more probe spots for each image 125 of each spatial projection 121 within the discrete attribute value dataset 120. In some such embodiments, each such discrete attribute value is the count of the number of unique UMI that map to a corresponding genetic loci within a corresponding probe spot.

In some embodiments, the file size of the native image 125 is between 0.5 gigabyte and gigabytes. In some embodiments, the file size of the native image 125 is between 0.5 gigabyte and 25 gigabytes. In some embodiments, the native image includes between 1 million and 25 million pixels. In some embodiments, each probe spot is represented by five or more, ten or more, 100 or more, 1000 or more contiguous pixels in a native image 125. In some embodiments, each probe spot is represented by between 1000 and 250,000 contiguous pixels in a native image 125. In some embodiments, each native image 125 is in any file format including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CDS, CPT, PSD, PSP, XCF, PDN, CGM, SVG, PostScript, PCT, WMF, EMF, SWF, XAML, and/or RAW.

In some embodiments, an image is obtained in any electronic color mode, including but not limited to grayscale, bitmap, indexed, RGB, CMYK, HSV, lab color, duotone, and/or multichannel. In some embodiments, the image is manipulated (e.g., stitched, compressed and/or flattened). In some embodiments, an image size is between 1 KB and 1 MB, between 1 MB and GB, between 0.5 GB and 5 GB, between 5 GB and 10 GB, or greater than 10 GB. In some embodiments, the image includes between 1 million and 25 million pixels. In some embodiments, each capture spot is represented by five or more, ten or more, 100 or more, 1000 or more contiguous pixels in an image. In some embodiments, each capture spot is represented by between 1000 and 250,000 contiguous pixels in a native image 125.

In some embodiments, an image is represented as an array (e.g., matrix) comprising a plurality of pixels, such that the location of each respective pixel in the plurality of pixels in the array (e.g., matrix) corresponds to its original location in the image. In some embodiments, an image is represented as a vector comprising a plurality of pixels, such that each respective pixel in the plurality of pixels in the vector comprises spatial information corresponding to its original location in the image.

In some embodiments, an image 125 is acquired using a Nikon Eclipse Ti2 with brightfield and fluorescence capacity (TRITC) or an ImageXpress Nano Automated Cell Imaging System or equivalent. In some embodiments an image 125 is acquired with a microscope having a 4× (Plan APO k; NA 0.20), 10× (Plan APO k; NA 0.45), or 20× (Plan APO k; NA 0.75) objective lens or equivalent.

In some embodiments, an image 125 is a color image (e.g., 3×8 bit, 2424×2424 pixel resolution). In some embodiments, an image 125 is a monochrome image (e.g., 14 bit, 2424×2424 pixel resolution).

In some embodiments, an image is acquired using transmission light microscopy. In some embodiments, the biological sample is stained prior to imaging using, e.g., fluorescent, radioactive, chemiluminescent, calorimetric, or colorimetric detectable markers. In some embodiments, the biological sample is stained using live/dead stain (e.g., trypan blue). In some embodiments, the biological sample is stained with Haemotoxylin and Eosin, a Periodic acid-Schiff reaction stain (stains carbohydrates and carbohydrate rich macromolecules a deep red color), a Masson's trichrome stain (nuclei and other basophilic structures are stained blue, cytoplasm, muscle, erythrocytes and keratin are stained bright-red, collagen is stained green or blue, depending on which variant of the technique is used), an Alcian blue stain (a mucin stain that stains certain types of mucin blue, and stains cartilage blue and can be used with H&E, and with van Gieson stains), a van Gieson stain (stains collagen red, nuclei blue, and erythrocytes and cytoplasm yellow, and can be combined with an elastin stain that stains elastin blue/black), a reticulin stain, an Azan stain, a Giemsa stain, a Toluidine blue stain, an isamin blue/eosin stain, a Nissl and methylene blue stain, a sudan black and osmium stain, and/or an immunofluorescence (IF) stain (e.g., an immunofluorescence label conjugated to an antibody).

In some embodiments, the discrete attribute value 124 for a given locus 122 for a given probe spot 126 in a given image 125 is a number in the set $\{0, 1, \ldots, 100\}$. In some embodiments, the discrete attribute value 124 for a given locus 122 for a given probe spot 126 in a given image 125 is a number in the set $\{0, 1, \ldots, 50\}$. In some embodiments, the discrete attribute value 124 for a given locus 122 for a given probe spot 126 in a given image 125 is a number in the set $\{0, 1, \ldots, 30\}$. In some embodiments, the discrete attribute value 124 for a given locus 122 for a given probe spot 126 in a given image 125 is a number in the set $\{0, 1, \ldots, N\}$, where N is a positive integer.

In some such embodiments, the discrete attribute value dataset 120 includes discrete attribute values for 25 or more, 50 or more, 100 or more, 250 or more, 1000 or more, 3000 or more, 5000 or more, 10,000 or more, or 15,000 or more loci 122 in each probe spot 126 in each image 125 in each spatial projection 121 represented by the dataset. In some such embodiments, the discrete attribute value dataset 120 includes discrete attribute values 124 for the loci of 500 or more probe spots, 5000 or more probe spots, 100,000 or more probe spots, 250,000 or more probe spots, 500,000 or more probe spots, 1,000,000 or more probe spots, 10 million or more probe spots, or 50 million or more probe spots for each image 125 of each spatial projection 121 in the discrete attribute value dataset 120.

In some such embodiments, the discrete attribute value dataset 120 includes discrete attribute values for 50 or more, 100 or more, 250 or more, 500 or more, 1000 or more, 3000 or more, 5000 or more, 10,000 or more, or 15,000 or more analytes in each probe spot 126 in each image 125 in each spatial projection 121 represented by the dataset. In some such embodiments, the discrete attribute value dataset 120 includes discrete attribute values 124 for the analytes of or more probe spots, 100 or more probe spots, 250 or more probe spots, 500 or more probe spots, 5000 or more probe spots, 100,000 or more probe spots, 250,000 or more probe spots, 500,000 or more probe spots, 1,000,000 or more probe spots, 10 million or more probe spots, or million or more probe spots for each image 125 of each spatial projection 121 in the discrete attribute value dataset 120.

As the above ranges indicate, the systems and methods of the present disclosure support very large discrete attribute value datasets 120 that may have difficulty being stored in the persistent memory 112 of conventional devices due to persistent memory 112 size limitations in conventional devices. Moreover, the systems and methods of the present disclosure are designed for data in which the sparsity of the dataset is significantly more than twenty percent (e.g., at least 40% of the values in the dataset are zero, at least 50% of the values in the dataset are zero, at least 60% of the values in the dataset are zero, at least 70% of the values in the dataset are zero, at least 80% of the values in the dataset are zero, or at least 90% of the values in the dataset are zero). The number of zero-valued elements divided by the total number of elements (e.g., m×n for an m×n matrix) is called the sparsity of the matrix (which is equal to 1 minus the density of the matrix. In the case where the data stored in the discrete attribute value dataset 120 is mRNA expression data, where each locus 122 represents a particular mRNA, while there are approximately twenty thousand genes in the human genome, most genes are not being expressed in a probe spot at any given time. Thus, it is expected that such data will have a sparsity approaching two percent in many instances. Thus, advantageously, to address the size constraints of the persistent memory (e.g., magnetic drives or solid-state drives) 112 limitations of conventional computers, in some embodiments, the discrete attribute value dataset 120 is represented in a compressed sparse matrix representation that may be searched both on a locus 122 basis and on a probe spot 126 basis. To accomplish this, the discrete attribute value dataset 120 redundantly represents the corresponding discrete attribute value 124 for each locus 122 in a plurality of loci for each respective probe spot 126 in a plurality of probe spots of an image 125 in a spatial projection 121 in both a compressed sparse row format and a compressed sparse column format in which loci for a respective probe spot that have a null discrete attribute data value are optionally discarded.

In some embodiments, the average density of the gene barcode matrices that are used in the systems and methods of the present disclosure are on the order of two percent. Thus, if the loci (e.g., genes) were viewed as a dense matrix, then only two percent of them would have data that is not zero. With a sparse matrix, all the zeroes are discarded. Therefore, the sparse matrix allows the dataset to fit in persistent memory 112. However, with the typical discrete attribute value datasets 120 of the present disclosure, the memory footprint is still too high once the data for half a million probe spots 126 or more is used. For this reason, both the row-oriented and column-oriented spare-matrix representations of the data are stored in persistent memory 112 in some embodiments in compressed blocks (e.g., bgzf blocks) to support quick differential-expression analysis, which requires examination of the data (e.g., the discrete attribute values of loci) for individual probe spots. In the case of the locus "gene 3," access to the discrete attribute data for gene 3 works by looking at the address in the dataset for gene 3, which thereby identifies the block in which the data for gene 3 resides. As such, when doing differential expression for a subset of the probe spots in the discrete attribute value dataset 120, the address of the individual probe spot is first needed.

Accordingly, in some embodiments, the discrete attribute value dataset 120 is stored in compressed sparse row (CSR) format. Here the term "compressed sparse row" is used interchangeably with the term "compressed sparse column" (CSC) format. The CSR format stores a sparse m×n matrix M in row form using three (one-dimensional) arrays (A, IA, JA). Here, NNZ denotes the number of nonzero entries in M (note that zero-based indices shall be used here) and the array A is of length NNZ and holds all the nonzero entries of M in left-to-right top-to-bottom ("row-major") order. The array IA is of length m+1. It is defined by this recursive definition:

$IA[0]=0;$ $IA[i]=IA[i-1]+$(number of nonzero elements on the $(\underline{i}-1)^{th}$ row in the original matrix).

Thus, the first m elements of IA store the index into A of the first nonzero element in each row of M, and the last element IA[m] stores NNZ, the number of elements in A, which can be also thought of as the index in A of first element of a phantom row just beyond the end of the matrix M. The values of the $i^{th}$ row of the original matrix is read from the elements A[IA[i]] to A[IA[i+1]−1] (inclusive on both ends), e.g., from the start of one row to the last index just before the start of the next.

The third array, JA, contains the column index in M of each element of A and hence is of length NNZ as well.

For example, the matrix M $$\begin{pmatrix} 0 & 0 & 0 & 0 \\ 5 & 8 & 0 & 0 \\ 0 & 0 & 3 & 0 \\ 0 & 6 & 0 & 0 \end{pmatrix}$$

is a 4×4 matrix with 4 nonzero elements, hence
A=[5 8 3 6]
IA=[0 0 2 3 4]
JA=[0 1 2 1]

In one implementation of the matrix M above, each row represents a different probe spot 126 and each element of a given row represents a different locus 122 associated with the different probe spot. Further, the value at a given matrix element represents the discrete attribute value for the locus 124.

In some embodiments, the discrete attribute value dataset 120 is also stored in compressed sparse column (CSC or CCS) format. A CSC is similar to CSR except that values are read first by column, a row index is stored for each value, and column pointers are stored. For instance, CSC is (val, row_ind, col_ptr), where val is an array of the (top-to-bottom, then left-to-right) non-zero values of the matrix; row_ind is the row indices corresponding to the values; and, col_ptr is the list of val indexes where each column starts.

Figure 4:
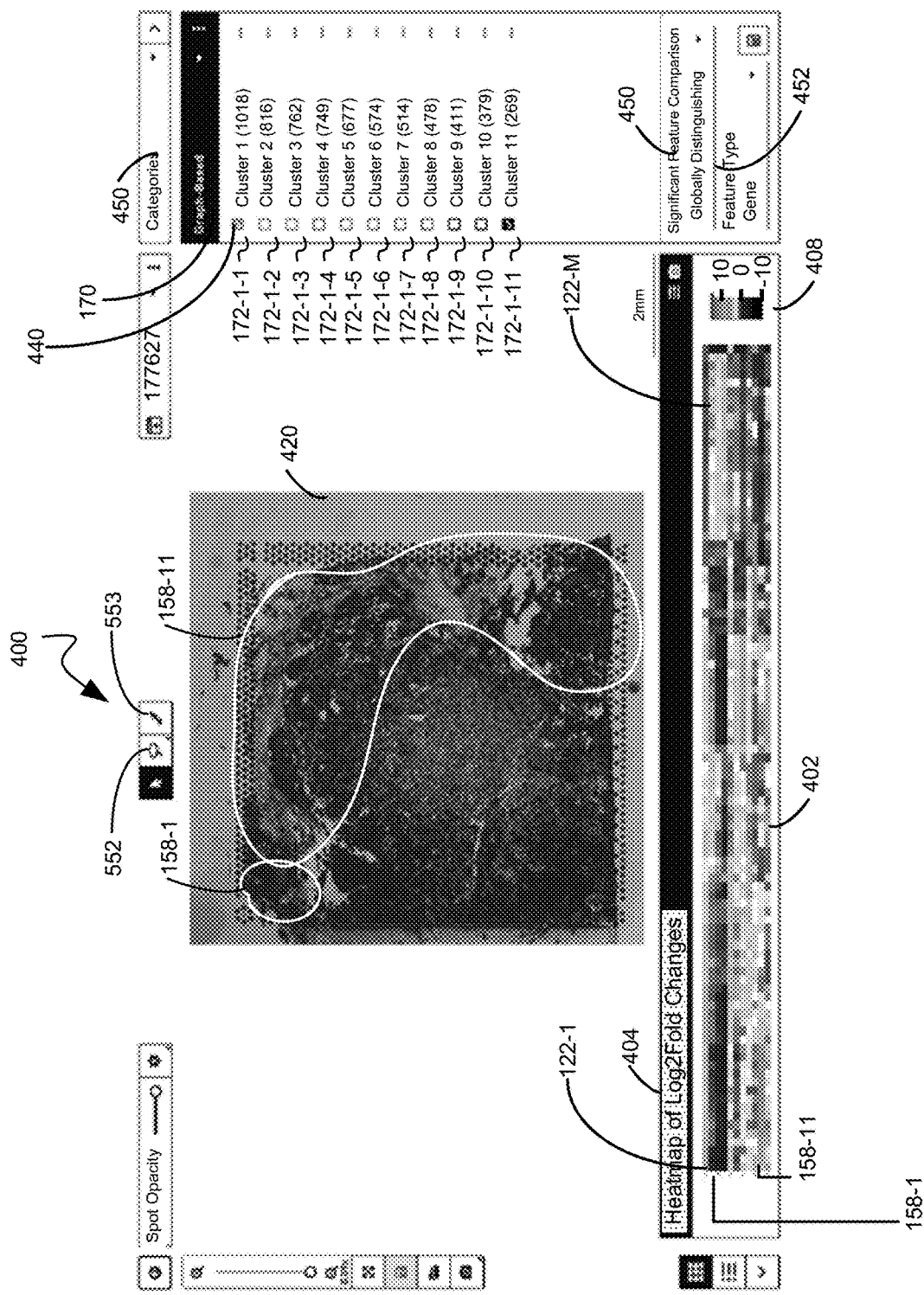
FIG. 4 illustrates an example display in which a heat map that comprises a representation of the differential value for each respective locus in a plurality of loci for each cluster in a plurality of clusters is displayed in a first panel while each respective probe spot in a plurality of probe spots is displayed in a second panel in accordance with some embodiments.

In addition to redundantly representing the corresponding discrete attribute value 124 for each locus 122 in a plurality of loci for each respective probe spot 126 in a plurality of probe spots for a given image 125 in a given spatial project 121 in the discrete attribute value dataset 120 in both a compressed sparse row format and a compressed sparse column format, the discrete attribute value dataset 120 is compressed in accordance with a blocked compression algorithm. In some such embodiments, this involves compressing the A and JA data structures but not the IA data structures using a block compression algorithm such as bgzf and storing this in persistent memory 112. Moreover, an index for compressed A and an index for compressed JA enable random seeks of the compressed data. In this way, although the discrete attribute value dataset 120 is compressed, it can be efficiently obtained and restored. All that needs to be done to obtain specific discrete attribute values 124 is seek to the correct block in persistent memory 112 and un-compress the block that contains the values and read them from within that block. Thus, certain operations, for example, like computing a differential heat map described below with reference to FIG. 4, is advantageously fast with the systems and methods of present disclosure because it is known ahead of time which block of compressed data the desired attribute values 124 are in. That is, the systems and methods of the present disclosure know which row that a particular sought after probe spot is from looking at the row address value of the sparse matrix, which is stored outside of the compressed values. So, all that is needed is to figure out which block has the sought after locus data and what their discrete attribute values are, the algorithm jumps to the spot in the correct block (e.g., bgzf block) that contains the data.

In some embodiments, the discrete attribute value dataset 120 represents a whole transcriptome sequencing (RNA-seq) experiment that quantifies gene expression from a probe spot in counts of transcript reads mapped to the genes. In some embodiments, a discrete attribute value dataset 120 represents a sequencing experiment in which baits are used to selectively filter and pull down a gene set of interest as disclosed, for example, in U.S. Provisional Patent Application No. 62/979,889, entitled "Capturing Targeted Genetic Targets Using a Hybridization/Capture Approach," filed Feb. 21, 2020, which is hereby incorporated by reference.

Block 206—clustering the dataset. In some embodiments, once a discrete attribute value dataset 120 is selected, e.g., using the interface illustrated in FIG. 3, the discrete attribute values 124 in the discrete attribute value dataset 120 are used by the clustering module 152 of the visualization module 119 to take the discrete attribute value dataset 120. A visualization of such clustering is illustrated in FIG. 4. In FIG. 4, the clustering results are displayed on top of the underlying image 125 in panel 420.

In some embodiments, the clustering is done prior to implementation of the disclosed methods. For instance, in some embodiments the discrete attribute value dataset 120 already includes the cluster assignments for each probe spot in the discrete attribute dataset.

Regardless of whether or not clustering is performed after retrieving the discrete attribute dataset or the discrete attribute value dataset already included cluster assignments for each probe spot, what is obtained is a corresponding cluster assignment in a plurality of clusters, of each respective probe spot in the plurality of probe spots of the discrete attribute value dataset. The corresponding cluster assignment (of each respective probe spot) is based, at least in part, on the corresponding plurality of discrete attribute values of the respective probe spot (e.g., the discrete attribute values that spatially map to the respective probe spot in the discrete attribute value dataset), or a corresponding plurality of dimension reduction components derived, at least in part, from the corresponding plurality of discrete attribute values of the respective probe spot.

In typical embodiments, principal component values stored in the discrete attribute value dataset 120 that have been computed by the method of principal component analysis using the discrete attribute values 124 of the loci 122 across the plurality of probe spots 126 of the discrete attribute value dataset 120 are used to perform cluster visualization, as illustrated in FIG. 4.

In some embodiments where there are multiple images 125 and/or multiple spatial projections, the principal components are computed using the discrete attribute values of each instance of a probe spot across each image 125 across each spatial projection 121 of the discrete attribute dataset 120. In some alternative embodiments, the principal components are computed for only a subset of the discrete attribute values of each instance of a probe spot across each image 125 across each spatial projection 121 of the discrete attribute dataset 120. For instance, in some embodiments, the principal components are computed for a select set of loci 124 (rather than all the loci) across each image 125 across each spatial projection 121 of the discrete attribute dataset 120. In some alternative embodiments, the principal components are computed for the discrete attribute values of each instance of a probe spot across each image 125 for a single spatial projection 121 of the discrete attribute dataset 120. In some alternative embodiments, the principal components are computed for the discrete attribute values of each instance of a probe spot across each image 125 across a subset of the spatial projections 121 of the discrete attribute dataset 120. In some embodiments, a user selects this subset. In some alternative embodiments, the principal components are computed for the discrete attribute values of each instance of a probe spot across a subset of the images 125 across each spatial projection 121 of the discrete attribute dataset 120. For instance, in some embodiments, a single channel (single image type) is user selected and the principal components are computed for the discrete attribute values of each instance of a probe spot across this single channel across each spatial projection 121 of the discrete attribute dataset 120.

Principal component analysis (PCA) is a mathematical procedure that reduces a number of correlated variables into a fewer uncorrelated variables called "principal components." The first principal component is selected such that it accounts for as much of the variability in the data as possible, and each succeeding component accounts for as much of the remaining variability as possible. The purpose of PCA is to discover or to reduce the dimensionality of the dataset, and to identify new meaningful underlying variables. PCA is accomplished by establishing actual data in a covariance matrix or a correlation matrix. The mathematical technique used in PCA is called eigen analysis: one solves for the eigenvalues and eigenvectors of a square symmetric matrix with sums of squares and cross products. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows (or columns) of this matrix. See, for example, Duda, Hart, and Stork, *Pattern Classification*, Second Edition, John Wiley & Sons, Inc., NY, 2000, pp. 115-116, which is hereby incorporated by reference.

In some embodiments where there are multiple images 125 and/or multiple spatial projections, principal components are not clustered but, rather the discrete attribute values of each instance of a probe spot across each image 125 across each spatial projection 121 of the discrete attribute dataset 120 are clustered instead. In some alternative embodiments, only a subset of the discrete attribute values of each instance of a probe spot across each image 125 across each spatial projection 121 of the discrete attribute dataset 120 are clustered. For instance, in some embodiments, the discrete attribute values for a select set of loci 124 (rather than all the loci) across each image 125 across each spatial projection 121 of the discrete attribute dataset 120 are clustered. In some alternative embodiments, the discrete attribute values of each instance of a probe spot across each image 125 for a single spatial projection 121 of the discrete attribute dataset 120 are clustered. In some alternative embodiments, the discrete attribute values of each instance of a probe spot across each image 125 across a subset of the spatial projections 121 of the discrete attribute dataset 120 are clustered. In some embodiments, a user selects this subset. In some alternative embodiments, the discrete attribute values of each instance of a probe spot across a subset of the images 125 across each spatial projection 121 of the discrete attribute dataset 120 are clustered. For instance, in some embodiments, a single channel (single image type) is user selected and the discrete attribute values of each instance of a probe spot across this single channel across each spatial projection 121 of the discrete attribute dataset 120 are clustered.

Referring to block 208, in some embodiments, the above-described clustering (e.g., of the principal component values and/or the discrete attribute values) is performed at a prior time on a remote computer system. That is, in some embodiments, the cluster assignment of each probe spot 126 was already performed prior to storing the discrete attribute value dataset 120. In such embodiments, the discrete attribute value dataset 120 includes the cluster assignment 158 of each probe spot, as illustrated in FIG. 1B.

In some embodiments, the cluster assignment of each probe spot 126 is not performed prior to storing the discrete attribute value dataset 120 but rather all the principal component analysis computation of the principal component values 164 is performed prior to storing the discrete attribute value dataset 120. In such embodiments, clustering is performed by the clustering module 152 of FIG. 1A.

For clustering in accordance with one embodiment of the systems and methods of the present disclosure, regardless at what stage it is performed, consider the case in which each probe spot 126 is associated with ten loci 122. Each of the ten loci represents a different feature under study, such as a different antibody, a different region of a reference genome, etc. In such instances, each probe spot 126 can be expressed as a vector:

$$\vec{X}_{10} = \{x_1, x_2, x_3, x_4, x_5, x_6, x_7, x_8, x_9, x_{10}\}$$

where $X_i$ is the discrete attribute value 124 for the locus i 124 associated with the probe spot 126 in a given spatial projection. Thus, consider the case where the discrete attribute dataset comprises a single image and a single projection and there are one thousand probe spots in this single image. In this case, 1000 vectors are defined. Now, consider the case where the discrete attribute dataset comprises a two images in each of three projection and there are one thousand probe spots in each of the images. In this case, 3×1000, or 3000 vectors are defined. Those probe spots 126 that exhibit similar discrete attribute values across the set of loci 122 of the dataset 102 will tend to cluster together. For instance, in the case where each probe spot 126 is an individual cell, the loci 122 correspond to mRNA mapped to individual genes within such individual cells, and the discrete attribute values 124 are mRNA counts for such mRNA. It is the case in some embodiments that the discrete attribute value dataset 120 includes mRNA data from one or more probe spot types (classes, e.g., diseased state and non-diseased state), two or more probe spot types, or three or more probe spot types. In such instances, it is expected that probe spots of like type will tend to have like values for mRNA across the set of loci (mRNA) and therefor cluster together. For instance, if the discrete attribute value dataset 120 includes class a: probe spots from subjects that have a disease, and class b: probe spots from subjects that do not have a disease, an ideal clustering classifier will cluster the discrete attribute value dataset 120 into two groups, with one cluster group uniquely representing class a and the other cluster group uniquely representing class b.

For clustering in accordance with another embodiment of the systems and methods of the present disclosure, regardless at what stage it is performed, consider the case in which each probe spot 126 is associated with ten principal component values that collectively represent the variation in the discrete attribute values of a large number of loci 122 of a given probe spot with respect to the discrete attribute values of corresponding loci 122 of other probe spots in the dataset. This can be for a single image 125, across all or a subset of images in a single spatial projection 121, or across all or a subset of the images in all or a subject of a plurality of spatial projections 125 in a discrete attribute value dataset 120. In such instances, each probe spot 126 can be expressed as a vector:

$$\vec{X}_{10} = \{x_1, x_2, x_3, x_4, x_5, x_6, x_7, x_8, x_9, x_{10}\}$$

where $X_i$ is the principal component value 164 $i$ associated with the probe spot 126. Thus, if there are one thousand probe spots 126 per image, a total of one thousand vectors are defined across the images. The vectors representing those probe spots 126 that exhibit similar discrete attribute values across the set of principal component values 164 will tend to cluster together. It is the case, in some embodiments, that the discrete attribute value dataset 120 includes mRNA data from one or more probe spot types (e.g., diseased state and non-diseased state), two or more probe spot types, or three or more probe spot types. In such instances, it is expected that probe spots of like type will tend to have like values for mRNA across the set of loci (mRNA) and therefor cluster together. For instance, if the discrete attribute value dataset 120 includes class a: probe spots from subjects that have a disease, and class b: probe spots from subjects that have a disease, an ideal clustering classifier will cluster the discrete attribute value dataset 120 into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar." An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the dataset that extremize the criterion function are used to cluster the data. See page 217 of Duda 1973. Criterion functions are discussed in Section 6.8 of Duda 1973.

More recently, Duda et al., *Pattern Classification*, Second edition, John Wiley & Sons, Inc. New York, which is hereby incorporated by reference, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, Cluster analysis (Third Edition), Wiley, New York, N.Y.; and Backer, 1995, *Computer Assisted Reasoning in Cluster Analysis*, Prentice Hall, Upper-Saddle River, N.J. Referring to blocks 210-212, particular exemplary clustering techniques that can be used in the systems and methods of the present disclosure to cluster a plurality of vectors, where each respective vector in the plurality of vectors comprises the discrete attribute values 124 across the loci 122 of a corresponding probe spot 126 (or principal components derived therefrom) includes, but is not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

Thus, in some embodiments, the clustering module 152 clusters the discrete attribute value dataset 120 using the discrete attribute value 124 for each locus 122 in the plurality of loci for each respective probe spot 126 in the plurality of probe spots, or principal component values 164 derived from the discrete attribute values 124, across one or more images in one or more spatial projections in the discrete attribute value dataset 120 thereby assigning each respective probe spot 126 in the plurality of probe spots to a corresponding cluster 158 in a plurality of clusters and thereby assigning a cluster attribute value to each respective probe spot in the plurality of probe spots of each image used in the analysis.

Referring to block 214, in one embodiment of the present disclosure, k-means clustering is used. The goal of k-means clustering is to cluster the discrete attribute value dataset 120 based upon the principal components or the discrete attribute values of individual probe spots into K partitions. Referring to block 214, in some embodiments, K is a number between 2 and 50 inclusive. In some embodiments, the number K is set to a predetermined number such as 10. In some embodiments, the number K is optimized for a particular discrete attribute value dataset 120. Referring to block 216, in some embodiments, a user sets the number K using the visualization module 119.

FIG. 4 illustrates an instance in which the multichannel-aggr dataset 120, constituting data from a plurality of probe spots has been clustered into eleven clusters 158. In some embodiments, for k-means clustering, the user selects in advance how many clusters the clustering algorithm will compute prior to clustering. In some embodiments, no predetermined number of clusters is selected. Instead, clustering is performed until predetermined convergence criteria are achieved. In embodiments where a predetermined number of clusters is determined, k-means clustering of the present disclosure is then initialized with K cluster centers $\mu_1, \ldots, \mu_K$ randomly initialized in two-dimensional space. As discussed above, for each respective probe spot 126 $i$ in the dataset, a vector X is constructed of each principal component value 164 associated with the respective probe spot 126. In the case where K is equal to 10, ten such vectors $\vec{X}$ are selected to be the centers of the ten clusters. Then, each remaining vector $\vec{X}_i$, corresponding to the probe spots 126 that were not selected to be cluster centers, is assigned to its closest cluster center:

$$C_k = \left\{ n: k = \arg\min_k \left\| \vec{X}_i - \mu_k \right\|^2 \right\}$$

where $C_k$ is the set of examples closest to $\mu_k$ using the objective function:

$$J(\mu, r) = \sum_{n=1}^{N} \sum_{k=1}^{K} r_{nk} \left\| \vec{X}_i - \mu_k \right\|^2$$

where $\mu_1, \ldots, \mu_K$ are the K cluster centers and $r_{nk} \in \{0, 1\}$ is an indicator denoting whether a probe spot 126 $\vec{X}_i$ belongs to a cluster k. Then, new cluster centers $\mu_k$ are recomputed (mean/centroid of the set $C_k$):

$$\mu_k = \tfrac{1}{|C_k|} \sum \vec{X}_i$$

Then, all vectors $\vec{X}_i$, corresponding to the entities 126 are assigned to the closest updated cluster centers as before. This is repeated while not converged. Any one of a number of convergence criteria can be used. One possible convergence criteria is that the cluster centers do not change when recomputed. The k-means clustering computes a score for each respective entity 126 that takes into account the distance between the respective entity and the centroid of the cluster 158 that the respective probe spot has been assigned. In some embodiments, this score is stored as the cluster attribute value 160 for the probe spot 126.

Once the clusters are identified, as illustrated in FIG. 4, individual clusters can be selected to display. For instance, referring to FIG. 4, affordances 440 are individually selected or deselected to display or remove from the display the corresponding cluster 158.

As illustrated in FIG. 4, in accordance with the systems and methods of the present disclosure, in typical embodiments, each respective cluster 158 in the plurality of clusters consists of a unique different subset of the second plurality of probe spots 126. Moreover, because in typical embodiments the discrete attribute value dataset 120 is too large to load into the non-persistent memory 111, in typical embodiments this clustering loads less than the entirety of the discrete attribute value dataset 120 into the non-persistent memory 111 at any given time during the clustering. For instance, in embodiments where the discrete attribute value dataset 120 has been compressed using bgzf, only a subset of the blocks of the discrete attribute value dataset 120 are loaded into non-persistent memory during the clustering of the discrete attribute value dataset 120. Once one subset of the blocks of the discrete attribute value dataset 120 have been loaded from persistent memory 112 into non-persistent memory 111 and processed in accordance with the clustering algorithm (e.g., k-means clustering), the subset of blocks of data is discarded from non-persistent memory 111 and a different subset of blocks of the discrete attribute value dataset 120 are loaded from persistent memory 112 into non-persistent memory 111 and processed in accordance with the clustering algorithm of the clustering module 152.

In some embodiments, k-means clustering is used to assign probe spots 126 to clusters 158. In some such embodiments, the k-means clustering uses as input the principal component values 164 for each probe spot 126 as the basis for clustering the probe spots into cluster. Thus, the k-means algorithm computes like clusters of probe spots from the higher dimensional data (the set of principal component values) and then after some resolution, the k-means clustering tries to minimize error. In this way, the k-means clustering provides cluster assignments 158, which are recorded in the discrete attribute value dataset 120. In some embodiments, with k-means clustering, the user decides in advance how many clusters 158 there will be. In some embodiments, feature of k-means cluster is exploited by running a series of k-means clustering runs, with each different run having a different number of clusters (a different value for K). Thus, in some embodiments, a separate k-means clustering is performed on the principal component data values 164 of each probe spot 122, ranging from two clusters to eleven clusters, with each k-means clustering identifying a separability score (e.g., a quality score) and all the results of each clustering embedded in the discrete attribute value dataset 120 from K=2 through K=11. In some such embodiments, such clustering is performed for K=2 through K=25. In some such embodiments, such clustering is performed for K=2 through K=100. The clustering that is displayed by default in such embodiments is the k-means clustering (1, N) that has the highest separability score. In FIG. 4, each cluster 158 is displayed in a different color. In other embodiments, each cluster 158 is displayed with a different dot pattern or hash pattern.

The k-means clustering algorithm described herein elucidates like clusters 158 within the data. There is no guarantee that all the clusters 158 represent physiologically significant events. In other words, a priori, it is not known what the clusters 158 mean in some instances. What is known is that the algorithm has determined that there are differences between the probe spots 126 that are being represented by different colors or different hash patterns or symbols. The systems and methods of the present disclosure provide tools for determining whether there is any meaning behind the differences between the clusters such as the heat map of panel 404.

Figure 17A:
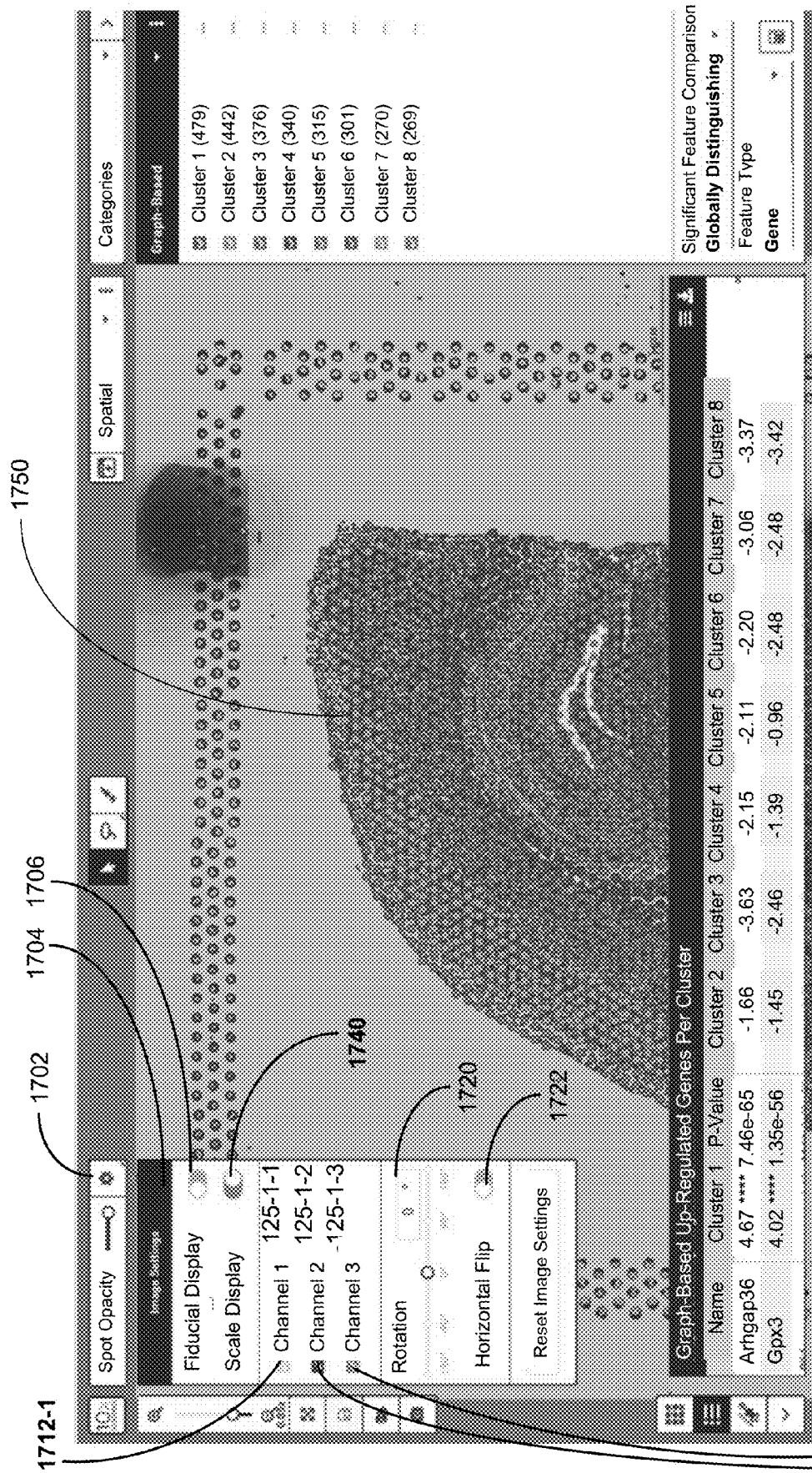
FIGS. 17A, 17B, 17C, 17D, and 17E illustrate a spatial projection of a multichannel discrete attribute dataset that includes multiple images of the same tissue sample in accordance with an embodiment of the present disclosure.

Referring to block 214, in some embodiments, of the present disclosure, rather than using k-means clustering, a Louvain modularity algorithm is used. See, Blondel et al., Jul. 25, 2008, "Fast unfolding of communities in large networks," arXiv:0803.0476v2 [physical.coc-ph], which is hereby incorporated by reference. In some embodiments, the user can choose a clustering algorithm. In some embodiments, the user can choose between at least k-means clustering and a Louvain modularity algorithm. In some embodiments, clustering the dataset comprises application of a Louvain modularity algorithm to a map, the map comprising a plurality of nodes and a plurality of edges. In such embodiments, each node in the plurality of nodes represents a probe spot in the plurality of probe spots. The coordinates in N-dimensional space of a respective node in the plurality of nodes are a set of principal components of the corresponding probe spot in the plurality of probe spots. The set of principal components is derived from the corresponding discrete attribute values of the plurality of loci for the corresponding probe spot, where N is the number of principal components in each set of principal components. An edge exists in the plurality of edges between a first node and a second node in the plurality of nodes when the first node is among the k nearest neighboring nodes of the second node in the first plurality of node, where the k nearest neighboring nodes to the second node is determined by computing a distance in the N-dimensional space between each node in the plurality of nodes, other than the second node, and the second node. In some embodiments, the distance is a Euclidean distance. In other embodiments, other distance metrics are used (e.g., Chebyshev distance, Mahalanobis distance, Manhattan distance, etc.). In typical embodiments, the nodes and the edges are not weighted for the Louvain modularity algorithm. In other words, each node and each edge receives the same weight in such embodiments Block 218—Display, in a first window, pixel values of all or apportion of an image in the one or more images of a first projection. Referring to block 218, in some embodiments, the methods continue by displaying, in a first window on the display, pixel values of all or portion of a first two-dimensional image in the one or more two-dimensional images of the first projection. This is illustrated in FIG. 17A. In FIG. 17A, the image is illustrated and those pixels corresponding to where the sample were overlayed, that is region 1750, on a substrate are shown colored against a background grey. The background grey reflects the regions where no sample was overlayed on the substrate. Each round spot in region 1750 of the image represents a probe spot.

Block 220—Overlay cluster indicia. Referring to block 220 of FIG. 2B, the method continues by displaying on the first two-dimensional image and co-aligned with the first two-dimensional image (i) first indicia for each probe spot in the plurality of probe spots that have been assigned to a first cluster in the plurality of clusters and (ii) second indicia for each probe spot in the plurality of probe spots that have been assigned to a second cluster in the plurality of clusters, thereby identifying the morphological pattern. Referring to block 222 of FIG. 2B, in some embodiments, each such cluster is assigned a different graphic or color code. Further, each respective probe spot 126 in the plurality of probe spots is coded with the different graphic or color code for the cluster the respective probe spot has been assigned. FIG. 17A illustrates. In FIG. 17A, each respective spot has been assigned to one of eight clusters based, at least in part, on the corresponding plurality of discrete attribute values of the respective probe spot, or a corresponding plurality of dimension reduction components derived, at least in part, from the corresponding plurality of discrete attribute values of the respective probe spot. The color coding, by cluster assignment, reveals morphological patterns within the underlying biological sample. For instance, in FIG. 17A, each cluster of probe spots has a distinct morphological pattern within the biological pattern. Depending on the biological sample and the nature of the expression within each cluster, such a morphological pattern can provide valuable insight into the underlying biological sample. For instance, the morphological patterns can be used to determine a disease state of the biological sample. As another example, the morphological pattern can be used to recommend a therapeutic treatment for the donor of the biological sample.

An example of the utility of the disclosed methods can be appreciated by considering the important biological question regarding whether lymphocytes have successfully infiltrated a tumor or not. Using the disclosed techniques, the lymphocytes may have different expression profiles then the tumor cells. Thus, the lymphocytes may cluster (e.g., through the clustering described above in conjunction with block 206) into the first cluster and thus each probe spot corresponding to portions of a tissue sample in which lymphocytes are present may have the first indicia cluster. The tumor cells may cluster into the second cluster and thus each probe spot in which lymphocytes are not present may have the second indicia for the second cluster. When this is the case, the morphological pattern of lymphocyte infiltration into the tumor could be documented by probe spots bearing first indicia (representing the lymphocytes) amongst the probe spots bearing second indicia (representing the tumor cells). The morphological pattern exhibited by the lymphocyte infiltration into the tumor would be associated with a favorable diagnosis whereas the inability of lymphocytes to infiltrate the tumor would be associated with an unfavorable diagnosis. Thus, in this way, the spatial relationship (morphological pattern) of cell types in heterogeneous tissue can be used to analyze tissue samples.

Another example of the utility of the disclosed methods can be appreciated by considering the important biological question regarding whether a tumor is metastasizing or to determine the overall extent of a tumor within a normal healthy tissue (e.g., even in cases where the tumor is very small and difficult to discern by conventional visual methods). Using the disclosed techniques, the cancerous cells associated with the tumor will have different expression profiles then normal cells. Thus the cancerous cells may cluster (e.g., through the clustering described above in conjunction with block 206) into a first cluster using the disclosed methods and thus each probe spot corresponding to portions of a tissue sample in which the cancerous cells are present will have the first indicia cluster. The normal cells may cluster into the second cluster and thus each probe spot corresponding to portions of the tissue sample in which cancerous cells are not present will have the second indicia for the second cluster. If this is the case, the morphological pattern of cancer cell metastatis, or the morphology of a tumor (e.g., shape and extent within a normal healthy tissue sample) can be documented by probe spots bearing first indicia (representing cancerous cells) amongst the probe spots bearing second indicia (representing normal cells).

Now that the overall functionality of the systems and methods of the present disclosure has been introduced, attention turns to additional features afforded by the present disclosure. As illustrated in FIG. 5, the lower panel 502 is arranged by rows and columns. Each row corresponds to a different locus. Each column corresponds to a different cluster. Each cell, then, illustrates the fold change (e.g., $\log_2$ fold change) of the average discrete attribute value 124 for the locus 122 represented by the row the cell is in across the probe spots 126 of the cluster represented by the column the cell is in compared to the average discrete attribute value 124 of the respective locus 122 in the probe spots in the remainder of the clusters represented by the discrete attribute value dataset 120.

The lower panel 502 has two settings. The first is a hierarchical clustering view of significant loci 122 per cluster. In some embodiments, $\log_2$ fold change in expression refers to the $\log_2$ fold value of (i) the average number of transcripts (discrete attribute value) measured in each of the probe spots of the subject cluster that map to a particular gene (locus 122) and (ii) the average number of transcripts measured in each of the probe spots of all clusters other than the subject cluster that map to the particular gene.

In some embodiments, selection of a particular locus (row) in the lower panel 502 of FIG. 5 causes the locus (feature) associated with that row to be an active feature that is posted to the active feature list 506. For instance, as illustrated in FIG. 5, the locus "CCDC80" from lower panel 502 has been selected and so the locus "CCDC80" is in the active feature list 506. The active feature list 506 is a list of all features that a user has either selected (e.g., "CCDC80") or uploaded. The expression patterns of those features are displayed in panel 504 of FIG. 5. If more than one feature is in the active feature list 506, then the expression patter that is displayed in panel 504 corresponds to a combination (measure of central tendency) of all the features. If only one feature is presented or selected in the active feature list 506, then the expression pattern that is overlayed on the native image 125 in panel 504 is the expression pattern corresponding to the selected feature. Thus, in FIG. 5, each respective probe spot in the discrete attribute value dataset 120, regardless of which cluster the probe spot is in, is illuminated with an intensity, color, or other form of display attribute that is commensurate with a number of transcripts (e.g., $\log_2$ of expression) of the single active feature CCDC80 that is present in the respective probe spot 126 in the upper panel 504.

At the bottom of the active feature list 506 there are a number of options that control how the data is visualized in the upper panel 504. The scale & attribute parameters 510 control how the expression patterns are rendered in the upper panel 504. For instance, toggle, 512 sets which scale value to display (e.g., $\log_2$, linear, log-normalized). The top right menu sets how to combine values when there are multiple features in the Active Feature List. For instance, in the case where two features (e.g., loci) have been selected for the active feature list 506, toggle 514 can be used to display, in each probe spot, the feature minimum, feature maximum, feature sum, for feature average. Thus, consider the case where features (e.g., loci) A and B are selected as the active features for the active feature list 506. In this case, selection of "feature minimum" will cause each respective probe spot to be assigned a color on the color scale that is commensurate of a minimum expression value, that is, the expression of A or the expression of B, whichever is lower. Thus, each respective probe spot is independently evaluated for the expression of A and B at the respective probe spot, and the probe spot is colored by the lowest expression value of A and B. On the other hand, toggle 514 can be used to select the maximum feature value from among the features in the active feature list 506 for each probe spot, or to sum the feature values across the features in the active feature list 506 for each probe spot or to provide a measure of central tendency, such as average, across the features in the active feature list 506 for each probe spot.

The select by count menu options 516 control how to filter the expression values displayed. For instance, the color palette 510 controls the color scale and range of values. The user can also choose to manually set the minimum and maximum of the color scale by unchecking an Auto-scale checkbox (not shown), typing in a value, and clicking an Update Min/Max button (not shown). When setting manual minimum and maximum values, spots with values outside the range, less than the minimum or greater than the maximum, are colored gray. This is particularly useful if there is a lot of noise or ambient expression of a locus or a combination of loci in the active feature list 506. Increasing the minimum value of the scale filters that noise. It is also useful to configure the scale to optimally highlight the expression of genes of interest.

In FIG. 5, color scale 508 shows the $\log_2$ expression of CCDC80 ranging from 0.0 to 5.0. In this way, a user can quickly ascertain the relative expression of a specific locus in the probe sports of the discrete attribute dataset 120. Moreover, the present disclosure is not limited to showing the $\log_2$ relative expression of a locus. In some embodiments, toggle 510 can be used to illustrate the relative expression of features in the active feature list 506 on a linear basis or a log-normalized basis. Moreover, palette 510 can be used to change the color scale 508 to other colors, as well as to set the minimum and maximum values that are displayed.

Toggle 518 is used to toggle between "Gene/Feature Expression" mode, "Categories" mode, and "Filters" mode.

In "Gene/Feature Expression" mode, the user can control the content in the mode panel 520 of the active feature list 506 by clicking on affordance 522. This allows the user to select from among a "new list" option, an "edit name" option, a "delete list" option, and an "import list" option. The "new list" option is used to create a custom list of features to visualize. The "edit name" option is used to edit the name of the active feature list. The "delete list" option is used to delete an active feature list. The "import list" option is used to import an active feature list from an external source while the "new list" option is used to create a custom list of features to visualize.

When toggle 518 is switched to "Filters" mode, the user can compose complex Boolean filters to find barcodes that fulfill selection criteria. For instance, the user can create rules based on feature counts or cluster membership and combine these rules using Boolean operators. The user can then save and load filters and use them across multiple datasets.

Panel 502 of FIG. 5 provides a tabular representation of the $\log_2$ discrete attribute values 124 in column format, whereas the heat map of FIG. 4 showed the $\log_2$ discrete attribute values 124 in rows. The user can select any respective cluster 158 by selecting the column label for the respective cluster. This will re-rank all the loci 122 such that those loci that are associated with the most significant discrete attribute value 124 in the selected cluster 158 are ranked first (e.g., in the order of the most loci have the most significant associated discrete attribute value 124). Moreover, a p-value is provided for the discrete attribute value of each locus 122 in the selected cluster to provide the statistical significance of the discrete attribute value 124 in the selected cluster 158 relative to the discrete attribute value 124 of the same locus 122 in all the other clusters 158. In some embodiments, these p-values are calculated based upon the absolute discrete attribute values 124, not the $\log_2$ values used for visualization in the heat map 402. Referring to FIG. 5 to illustrate, the locus 122 in cluster 1 that has the largest associated discrete attribute value 124, ACKR1, has a p-value of $4.62\ e^{-74}$. As illustrated in FIG. 5, this p-value is annotated with a star system, in which four stars means there is a significant difference between the selected cluster (k-means cluster 158-1 in FIG. 5) and the rest of the clusters for a given locus, whereas fewer stars means that there is a less significant difference in the discrete attribute value 124 (e.g., difference in expression) between the locus 122 in the selected cluster relative to all the other clusters. By clicking a second time on the selected cluster 158 label, the ranking of the entire table is inverted so that the locus 122 associated with the least significant discrete attribute value 124 (e.g., least expressed) is at the top of the table. Selection of the label for another cluster (e.g., cluster 158-9) causes the entire table 502 to re-rank based on the discrete attribute values 124 of the loci 122 in the probe spots that are in k-means cluster for the associated cluster associated with (e.g., cluster 158-9). In this way, the sorting is performed to more easily allow for the quantitative inspection of the difference in discrete attribute value 158 in any one cluster 158 relative to the rest of the clusters.

As illustrated by tab 552 of FIG. 5, the table of values 502 can be exported, e.g., to an EXCEL .csv file, by pressing tab 552 at which point the user is prompted to save the table as a csv (or other file format). In this way, once the user has completed their exploration of the k-means clustering, tab 552 allows the user to export the values. Moreover, the user is given control over which values to export (e.g., top 10 loci, top 20 loci, top 50 loci, top 100 loci, where "top" is from the frame of reference of the cluster the user has identified in panel 502. Thus, if the user has selected column 158-1 and "top 50 loci," the discrete attribute values 124 of the top loci in cluster 1 will be selected for exporting and what will be exported will be the discrete attribute values 124 of these 50 loci in each of the clusters of the discrete attribute value dataset (clusters 1-11 in the example dataset used for FIGS. 5 and 6). Moreover, in some embodiments, a user is able to load and save lists of loci to and from persistent storage, for instance, using panel 404.

Moreover, in some embodiments, a user is able to select probe spots using the selection tools 552. Once the probe spots are selected the user can assign the selection a category name, assign the probe spots to a particular cluster or un-assign the selected probes spots from all clusters. Further, the user can export the top loci in the selected probe spots using the affordance 552 in the manner described above for clusters 158.

Referring again to FIG. 4, the heat map 402 provides a $\log_2$ differential that is optimal where the discrete attribute value 124 represents the number of transcripts that map to a given probe spot in order to provide a sufficient dynamic range over the number of transcripts seen per gene in the given probe spot. In some embodiments, $\log_{10}$ differential expression is used instead of $\log_2$. However, it is expected that $\log_{10}$ does not provide sufficient dynamic range for appropriate visualization of the relative expression of gene data in the k-means clusters in some instances. This is because the distinction between zero and one count in the raw data is also fairly important. Because of this, it is typically not desirable to drown the difference between zero and one with the difference between nine and ten. The difference between zero and one in the discrete attribute value 124 differential (between one cluster and the other clusters) is a significant jump and so a log scale that is able to at least have that floor where "zero" is one color in the heat map 402 and "one" is something that is visually different from "zero." Hence the $\log_2$ scale is used in the heat map 402 illustrated in the Figures. Referring to FIG. 5, toggle 554 provides pop-menu 556 which permits the user to toggle between the fold change and the median-normalized (centered) average discrete attribute value 124 per locus 122 per probe spot in each cluster 158 (e.g., the number of transcripts per probe spot). Thus, in FIG. 5, for Gene ACKR1 the log 2 fold change of the transcripts of ACKR1 in the probe spots of cluster 158-1 relative to all other clusters is 2.17, the $\text{Log}_2$ fold change of the transcripts of ACKR1 in the probe spots of cluster 158-2 relative to all other clusters is −1.94, and so forth. Further menu 556 can be used to display the mean-normalized average value of ACKR1 in each of the clusters, as well as the mean-normalized average value of other loci that are represented in the discrete attribute value dataset 120. In some embodiments, the average value is some other measure of central tendency of the discrete attribute value 124 such as an arithmetic mean, weighted mean, midrange, midhinge, trimean, Winsorized mean, median, or mode of all the discrete attribute values 124 for the locus 122 measured in each of the probe spots in the respective cluster 158. FIGS. 4 and 5 provides a means for discerning between those loci 122 (e.g., genes) that are associated with significant average discrete attribute values 124 (e.g., fairly high transcript counts) in all the k-means clusters 158 and those loci 122 (e.g., genes) that are associated with appreciable discrete attribute values 124 that localized to only certain k-means clusters.

Another aspect of the present disclosure handles situations in which the pipeline consists of multiple classes 172 of tissue. That is, situations in which each such sample consists of first discrete attribute values 124 for each respective locus 122 (e.g., mRNA that map to a particular gene in a plurality of genes) in each probe spot associated with a first condition (therefore representing a first class 172), second discrete attribute values 124 for each respective locus 122 in each probe spot associated with a second condition (therefore representing a second class 172), and so forth, where each such class 172 refers to a different tissue type, different tissue condition (e.g., tumor versus healthy) a different organ type, a different species, or different assay conditions (e.g., dye type) or any of the forgoing. In some embodiments, the discrete attribute value dataset 120 contains data for two or more such classes, three or more such classes, four or more such classes, five or more such classes, ten or more such classes 172, or 100 or more such classes 172.

In some embodiments, there are multiple classes 172 of probe spots 126. In some embodiments, each probe spot contains multiple classes. In some embodiments, only a subset of the probe spots belong to one class (category) while other probe spots belong to a different category. In some embodiments, each such sample comprises first discrete attribute values 124 for each respective locus 122 (e.g., mRNA that map to a particular gene in a plurality of genes) in each probe spot in a first plurality of probe spots under a first condition (therefore representing a first class 172), second discrete attribute values 124 for each respective locus 122 in each probe spot in a second plurality of different probe spots under a second condition (therefore representing a second class 172), and so forth. In other situations, each such sample comprises first discrete attribute values 124 for each respective locus 122 (e.g., mRNA that map to a particular gene in a plurality of genes) in each probe spots in a first plurality of probe spots of a first type (a first class 172), second discrete attribute values 124 for each respective locus 122 in each probe spots in a second plurality of probe spots of a second type (a second class 172), and so forth, where each such class 172 refers to a different tissue type, a different organ type, a different species, or different assay conditions or any of the forgoing. In some embodiments, the discrete attribute value dataset 120 contains data for probe spots from two or more such classes, three or more such classes, four or more such classes, five or more such classes, ten or more such classes 172, or 100 or more such classes 172.

In some embodiments, probe spot data is aggregated across multiple biological samples (e.g., different sections of a tissue biopsy, etc.). The images for each such respective biological sample (or section from a biological sample) constitutes a spatial projection 121 of FIG. 1B. In some embodiments, each such section is prepared as disclosed in I. Introduction; (d) Biological samples; (ii) Preparation of biological samples; (1) Tissue sectioning of U.S. Provisional Patent Application No. 62/938,336, entitled "Pipeline for Analysis of Analytes," filed Nov. 21, 2019, which is hereby incorporated by reference in its entirety.

In some embodiments, there is a plurality of categories 170 and each probe spot 126 is in each such category 170. In such embodiments, each category 170 has one or more subcategories, termed classes 172 that can be individually selected. In some embodiments, all such data is preloaded into a single discrete attribute value dataset 120. Examples of categories include k-means clustering (where K-means is the category 170 and each k-means cluster 158 is an example of a class 172), LibraryID (where LibraryID is the category 170 and which library a probe spot originated from is the class 172), and Biological Label (where "Biological Label" status is the category 170, and the value for the "Biological Label" the sample that was used to construct the discrete attribute dataset 120 is the class 172). An example of a Biological Label is an indication as to whether a subject has or does not have colorectal cancer. In this example, there are two classes 172, one for instances where a subject that contributed the biological sample for the discrete attribute value dataset 120 has colorectal cancer and one for instances where a subject that contributed the biological sample for the discrete attribute value dataset 120 does not have colorectal cancer.

Turning to FIG. 4, by selecting affordance 450, a dropdown menu (not shown) is provided that shows all the different categories 170 that are associated with the discrete attribute value dataset 120. In some embodiments, where there is a category 170 in a discrete attribute value dataset 120 having classes 172, each respective probe spot 126 in the discrete attribute value dataset 120 is a member of each respective category 170 and one of the classes 172 of each respective category 170. In some such embodiments, where the dataset comprises a plurality of categories 170, each respective probe spot in the discrete attribute value dataset 120 is a member of each respective category 170, and a single class of each respective category 170.

In some embodiments, where there is a category 170 in a discrete attribute value dataset 120 that has no underlying classes 172, a subset of the probe spots in the dataset 120 are a member of the category 170.

In some embodiments, where there is a category 170 in a discrete attribute value dataset 120 having subclasses 172, only a portion of the respective probe spots in the dataset 120 are a member of the category 170. Moreover, each probe spot in the portion of the respective probe spots is independently in any one of the respective classes 172 of the category 170.

As illustrated in FIG. 4, a user can select or deselect any category 170. As further illustrated, a user can select or deselect any combination of subcategories 172 in a selected category 170. Referring to FIG. 4, in some embodiments, the user is able to click on a single cluster 158 (the clusters 1-11 are labeled as 172-1-2, 172-1-3, 172-1-4, 172-1-5, 172-1-6, 172-1-7, 172-1-8, 172-1-9, 172-1-10, and 172-1-11 respectively, in FIG. 4) to highlight it in the plot 420. In some embodiments, when the user clicks on a highlighted cluster 158 in the plot 420, the highlighting is removed from the selected cluster.

The presentation of the data in the manner depicted in FIG. 4 advantageously provides the ability to determine the loci 122 whose discrete attribute values 124 separates (discriminates) classes 172 within a selected category based upon their discrete attribute values. To further assist with this, the significant loci (e.g., Sig. genes) affordance 450 is selected thereby providing two options, a globally distinguishing option 452 and a locally distinguishing option (not shown in FIG. 4).

Referring to FIG. 4, the globally distinguishing option 452 identifies the loci 122 whose discrete attribute values 124 within the selected classes 172 statistically discriminate with respect to the entire discrete attribute value dataset 120 (e.g., finds genes expressed highly within the selected clusters 172, relative to all the clusters 172 in the dataset 120). The locally distinguishing option identifies the loci whose discrete attribute values discriminate the selected clusters (e.g., class 172-1-1 and class 172-1-11 in FIG. 4) without considering the discrete attribute values 124 in classes 72 of probe spots that have not been selected (e.g., without considering classes 172-1-2 through 172-1-10 of FIG. 4).

In some embodiments, visualization system 100 comprises a plurality of processing cores 102 and the identification of loci whose discrete attribute values discriminate classes under either the globally distinguishing or locally distinguishing algorithms makes use of the processing cores 102 to independently build up needed statistics (e.g., a measure of central tendency of the discrete attribute value) of individual loci across a class and/or one or more categories of a class of probe spots (or the entire dataset).

Advantageously, with reference to FIG. 5, the systems and methods of the present disclosure allow for the creation of new categories 170 using the upper panel 420 and any number of classes 172 within such categories using lasso 552 or draw selection tool 553 of FIG. 4. So, if a user would like to identify probe spot subtypes (classes 172), this can be done by selecting a number of probe spots displayed in the upper panel 420 with the lasso tools. Moreover, they can also be selected from the lower panel 404 (e.g., the user can select a number of probe spots by their discrete attribute values). In this way, a user can drag and create a class 172 within a category 170. The user is prompted to name the new category 170 and the new class (cluster) 172 within the category. The user can create multiple classes of probe spots within a category. For instance, the user can select some probe spots using affordance 552 or 553, assign them to a new category (and to a first new class within the new category). Then the user selects additional probe spots using tools 552 or 553 and, once selected, assigns the newly selected probe spots to the same new category 170, but now to a different new class 172 in the category. Once the classes 172 of a category have been defined in this way, the user can compute the loci whose discrete attribute values 124 discriminate between the identified user defined classes. In some such embodiments, such operations proceed faster than with categories that make use of all the probe spots in the discrete attribute value dataset 120 because fewer numbers of probe spots are involved in the computation. In some embodiments, the speed of the algorithm to identified loci that discriminate classes 172 is proportional to the number of classes 172 in the category 170 times the number of probe spots that are in the analysis. For instance, in some embodiments, identification of discriminating loci in the case where there are two classes and twenty-five probe spots takes about four to five seconds on a standard client device 100.

In some embodiments, a discrete attribute value dataset 120 can have data for up to 750,000 probe spots and still identify loci that discriminate between classes of 172 of a category 170 in real time (e.g., less than 30 minutes, less than 10 minutes, less than 5 minutes, or less than 1 minute).

Referring to FIG. 4, when a dataset in accordance with such embodiments of the present disclosure is loaded, the visualization module 119 provides the panel 402 illustrated in FIG. 4, which is a heat map prepared in accordance with block 206, described above in conjunction with FIG. 4. Namely, the differential value 162 for each respective locus 122 in the plurality of loci for each respective cluster 158 in the plurality of clusters derived from a discrete attributed value dataset 120 are computed, and a heat map 402 of these differential values is displayed in a first panel 404 of an interface 400 of FIG. 4. The heat map 402 comprises a representation of the differential value 162 for each respective locus 122 in the plurality of loci for each cluster 158 in the plurality of clusters. In FIG. 4, the clusters are formed in accordance with block 214 in which a Louvain modularity algorithm is used. See, Blondel et al., Jul. 25, 2008, "Fast unfolding of communities in large networks," arXiv: 0803.0476v2 [physical.coc-ph], which is hereby incorporated by reference.

As illustrated in FIG. 4, the differential value 162 for each locus 122 in the plurality of probe spots for each cluster 158 is illustrated in a color-coded way to represent the $\log_2$ fold change in accordance with color key 408. In accordance with color key 408, those loci 122 that are upregulated in the probe spots of a particular cluster 158 relative to all other clusters are assigned more positive values, whereas those loci 122 that are down-regulated in the probe spots of a particular cluster 158 relative to all other clusters are assigned more negative values. In some embodiments, the heat map can be exported to persistent storage (e.g., as a PNG graphic, JPG graphic, or other file formats).

Referring to FIG. 4, advantageously, affordance 450 can be used to toggle to other visual modes. In FIG. 4, a particular "Categories" mode, "Graph based" (170) is depicted, which refers to the use of a Louvain modularity algorithm to cluster discrete attribute value 124 as disclosed above with reference to block 214. However, by selecting affordance 450, other options are displayed for affordance 170. In particular, in addition to the "Categories" option that was displayed in FIG. 4, "Gene Expression" can be selected as options for affordance 450. As an example, with reference to FIG. 1B, consider the case of a probe spot 126 in the discrete attribute value dataset 120. This probe spot is supported by a barcode on the basis that the probe spot sequence information was obtained from the discrete attribute value pipeline.

Discrete Attribute Value Pipeline.

In some embodiments, "raw" data acquired from sample processing hardware is transformed into a discrete attribute value dataset, which can be generated and stored in a suitable format. In some embodiments that implement the visualization module 119, the discrete attribute value dataset is in a ".cloupe" format. A feature barcode pipeline is configured to count both gene expression per probe spot as well as non-gene features per probe spot.

Each data point in a discrete attribute value dataset can be stored as a high-dimensional data point. In this way, in some embodiments, a feature-barcode matrix can be generated. In typical embodiments, a dataset 120 will contain a single feature-barcode matrix. A set of barcodes will be associated with the dataset. Each probe spot in an image will contain a unique barcode from the plurality of barcodes. In discrete attribute value datasets 120 that have multiple spatial projections 121, that is, they represent multiple samples such as sections of a tissue, the feature-barcode matrix originally determined for each spatial projection is combined into the single feature-barcode matrix of the discrete attribute value dataset 120. In some embodiments, in order to combine matrices, the samples (discrete attribute value data 124 of individual spatial projections 121) are adjusted for differences in sequencing depth between spatial projections 121 and, optionally, "batch effect" correction is performed in order to remove signal due to technical differences, such as changes in chemistry (e.g. combining 10×, Pleasanton, California CHROMIUM v2 data with 10× CHROMIUM v3 data) across the discrete attribute value data 124 of individual spatial projections 121. In some embodiments, this is accomplished using techniques disclosed in Hafemeister and Satija, "Normalization and variance stabilization of single-cell RNA-seq data using regularized negative binomial regression," bioRxiv 576827 (2019). doi:10.1101/576827, which is hereby incorporated by reference.

In datasets that have multiple images, spatially corresponding probe spots in images will have the same barcode. Thus, the upper left probe spot in each image of a dataset will have the same barcode and this barcode will be different than all the other probes spots in the images. To discriminate between these spatially corresponding probe spots across images, in some embodiments the barcodes will contain a suffix or a prefix, which will indicate from which image the probe spot (and subsequent measurements) originated. Because the same barcodes are used in every image, this identifies which image each sequence read originated in. For instance, the barcode ATAAA-1 from a respective probe spot in image 125-1-1 will be different from ATAAA-2 in the spatially corresponding probe spot from image 125-1-2. In some embodiments, graph-based, k-Means, t-SNE and UMAP projections are derived from the single feature-barcode matrix that has been integrated across all the images 125 of all the spatial projections 121 of the discrete attribute set. Thus, in embodiments in which the discrete attribute value dataset includes multiple spatial projection the mathematical projections will include all probe spots across multiple spatial projections; a single t-SNE and UMAP plot per locus (gene, antibody capture, specific genetic loci on a reference genome) will be created per dataset. Thus, spots from similar tissue types or subtypes across multiple tissue sections should cluster together in the abstract t-SNE/UMAP/PCA space, but may span multiple spatial projections.

In some embodiments, similar to the embodiments described above, principal component analysis, or other forms of data reduction, such as subset selection (e.g., as disclosed in Hastie, 2001, *The Elements of Statistical Learning*, Springer, New York, pp. 55-57), discrete methods (e.g., as disclosed in Furnival & Wilson, 1974, "Regression by Leaps and Bounds," Technometrics 16(4), 499-511), forward/backward stepwise selection (e.g., as disclosed in Berk, 1978, "Comparing Subset Regression Procedures," Technometrics 20:1, 1-6), shrinkage methods (e.g., as disclosed in Hastie, 2001, *The Elements of Statistical Learning*, Springer, New York, pp. 59-66), ridge regression (e.g., as disclosed in Hastie, 2001, *The Elements of Statistical Learning*, Springer, New York, pp. 59-64), lasso techniques (e.g., as disclosed in Hastie, 2001, *The Elements of Statistical Learning*, Springer, New York, pp. 64-65, 69-72, 330-331), derived input direction methods (e.g., principal component regression (PCR), partial least squares (PLS), etc. as disclosed, for example, in Viyayakurma and Schaal, 2000, "Locally Weighted Projection Regression: An O(n) Algorithm for Incremental Real Time Learning in High Dimensional Space, Proc. of Seventeenth International Conference on Machine Learning (ICML2000), pp. 1079-1086), or combinations thereof, are used to reduce the dimensionality of the data down to a certain number of dimensions (e.g., ten dimensions, or another number of dimensions).

In some embodiments, the feature counts per probe spot are stored as sparse matrices in compressed sparse column (CSC) and compressed sparse row (CSR) formats. Furthermore, each row in the feature-barcode matrix includes additional metadata, which can be automatically generated by the pipeline hardware and/or acquired based on user input.

In some embodiments, of the present disclosure, a data structure storing the feature-barcode matrix is accessed by processing core(s) 102 of the visualization system 100 or by another computing device (e.g., a remote computing device or server) and clusters can be detected in the data (discrete attribute values) stored in the format of this matrix. Any of the techniques described above, or a combination of these techniques, can be implemented for the clustering. For example, in some embodiments, the clustering of the discrete attribute values comprises hierarchical clustering, agglomerative clustering using a nearest-neighbor algorithm, agglomerative clustering using a farthest-neighbor algorithm, agglomerative clustering using an average linkage algorithm, agglomerative clustering using a centroid algorithm, or agglomerative clustering using a sum-of-squares algorithm. In some embodiments, the clustering includes application of a Louvain modularity algorithm, k-means clustering, a fuzzy k-means clustering algorithm, or Jarvis-Patrick clustering. The clustering can be performed on the entire dataset of the feature-barcode matrix, or using only a portion of the dataset. In some embodiments, the portion from the dataset can be selected for clustering based on user input. Furthermore, in some embodiments, the portion from the dataset can be selected for clustering automatically—e.g., based on certain characteristics of the features in the dataset.

Spatial Information.

FIGS. 4 and 5 illustrate example user interfaces where probe spots are identified based in part on spatial localization with respect to a glass slide (e.g., a slide with a tissue sample that has been imaged prior to sequencing analysis). In these figures, the example images upon which the probe spot localizations correspond to a section of tissue (e.g., the plurality of probe spots and their corresponding information are derived from a section of tissue).

Storage of Spatial Information.

In some embodiments, the .cloupe files provide for efficient visualization and zooming. In particular, information for each image file is stored in the form of tiles (e.g., in an image tiles data structure), to allow for progressive rendering, smooth panning and zooming. The use of tiles to display images at different resolutions and sizes essentially prevents overloading the visualization module with the memory requirements of a typical microscope image (which can be up to gigabytes in size and tens of thousands of pixels on a side).

In some embodiments, images are tiled and named in a format compatible with the DZI (DeepZoom image) schema or the open-source OpenSeaDragon image viewer. See e.g., "Deep Zoom File Format Overview" pub. Nov. 16, 2011 https://docs.microsoft.com/en-us/previous-versions/windows/silverlight/dotnet-windows-silverlight/cc645077 (v=vs.95)?redirectedfrom=MSDN and Goode et al. 2013 J Pathol Inform 4(27). In this schema, in some embodiments, the original image is divided into individual tiles, and then the image is iteratively resampled and retiled until the entire image can fit onto one tile.

Figure 13:
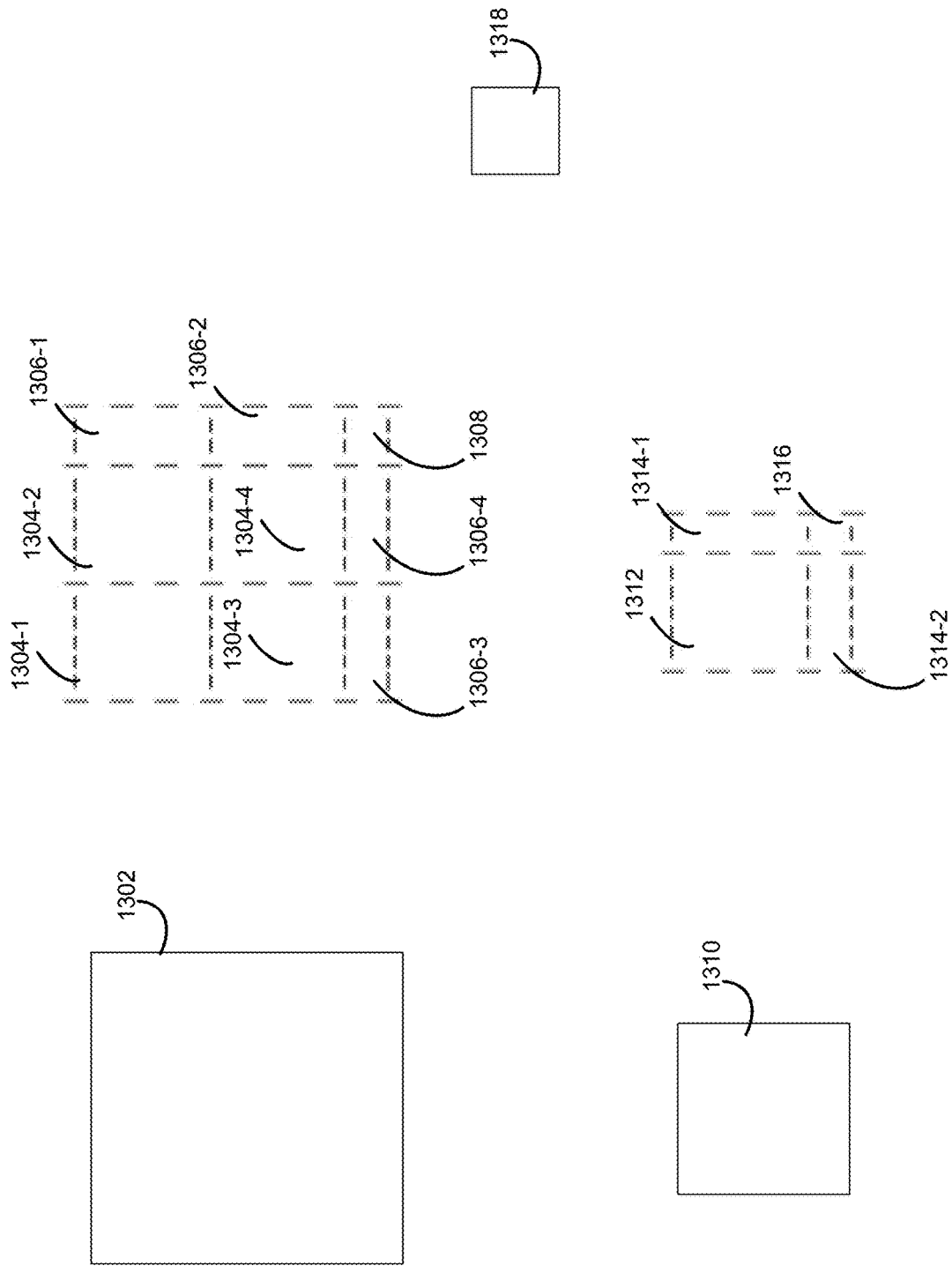
FIG. 13 illustrates subdividing image files into tiles for efficiently storing image information in accordance with some embodiments of the present disclosure.

For example, as shown in FIG. 13, an original 600×600 image 1302, with a desired max tile size of 256×256, would be divided into a first set of tiles (1304, 1306, and 1308) including three rows and three columns of tiles. Four tiles 1304-1, 1304-2, 1304-3, and 1304-4 are of a size 256×256 e.g., the maximum tile size). Two tiles 1306-1 and 1306-2 are of a size 88×256 and two tile 2306-3 and 2306-4 are of a size 256×88. The final tile 2308 is then of a size 88×88 pixels.

On the next iteration, the size of original file 1302 is reduced by half (e.g., to that of the first reduced file 1310). Thus, the first reduced file is of the size 300×300, and the resulting image is divided into a second set of tiles (1312, 1314, and 1316). One full size tile, 1312, fits in reduced image 1310. In addition, tile 1314-1 has a size 44×256, and tile 1314-2 is of a size 256×44. Finally, one additional tile 1316 fills the rest of first reduced file 1310 and is of the size 44×44.

On the next iteration, the first reduced file 1310 is halved in size again to second reduced file 1318 with a size of 150×150. At this size, the second reduced file thus would fit within a single tile. Thus, the original file has been reduced as much as possible without losing resolution. The contents of all the tiles from the first and second reduced files are encoded in an ImageTiles data structure within the .cloupe file format. In some embodiments, the ImageTiles data structure includes at least the format of each tile, the (square) size of each tile, the dimensions of the original image, by how many pixels (or if) the tiles overlap, a path to the tile location, or null if the tiles are in the .cloupe file, a mapping of tile key to a block structure (e.g., describing the byte offset and compression mechanism of the tile within the .cloupe file), and the parent image reference.

In some embodiments, each image file with spatial location information is stored with a predetermined number of tiles (e.g., at least 5, at least 10, at least 20, at least 30, at least 40, at least 50, at least 60, at least 70, at least 80, at least 90, at least 100, at least 150, at least 200 tiles, at least 250 tiles, at least 500 tiles, at least 750 tiles, at least 1000 tiles, at least 1250 tiles, at least 1500 tiles, at least 1750 tiles, at least 2000 tiles, at least 2500 tiles, at least 3000 tiles, at least 3500 tiles, at least 4000 tiles, at least 4500, or at least 5000 tiles). In some embodiments, each original image file is partitioned into files and reduced a predetermined number of times (e.g., at least 1 reduction in size, at least 2 reductions in size, at least 3 reductions in size, at least 4 reductions in size, at least 5 reductions in size, at least 6 reductions in size, at least 7 reductions in size, at least 8 reductions in size, at least 9 reductions, or at least 10 reductions in size). In some embodiments, each original image file is partitioned until a reduced file that is smaller than a predetermined tile size is reached.

In some embodiments, a respective feature barcode matrix corresponding to a .cloupe file containing spatial information is stored in a sparse array format as described above (e.g., the spatial gene expression data is stored in a sparse format, including the spatial information).

In some embodiments, there are two or more, three or more, four or more, five or more, six or more, or ten our more spatial projections 121 in a single discrete attribute data set.

Spatial Expression Data Visualization.

In some embodiments, a discrete attribute value dataset 120 (e.g., a .cloupe file) includes spatial information (e.g., additional information beyond gene expression data, etc.) for a plurality of probe spots. In some embodiments, the discrete attribute value dataset 120 comprises at least a) a spatial feature-barcode matrix for the relative expression of genomic loci at each probe spot, and b) the coordinates, in image pixel units, of the centers of the spots for each barcode in the feature-barcode matrix. In some embodiments, such discrete attribute value dataset 120 contain multiple projections of the data. Examples of such projections include mathematical projections in t-SNE two-dimensional coordinate space and a UMAP two-dimensional coordinate space (e.g., as described above), projections of probe spot coordinates (e.g., based on the respective barcode for each probe spot), and projections of fiduciary coordinates (e.g., based on the fiduciary dots). A respective set of probe spot coordinates correspond to the center of the corresponding probe spot in pixel units. Some such projections further include the diameter of each probe spot in pixel units.

Figure 7:
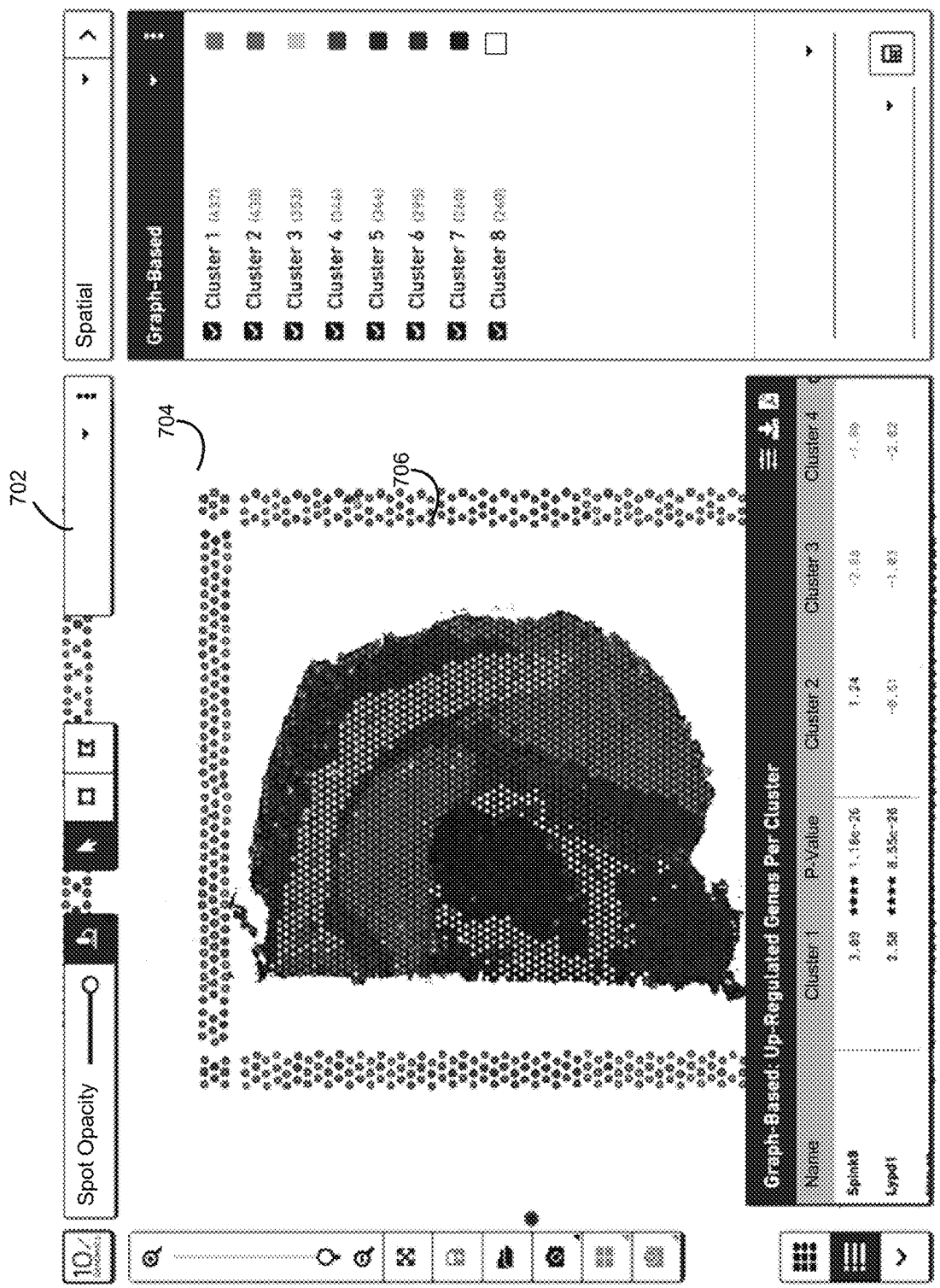
FIG. 7 illustrates an example of a user interface where a plurality of probe spots is displayed in a panel of the user interface, where the spatial location of each probe spot in the user interface is based upon the physical localization of each probe spot on a substrate, where each probe spot is additionally colored in conjunction with one or more clusters identified based on the discrete attribute value dataset, in accordance with some embodiments of the present disclosure.

In some embodiments, opening a discrete attribute value dataset 120 (e.g., .cloupe file) with spatial information comprises opening a spatial analysis view panel 704 within the visualization module (see FIG. 7). The spatial analysis visualization module is, in many aspects, similar to the browser described in U.S. Patent Application 62/886,233, entitled "Systems and Methods for Using the Spatial Distribution of Haplotypes to Determine a Biological Condition," filed on Aug. 13, 2019, which is hereby incorporated by reference. The spatial analysis panel (which is selected, e.g., using the "Spatial" option 702) enables visualization of gene expression in the context of tissue images. In some embodiments, each probe spot is displayed overlaid on an original image, and each probe spot is spatially oriented with respect to every other probe spot in the plurality of probe spots. Further, and as described below, each probe spot is, in some embodiments, annotated (e.g., via color) to indicate gene expression, membership in a cluster (e.g., as described above), and other information.

In some embodiments, a respective discrete attribute value dataset 120 (e.g., .cloupe file) with associated image information includes one or more corresponding image files (e.g., separate from the respective discrete attribute value dataset 120 itself), and opening the respective discrete attribute value dataset 120 does not automatically load the corresponding image files. In other words, in some embodiments, in contrast to what is illustrated in FIG. 1B, images 125 are stored external to the discrete attribute value dataset 120 itself. In some embodiments, after a respective discrete attribute value dataset 120 is opened, a user request to view a corresponding image 125 (or set of images of a projection 121) results in opening spatial analysis view panel 704 within the visualization module and image processing and tiling as required.

Figure 16A:
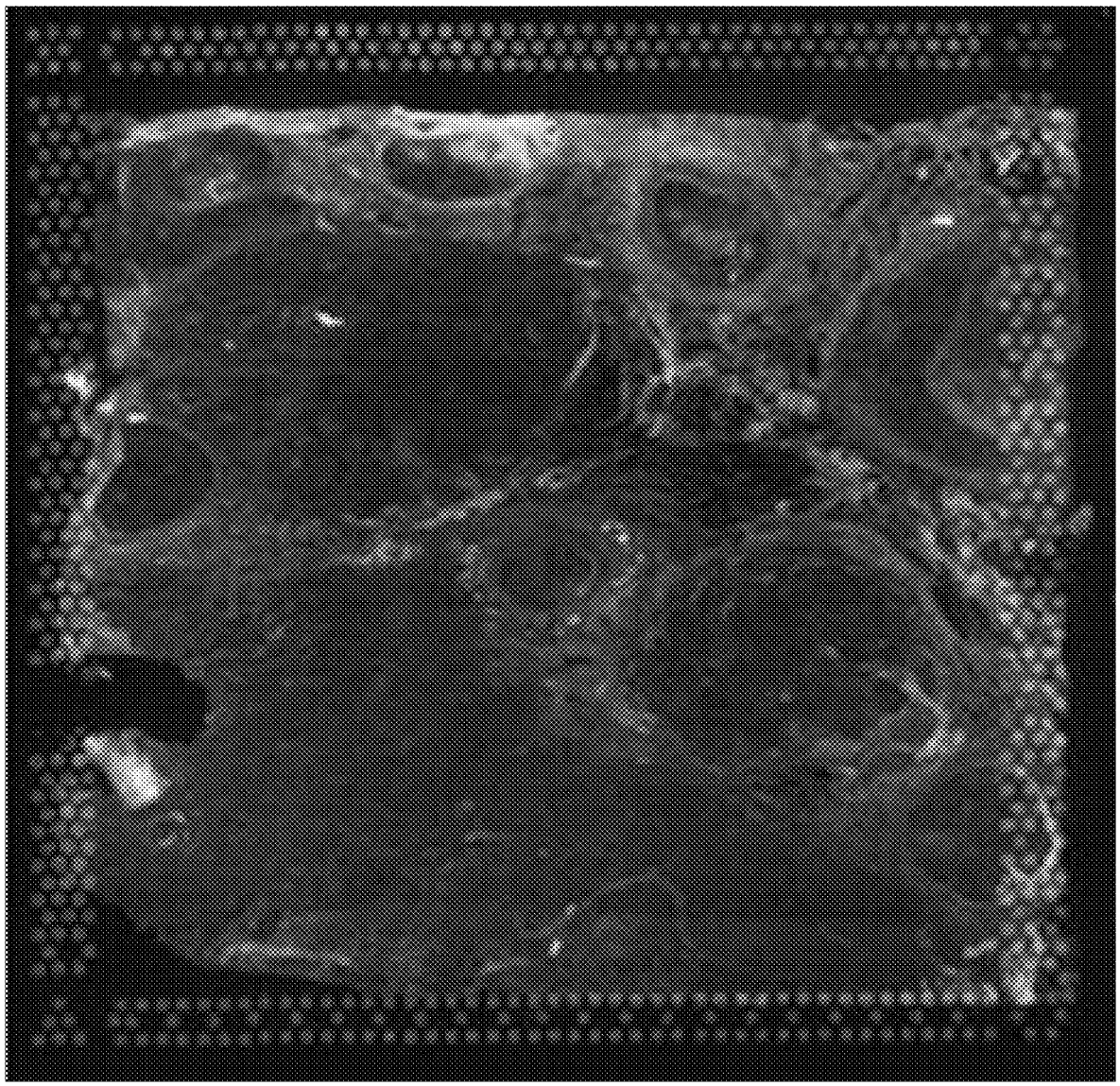
FIG. 16A illustrates an embodiment in which all of the images of a spatial projection are fluorescence images and are all displayed in accordance with an embodiment of the present disclosure.
Figure 16B:
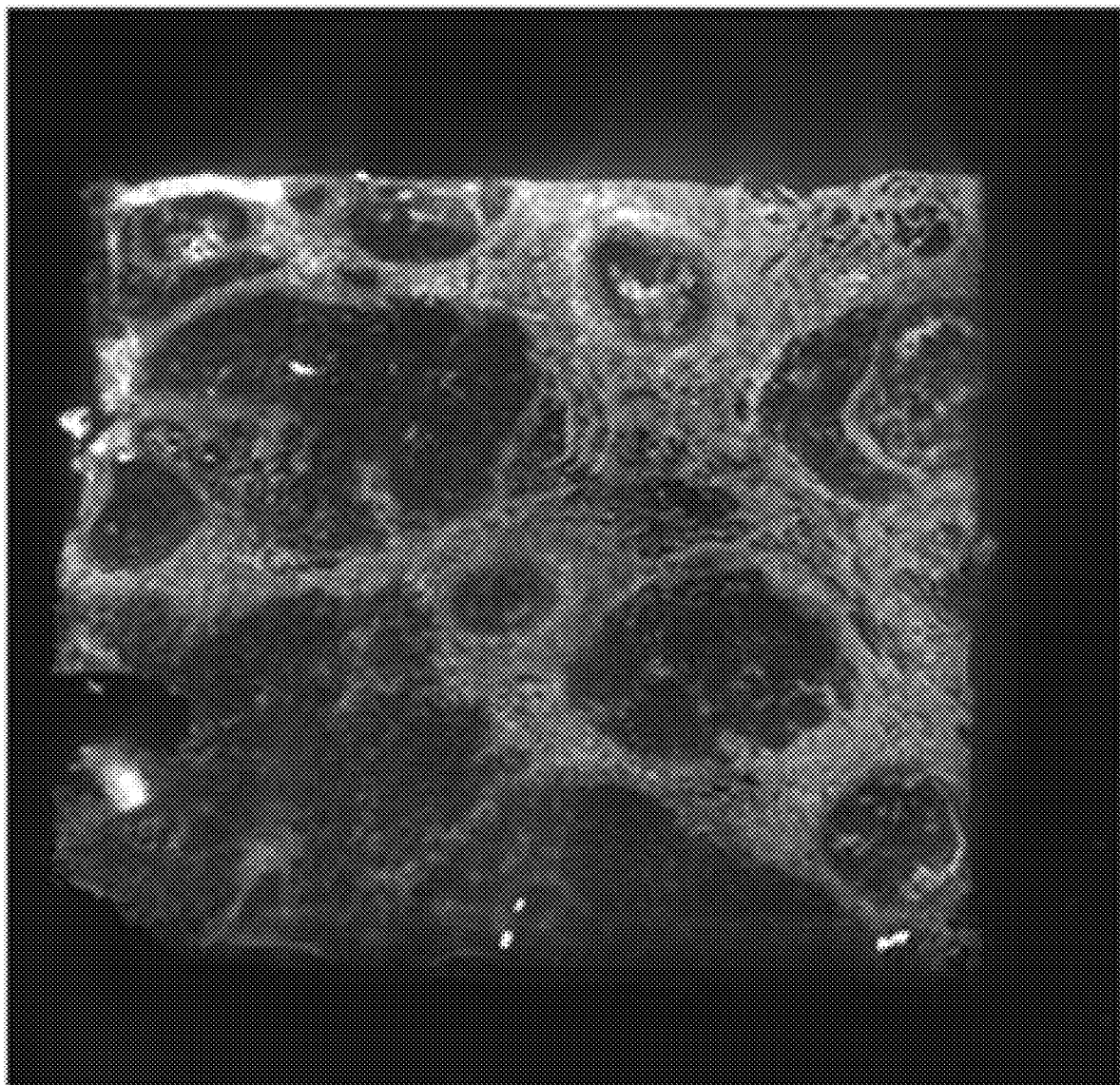
FIG. 16B illustrates the spatial projection of FIG. 16A in which only a CD3 channel fluorescence image of the spatial projection is displayed in accordance with an embodiment of the present disclosure.
Figure 16C:
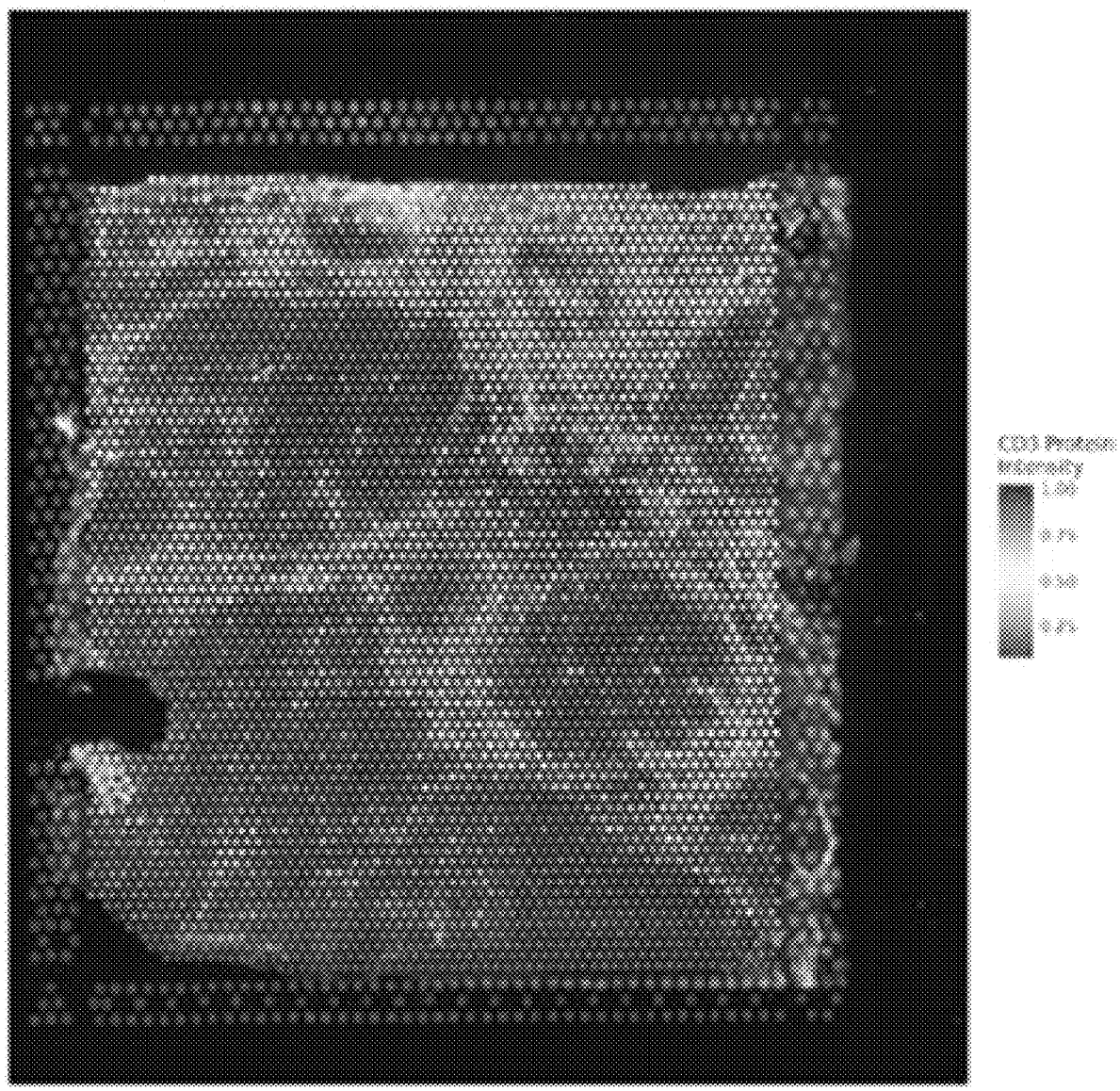
FIG. 16C illustrates the image of FIG. 16B in which CD3 is quantified based on measured intensity in accordance with an embodiment of the present disclosure.

FIGS. 4, 5, 7 and 8 illustrate a single window that displays a spatial projection 121, where the spatial projection 121 consists of a single image 125. As disclosed above, in some embodiments a spatial projection 121 comprises several images. In such instances, a user is able to use the viewer illustrated in FIG. 7 to concurrently view all the images 125 of the single spatial projection 121 overlayed on each other. That is, the viewer illustrated in FIG. 7 concurrently displays all the images 125 of the single spatial projection 121 overlayed on each other. In some such embodiments, the user is able to selectively un-display some of the images 125 of the single spatial projection 121. That is, any combination of the images of a spatial projection, superimposed on each other, can be concurrently viewed in the viewer. Moreover, the user can initiate more than one viewer illustrated in FIG. 7 onto the screen at the same time, and each such viewer can display all or a subset of the images of a corresponding spatial projection 121 on the display. For instance, FIG. 16A illustrates the case in which all of the images 125 of a spatial projection 121 are fluorescence images and are all displayed, whereas FIG. 16B shows the case where only one of the fluorescence images (CD3 channel) of this spatial projection is displayed. In some embodiments, relative brightness in fluorescence images has a semi-quantitative relationship to some aspect of the sample under study. For instance, if the fluorescence arises in an immunohistochemistry fluorescent imaging experiment, then brighter areas have greater binding of some antibody to a protein. For example, FIG. 16C shows CD3 protein quantification using the image of FIG. 16B

As the forgoing demonstrates, the user can therefore concurrently view the one or more images of two or more spatial projections at the same time. Typically, the user will arrange such viewers side by side so that comparisons between the images of respective spatial projections 121 can be made. Such aggregated datasets will have overarching clusters that span multiple images, and also t-SNE and UMAP projections.

Figure 18A:
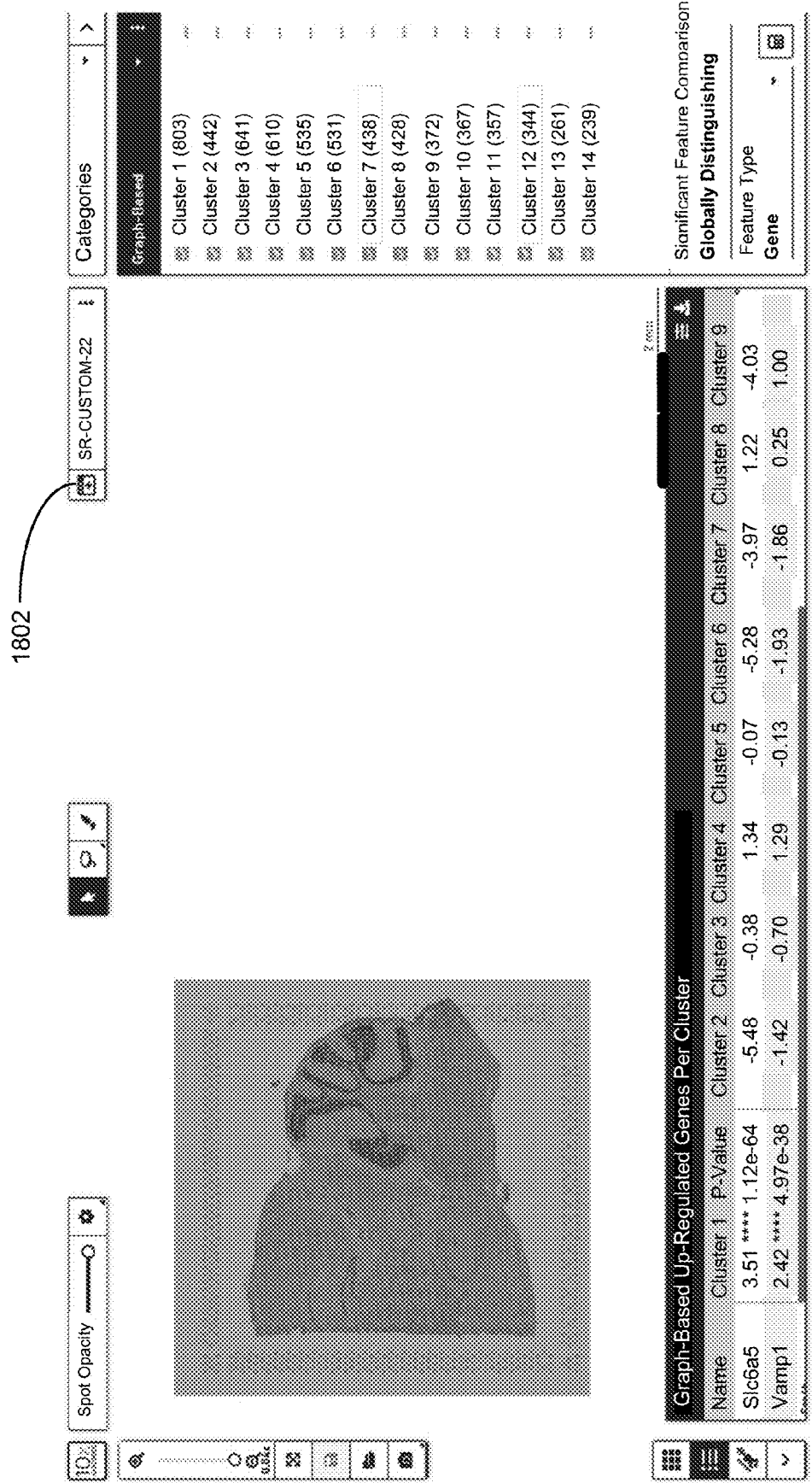
FIGS. 18A, 18B, 18C, 18D, 18E, and 18F illustrate spatial projections that make use of linked windows in accordance with an embodiment of the present disclosure.
Figure 18B:
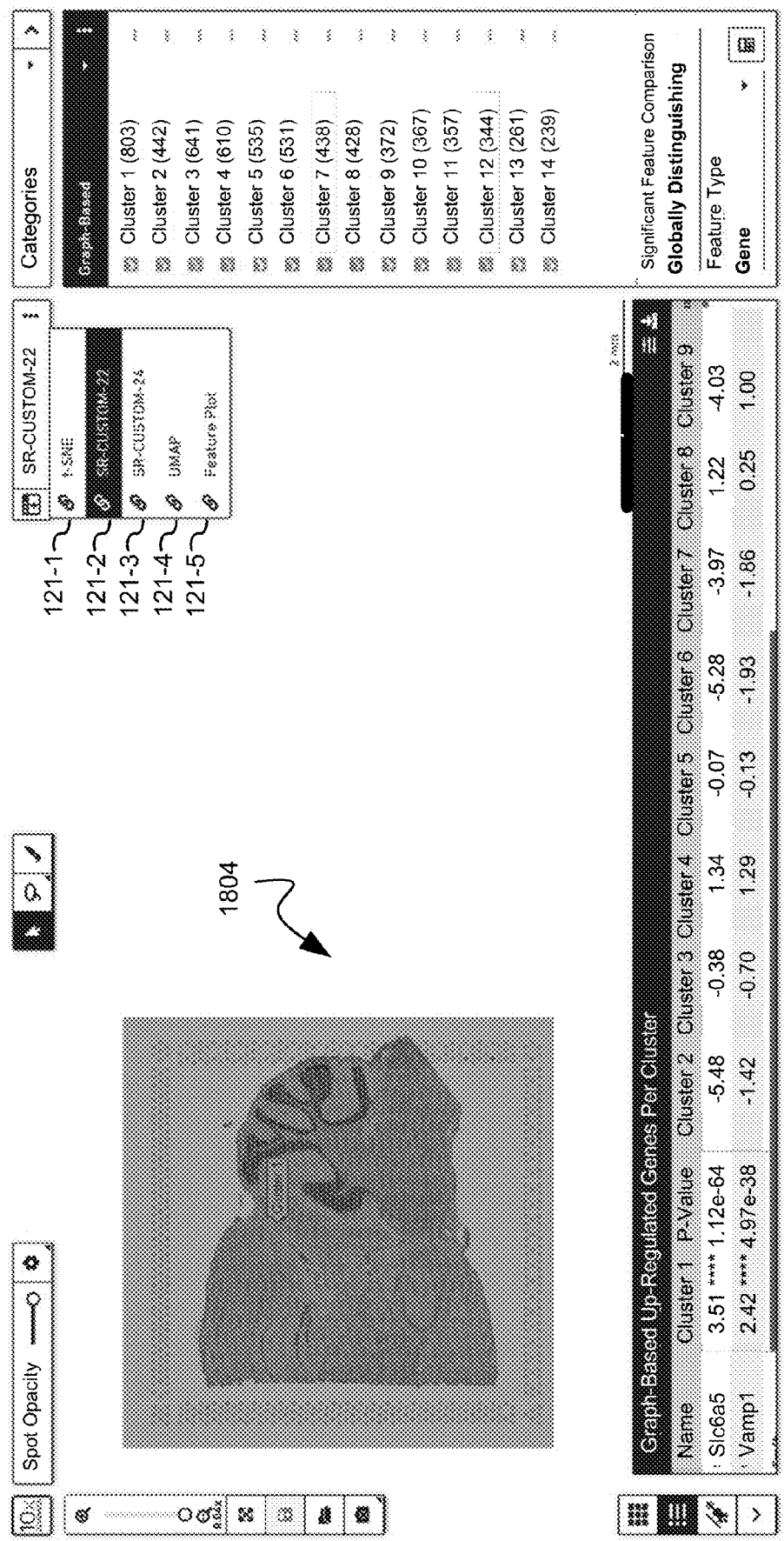
Figure 18C:
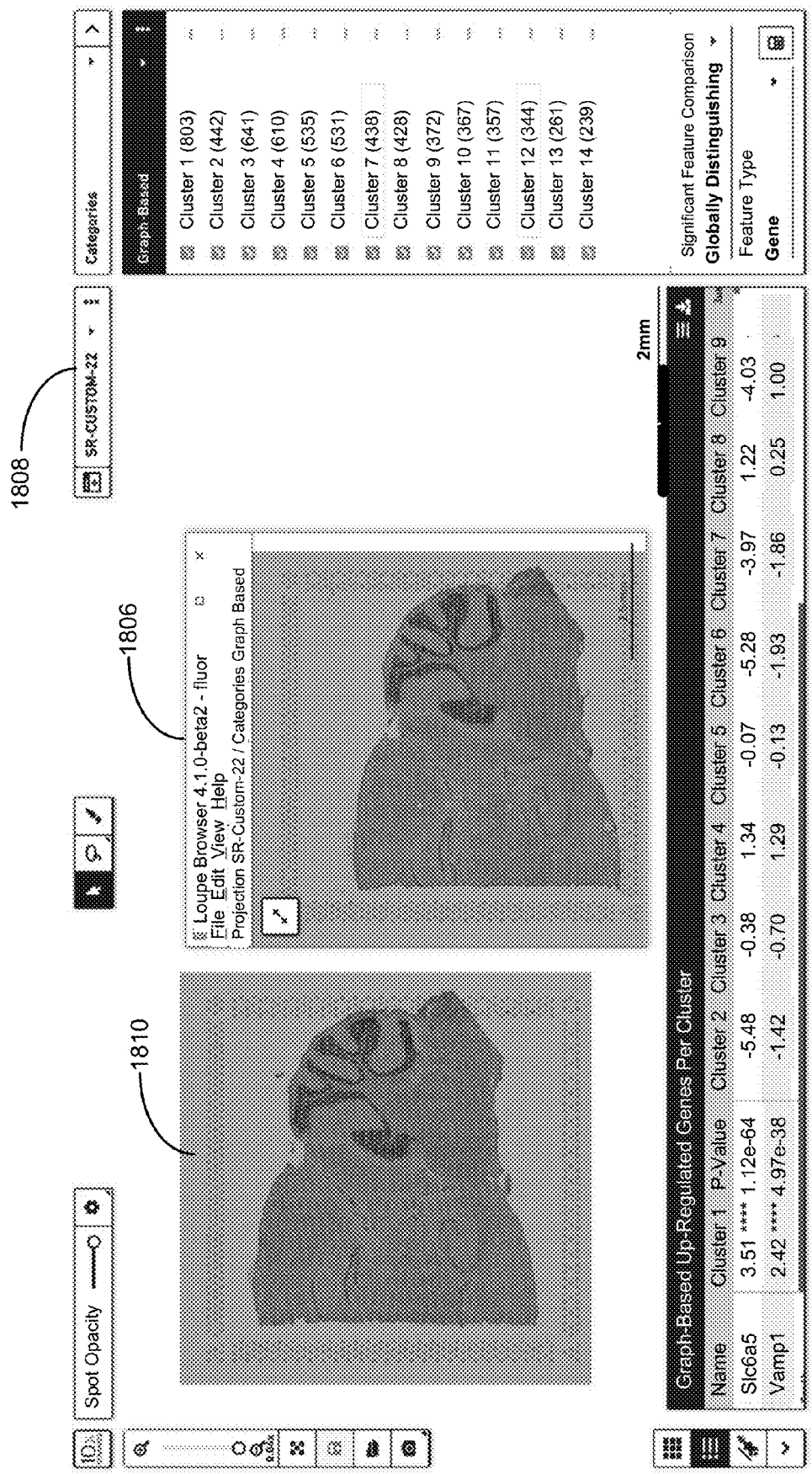
Figure 18D:
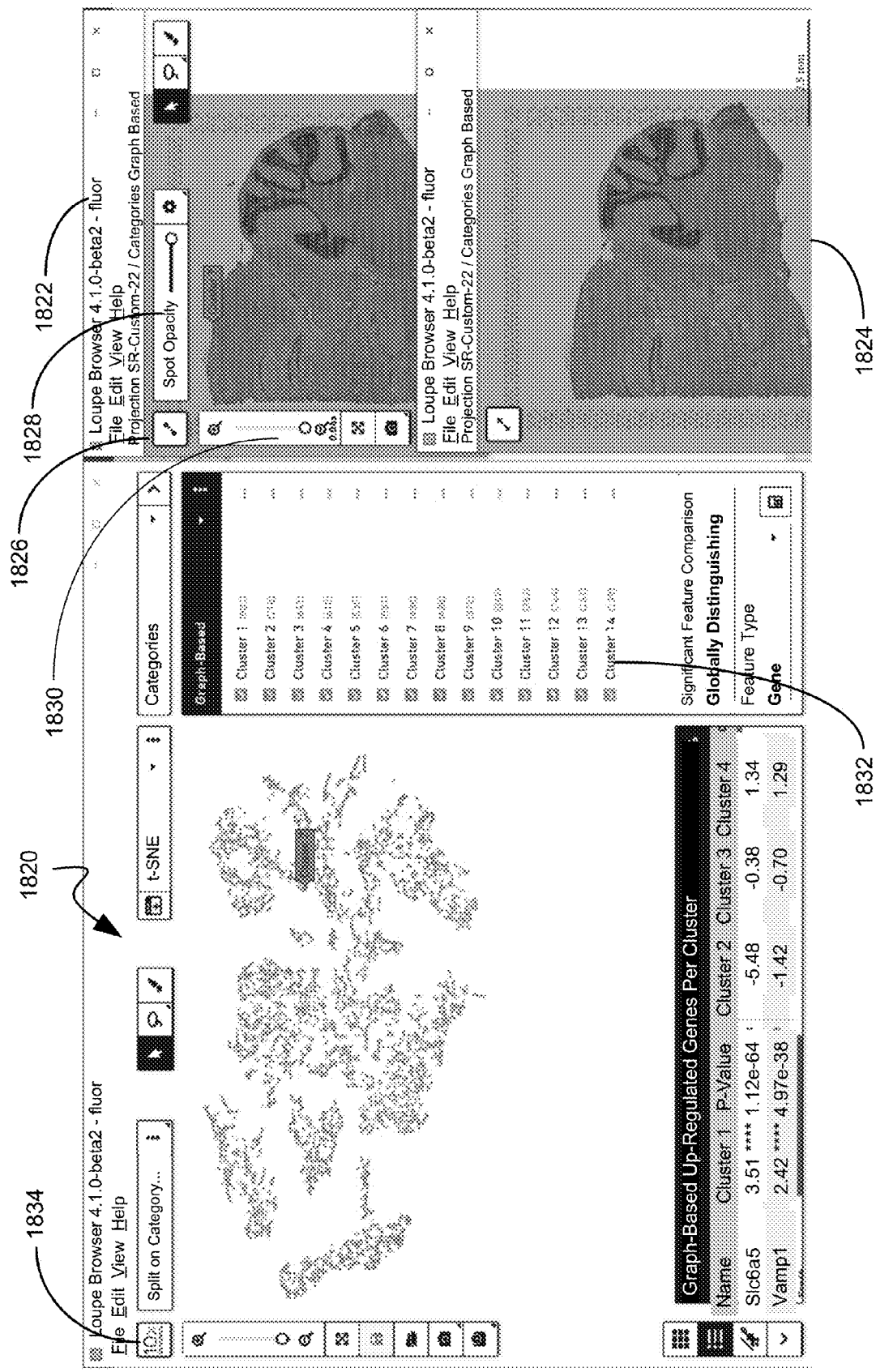

To allow users to see common characteristics or compare different images at once, one aspect of the present disclosure makes use of novel linked windows. Referring to FIG. 18A, clicking on the "Add Window" affordance 1802 brings up a list of projections 121 (see FIG. 18B) for the discrete attribute value dataset 121 to open in a linked window. Thus, referring to FIG. 18B, the projection SR-Custom-22 is visible in panel 1804 and the user has the option of adding a window for projections t-SNE 121-1, SR-Custom-24 121-3, UMAP 121-4, Feature plot 121-5 or, in fact, another instance of SR-Custom-22 121-1. Clicking on one of these projections opens that projection in a smaller window within the operating system. For instance, clicking on SR-Custom-24 121-3 in FIG. 18B causes a smaller window 1806 with this projection to be concurrently displayed with SR-Custom-22 121-2 as illustrated in FIG. 18C. In FIG. 18C, it is clear from menu 1808 that the projection 1810 to the far left in the panel is that of SR-Custom-22 121-2. One can create multiple linked windows for a single dataset in this manner as illustrated in FIG. 18D. In FIG. 18D, the main panel 1820 is that of projection t-SNE 121-1 while smaller windows 1822 and 1824 are for projections SR-Custom-22 121-2 and SR-Custom-24 121-3 respectively. In some embodiments, linked windows (e.g., windows 1822 and 1824 of FIG. 18D) open initially in miniaturized view as illustrated in FIG. 18D, where only the projection and a button 1826 to expand the window to a full panel is shown. As illustrated in FIG. 18D, when using a mouse cursor to hover over a linked window (e.g., window 1822), more options 1828 and 1830 are revealed that provide a subset of common actions, such as the ability to pan and zoom a linked window. However, the linked windows are still predominantly controlled by manipulating the original, or anchor window 1820.

Referring to FIG. 18D, changes to the anchor window 1820 will propagate automatically to the other linked windows (e.g., windows 1822 and 1824), such as using toggles 1832 to change active clusters (which clusters are displayed across all the linked windows), selecting an individual cluster, creating a new cluster or modifying a cluster, selecting one or more genes to show feature expression (gene, antibody, peak), changing cluster membership, changing individual cluster colors or the active expression color scale, in (VDJ mode) selecting active clonotypes, and in (ATAC mode) selecting transcription factor motifs. However, features such as panning, zooming, spatial image settings (pre-save) such as color, brightness, contrast, saturation and opacity, selected spatial projection 121, and window sizes remain independent in the anchor and linked windows.

Referring to FIG. 18D, it is possible to expand a linked window from mini-mode to access the full range of visualization options by clicking on the expand affordance 1826. Clicking the window again will shrink it back to mini-mode. In some embodiments, changes to the discrete attribute value dataset 120 in any window are saved through the anchor window. Thus, referring to FIG. 18D, any change to the discrete attribute value dataset 120 in windows 1822 or 1824 must be saved through window 1820 in such embodiments.

Figure 18E:
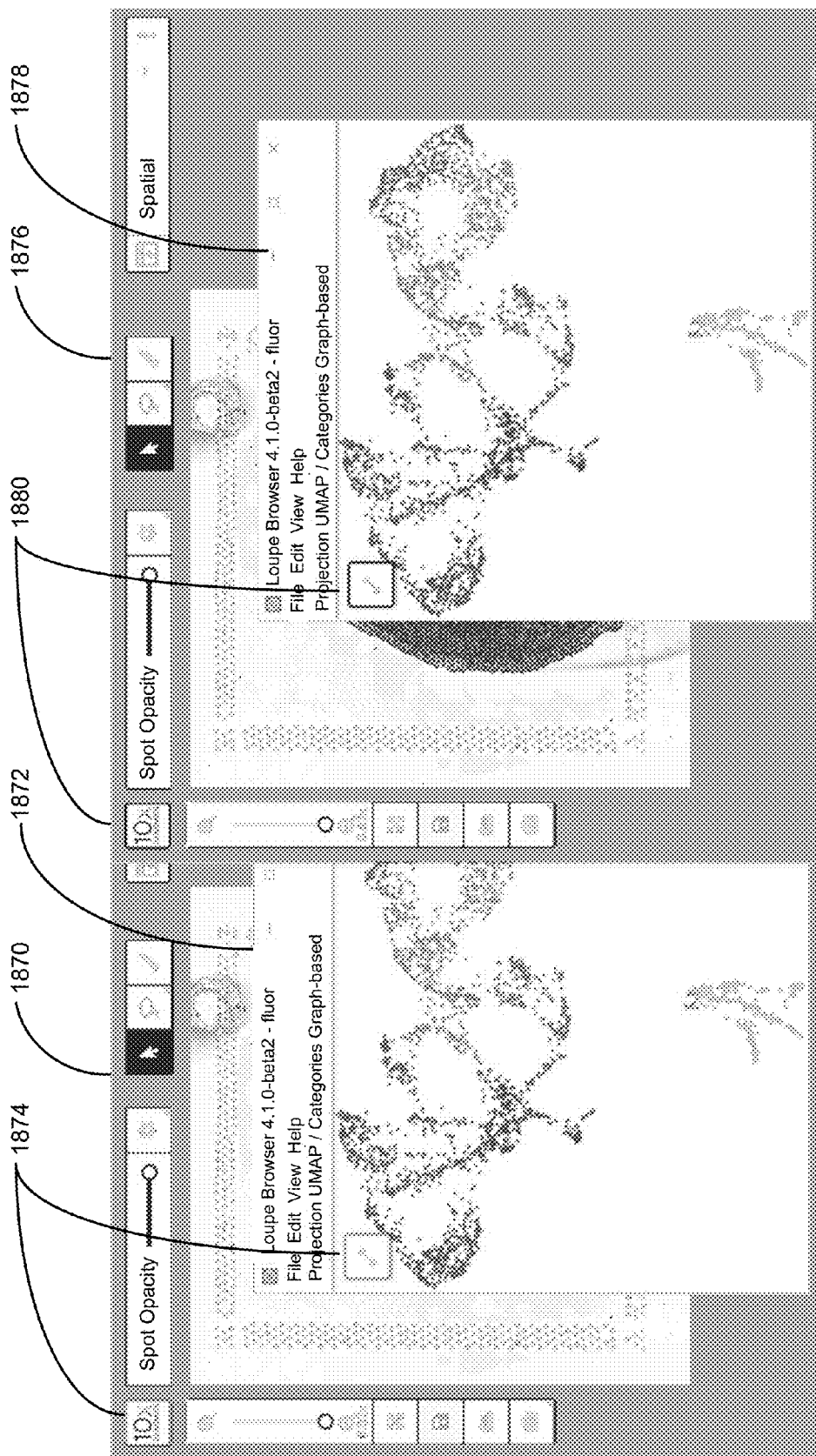

It is also possible to have other linked windows open to view other discrete attribute value datasets 120. To avoid confusion, when multiple attribute value datasets are open, the color of the button 1834 (FIG. 18D) will signify which windows are linked. For instance, referring to FIG. 18E, windows 1870 and 1872, which represent two different spatial projections 121 for a first discrete attribute dataset 120, are linked and so have a common orange border on logo 1874, while windows 1876 and 1878, which represent two different spatial projections 121 for a second discrete attribute dataset 120, are linked and so have a common black border on logo 1880. Moreover, linked windows are not limited to spatial discrete attribute value datasets 120. Most gene expression datasets have both t-SNE and UMAP projections 121 (see U.S. patent application Ser. No. 16/442,800 entitled "Systems and Methods for Visualizing a Pattern in a Dataset," filed Jun. 17, 2019) that can be linked and viewed at the same time in a similar fashion.

Figure 18F:
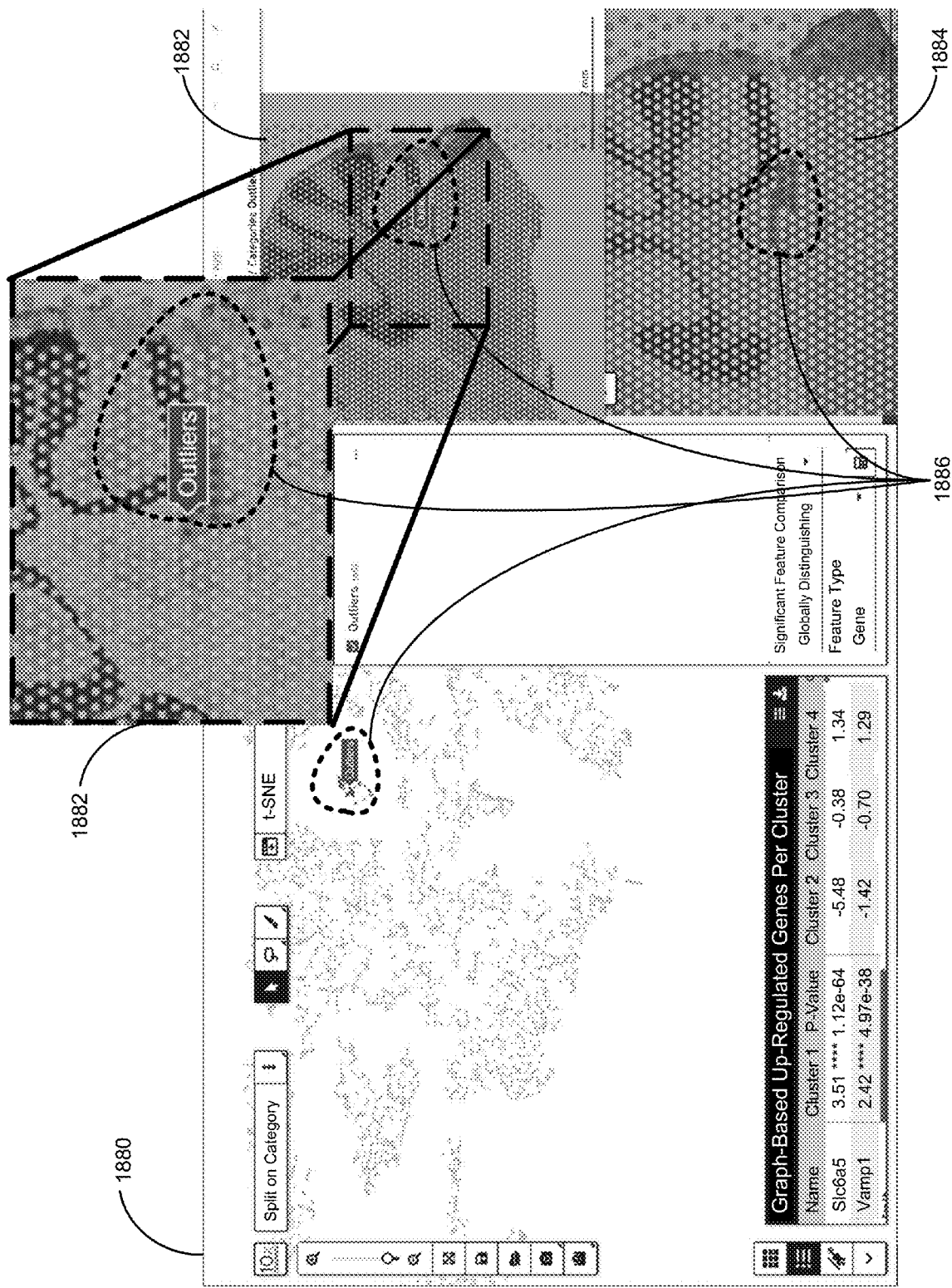

FIG. 18F illustrates how linked windows can advantageously lead to rapid analysis. FIG. 18F illustrates a t-SNE plot 1880 that represents the dimensionality reduction over two spatial projections 121 (SR-CUSTOM-22 1882 and SR-CUSTOM-24 1884) within a particular discrete attribute dataset 120. There is a visual cluster 1886 in the t-SNE (Outliers/C1) that the automatic clustering did not differentiate. Cluster 1886 contains a mix of probe spots assigned to different graph-based and K-means clusters. After selecting custom cluster 1886 in the anchor window (t-SNE view 1880), it is possible to see which regions it corresponds to in the two spatial projections 1882/1884 in the other linked windows. Zooming into each region between the two spatial projections 1882/1884 shows that there is common, tubular morphology under all spatial spots that are members of cluster 1886. There are also a variety of significant genes associated with these regions. In this manner, the present disclosure advantageously concurrently displays information from the gene expression-based projection (t-SNE plot 1880) to detect potentially interesting regions in the spatial context (SR-CUSTOM-22 1882 and SR-CUSTOM-24 1884). Using linked windows avoids having to jump back and forth, making the investigation fluid and intuitive.

While linked windows have been illustrated in conjunction with showing mRNA-based UMI abundance overlayed on source images, they can also be used to illustrate the spatial quantification of other analytes, either superimposed on images of their source tissue or arranged in two-dimensional space using dimension reduction algorithms such as t-SNE or UMAP, including cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). For general disclosure on how such analytes are spatially quantified, see, U.S. Provisional Patent Application No. 62/980,073, entitled "Pipeline for Analysis of Analytes," filed Feb. 21, 2020, which is hereby incorporated by reference. For general disclosure on how ATAC is spatially quantified using, for example clustering and/or t-SNE (where such cluster and/or t-SNE plots can be displayed in linked windows), see, United States Publication No. US-2020105373-A1 entitled "Systems and Methods for Cellular Analysis Using Nucleic Acid Sequencing" which is hereby incorporated by reference. For general disclosure on how V(D)J sequences are spatially quantified using, for example clustering and/or t-SNE (where such cluster and/or t-SNE plots can be displayed in linked windows), see, U.S. patent application Ser. No. 15/984,324, entitled "Systems and Methods for Clonotype Screening," filed May 19, 2018, which is hereby incorporated by reference.

In some embodiments, as illustrated in FIG. 7, the one or more data projections are used to render the spots in the correct size, in the correct position relative to the underlying tissue image. Cluster assignments are not location-aware. Instead, in some embodiments, clusters are determined only by applying Louvain modularity or K-means clustering to the values of the feature-barcode matrix. Despite this, the clusters in FIGS. 4 and 7 are still broadly divided into coherent shapes corresponding to different regions of the subject tissue.

Figure 8:
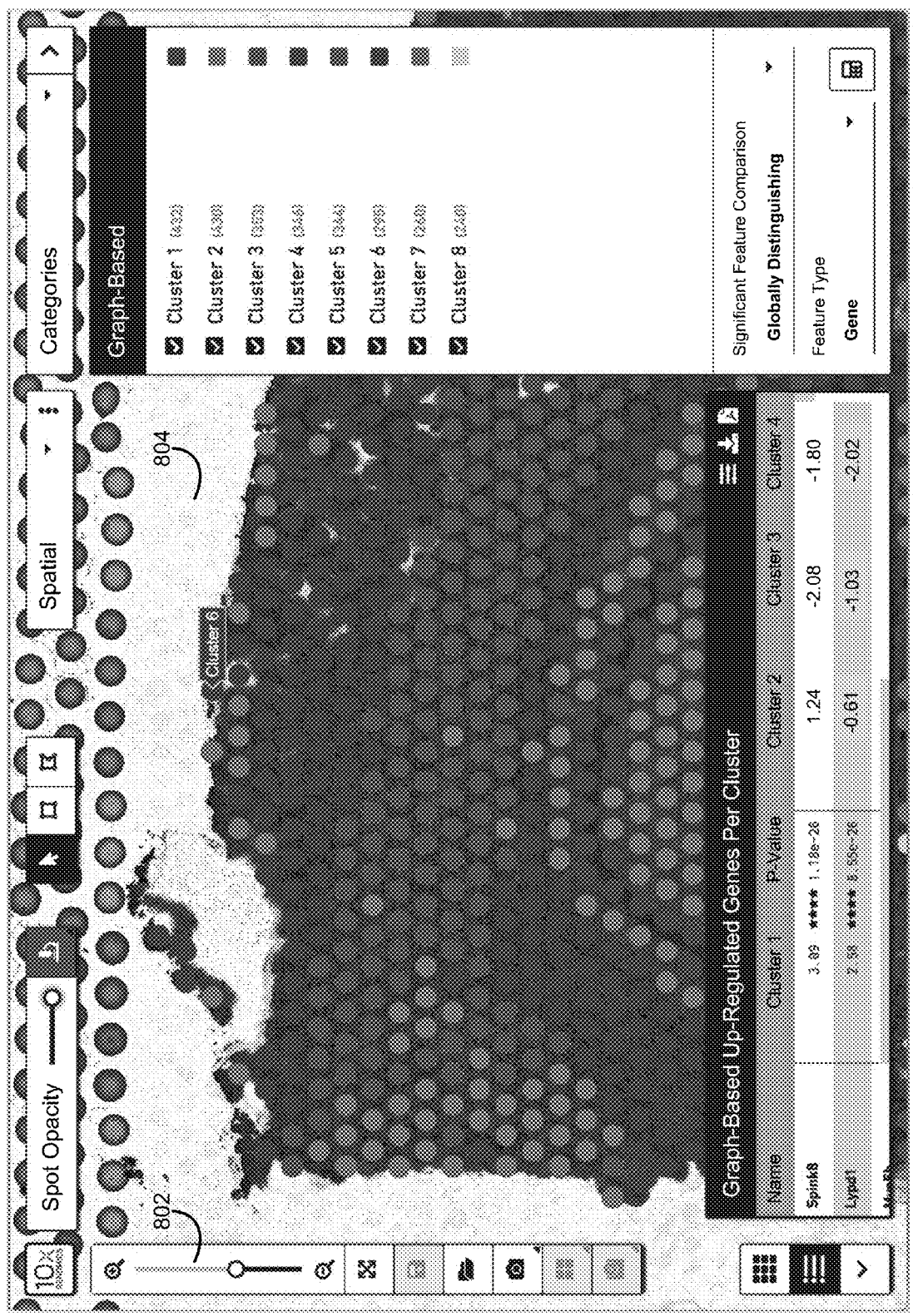
FIG. 8 illustrates an example of a close-up (e.g., zoomed in) of a region of the probe spot panel of FIG. 7, in accordance with some embodiments of the present disclosure.

In some embodiments, a respective user selection (e.g., a zooming input) results in zooming the spatial analysis view into a region of the tissue (see e.g., FIG. 8, which illustrates a zoomed-in region of FIG. 7). In some embodiments, the user selection comprises adjusting the zoom slider 802 (e.g., see the difference in the sizes of the plurality of probe spots between panels 704 and 804) and loading the appropriate tile corresponding to the desired location on the image. For discrete attribute value datasets 120 that have multiple images in a spatial projection (e.g., fluorescent, multichannel datasets), image tiles are retrieved based on the zoom level (of zoom slider 802) and position of the viewer with tiles retrieved for each active image (channel) concurrently. The images from the different channels are then composited together. In some embodiments, the displayed size of each probe spot in the plurality of probe spots is dynamically altered after the adjustment of the zoom slider 802 is complete, to always reflect the approximate location and diameter of the spots relative to the original tissue image (see panel 804 in FIG. 8). In some embodiments, a panning input and/or a zooming user input will trigger the loading of the appropriate tile. This enables visualization of the image at much higher resolution without overloading visualization module 119 memory with off-canvas image data (e.g., with regions of the original image that are not being presented to the user).

In some embodiments, the probe spot sizes dynamically change after the zoom motion is complete, to reflect the approximate location and diameter of the probe spots relative to the original tissue image. In some embodiments, panning and zooming user inputs also trigger loading of a respective tile corresponding to a desired location in the image. Thus, an image (or set of images) can be viewed at much higher resolutions without overloading visualization module 119 memory with off-canvas image data.

In some embodiments, one or more image settings can be adjusted. For example, in FIG. 9A, selection of an image settings affordance (e.g., microscope icon 902) provides for user selection of one or more image settings (e.g., brightness, contrast, saturation, rotation, etc.). In some embodiments, a user can flip the image horizontally, rotate it to its natural orientation via slider or by entering the number of degrees of rotation, and adjust brightness and saturation of the image. In some embodiments, to see the underlying details of the tissue, a user makes a selection to adjust probe spot opacity. For example, in FIG. 9A, a spot opacity slider 904 provides for increasing or decreasing the transparency of the plurality of probe spots. This permits a user to explore and determine an appropriate balance of feature information (e.g., as illustrated by the probe spots) combined with underlying image information, as described above.

Figure 17B:
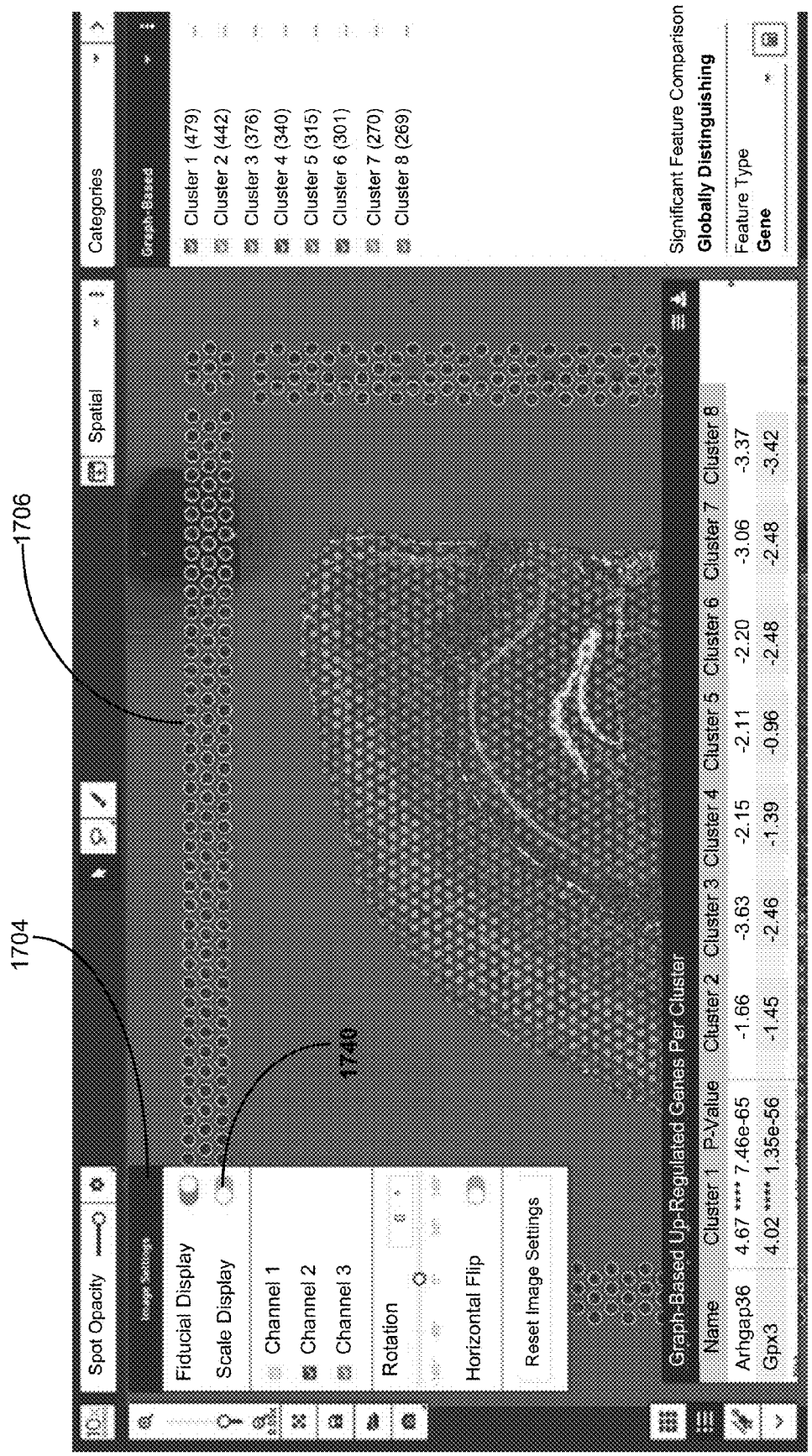
Figure 17C:
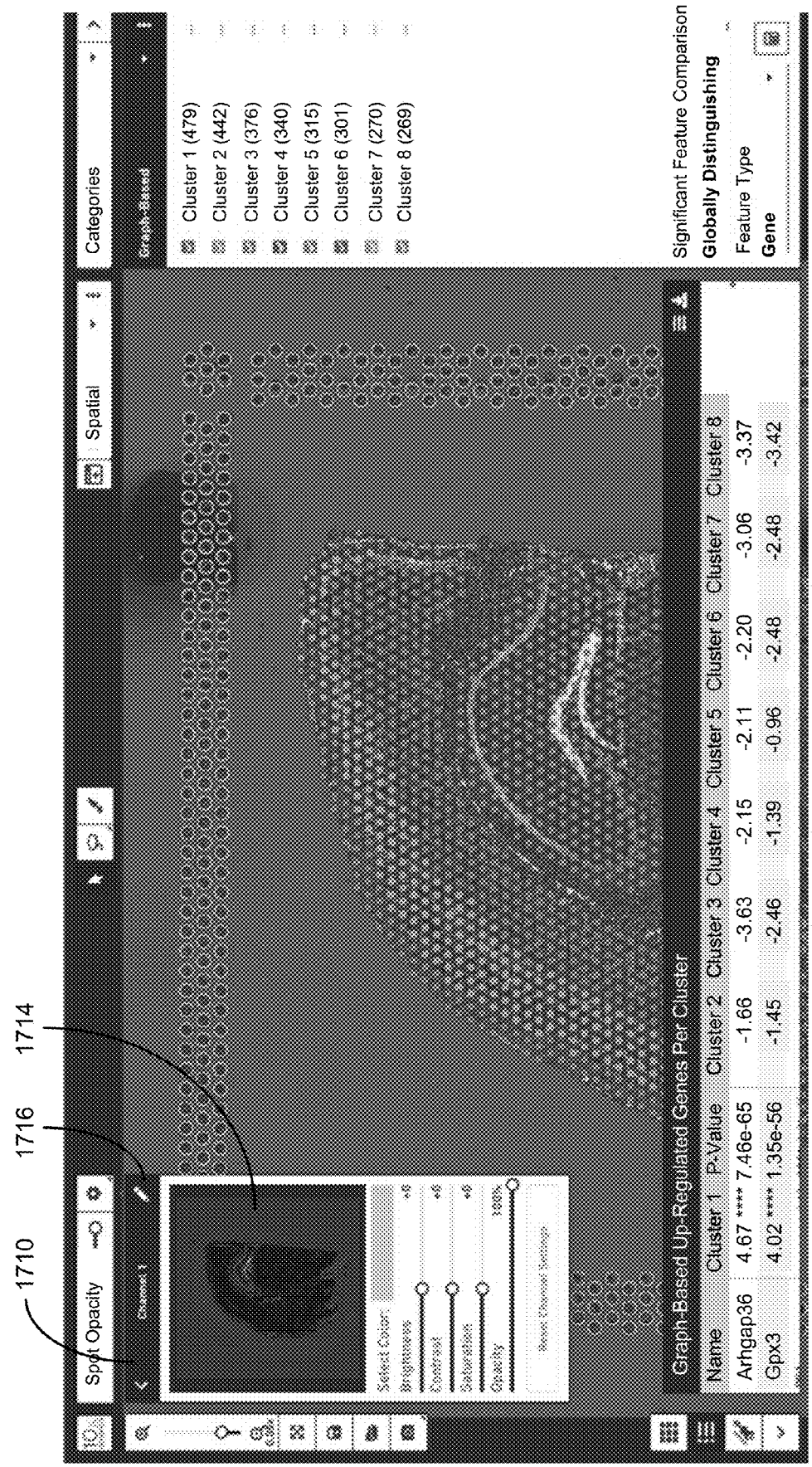

With reference to FIG. 17A, for spatial projections 121 of a multichannel discrete attribute dataset 120 that include multiple images (channels) 125 of the same tissue sample, the user may individually change parameters associated with each channel 125 using affordance 1702. That is, selection of affordance 1702 activates menu 1704 that displays all the images 125 of a given spatial projection 121. In the spatial projection 121-1 displayed in FIG. 17A, there are three images (channels) 125-1-1, 125-1-2, and 125-1-3. Moreover, the user may toggle on and off the spatial projections using affordance 1702 of menu 1704 as illustrated by comparison of FIGS. 17A (fiducial display off) and 17B (fiducial display 1708 on). As illustrated in FIG. 17B, the fiducial display is in the form of white circles around the fiducial spots of the image. Returning to FIG. 17A, selection, for example, of channel 125-1-1 by clicking on "Channel 1" in menu 1704 brings menu 1710 of FIG. 17C, where the user specifies a color to artificially shade the underlying fluorescent image pixels associated which channel 125-1-1 that, in some embodiments, is monochromatic/grayscale by default. As illustrated in menu 1710 of FIG. 17C, the user can change the color, brightness, contrast, saturation and opacity of channel 125-1-1 or restore these parameters to default settings and view the results of these changes to the channel 125-1-1 in preview window 1714. In other words, when editing the image settings of a single channel using menu 1710, a user can see how those changes affect that channel only in preview window 1714. This is especially helpful to see changes to that single channel when all channels are active. Returning to FIG. 17A, menu 1702 can be used to similarly change the above-disclosed parameter settings of all the other images 125. The images from the different channels are then composited together as illustrated in FIG. 17A. The net effect is that a user may specify different colors, brightness and opacities to achieve the desired balance between different channels, and emission wavelengths/colors of the stains used. Referring to FIG. 17, each channel (image 125) can be renamed using its corresponding parameters menu 1710 (e.g., by clicking on the pencil icon 1716 to the right side of the menu 1710 in FIG. 17C).

Moreover, using menu 1702, the individual images (channels) 125 contributing to the composite image can be individually turned off so that they do not contribute to the composite image using toggles 1712 (and individually turned on). For example, FIG. 17D shows channel 125-1-1 disabled.

Figure 17D:
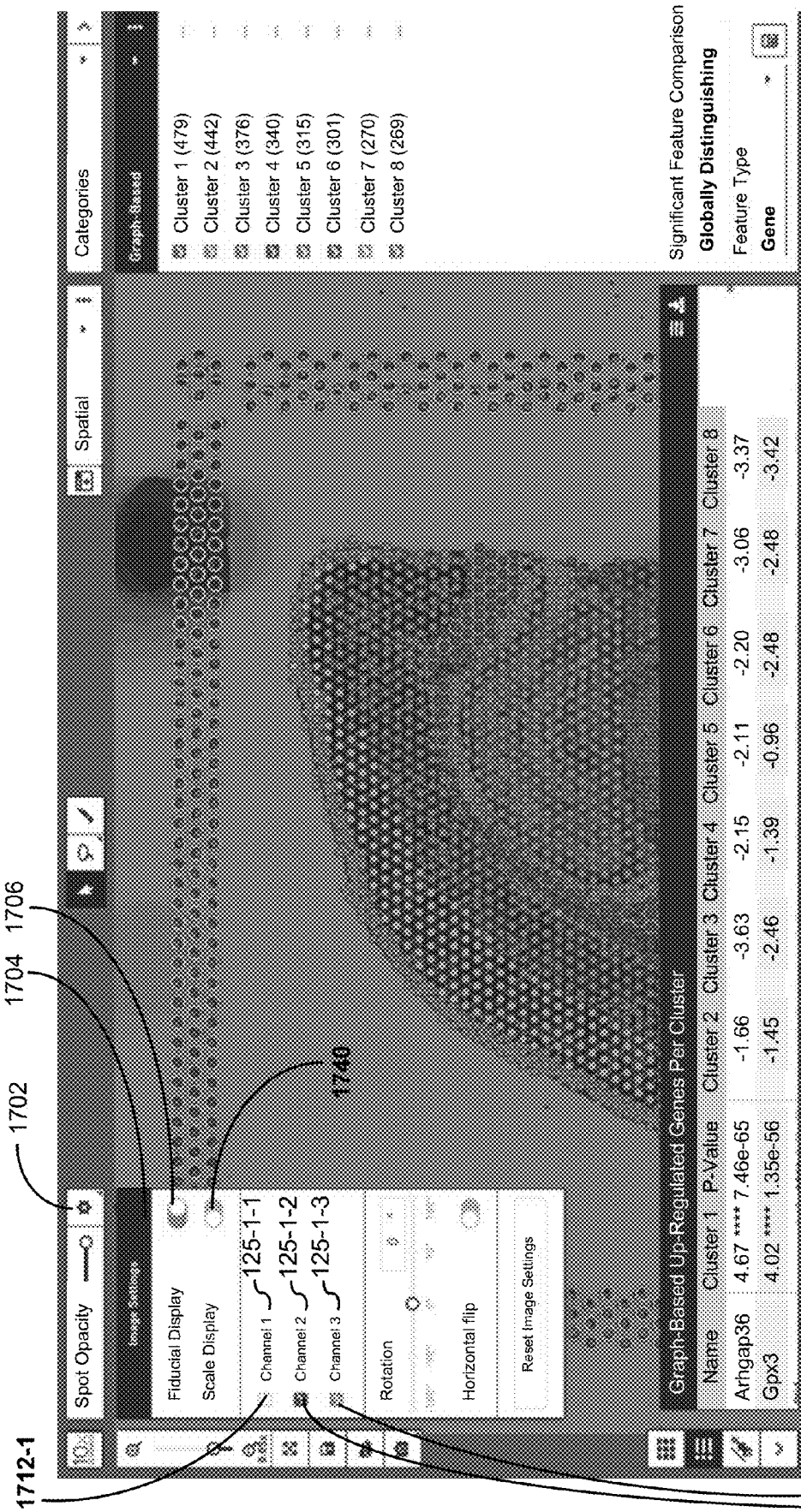

FIGS. 17A and 17D further show controls that affect the entire projection 121 and thus each image channel 125 together, such as rotation 1720 and flipping 1722. Affordance 1740 of menu 1704 (e.g., as illustrated in FIG. 17D) enables or disables the scale graphic (e.g. graphic 1750 of FIG. 17E), which shows the actual dimensions of the underlying image. Scale graph 1750 scales dynamically with zoom 1752.

Figure 17E:
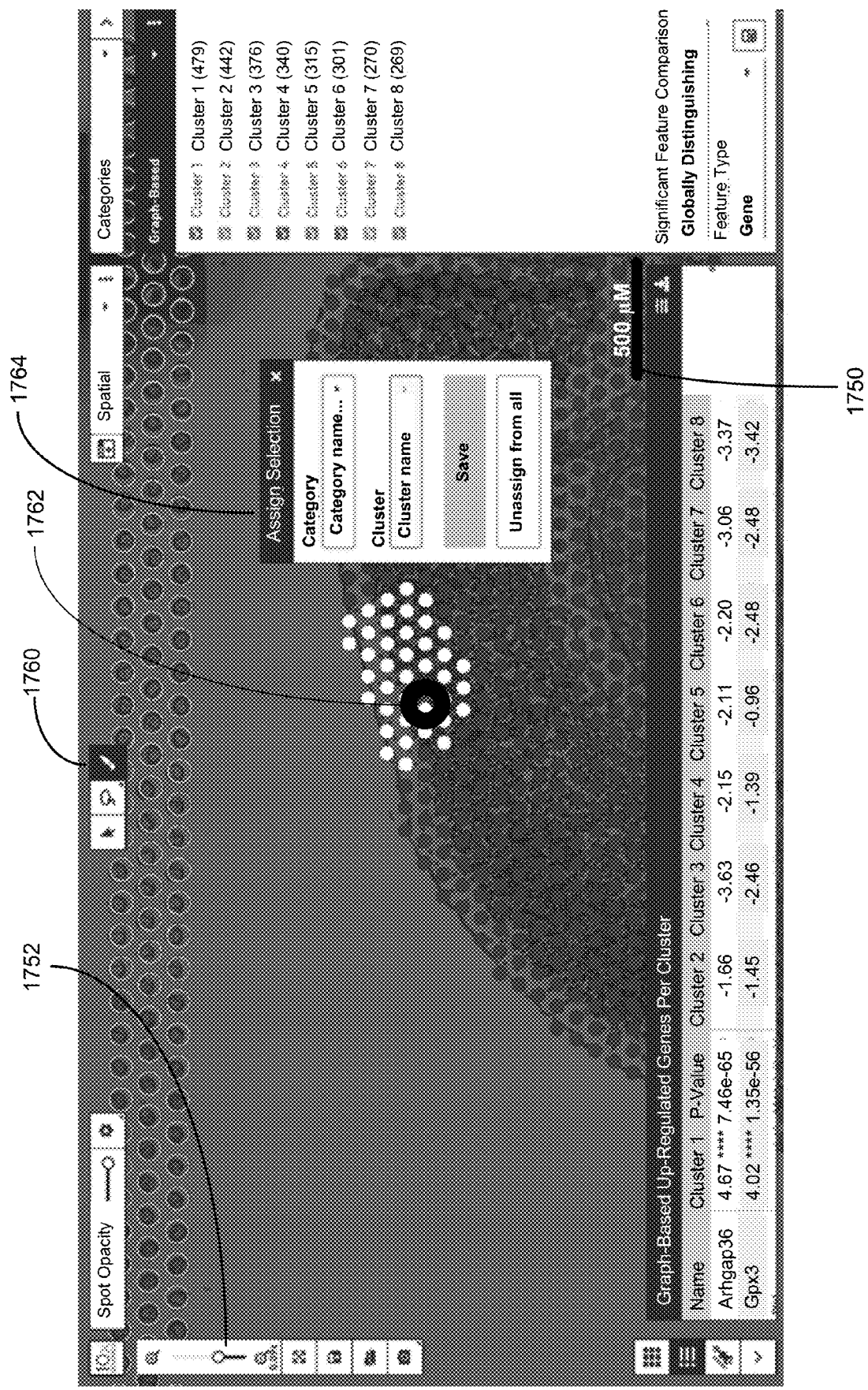

FIG. 17E shows another way to more precisely select spots in a spatial context. When the paintbrush mode is selected by clicking on the paintbrush affordance 1760, a user may hold down and drag the mouse cursor over spots 172 to select them and assign them to clusters using menu 1764. This allows more precise control of image morphology-based cluster creation. The spots that are selected are any that fall under the mouse cursor 1762 as the user moves the cursor. To select spots for the same cluster that are not near each other in the image or are not contiguous in the image, the user can select some of the spots, release the cursor thereby activating menu 1764, assign the selected spots to a particular category and then use paintbrush 1760 to select additional spots from the non-contiguous region, once again release the cursor 1762 thereby activating menu 1764 and use the menu 1764 to assign the second set of spots to the same category. Alternatively, the user can assign the second batch of selected spots to a different category from the first selected batch of spots. In this way, the user can select as many spots for as many different categories. Each time the user releases the cursor 1762 and moves it to a new location, all prior selected mouse spots are deselected.

Figure 10:
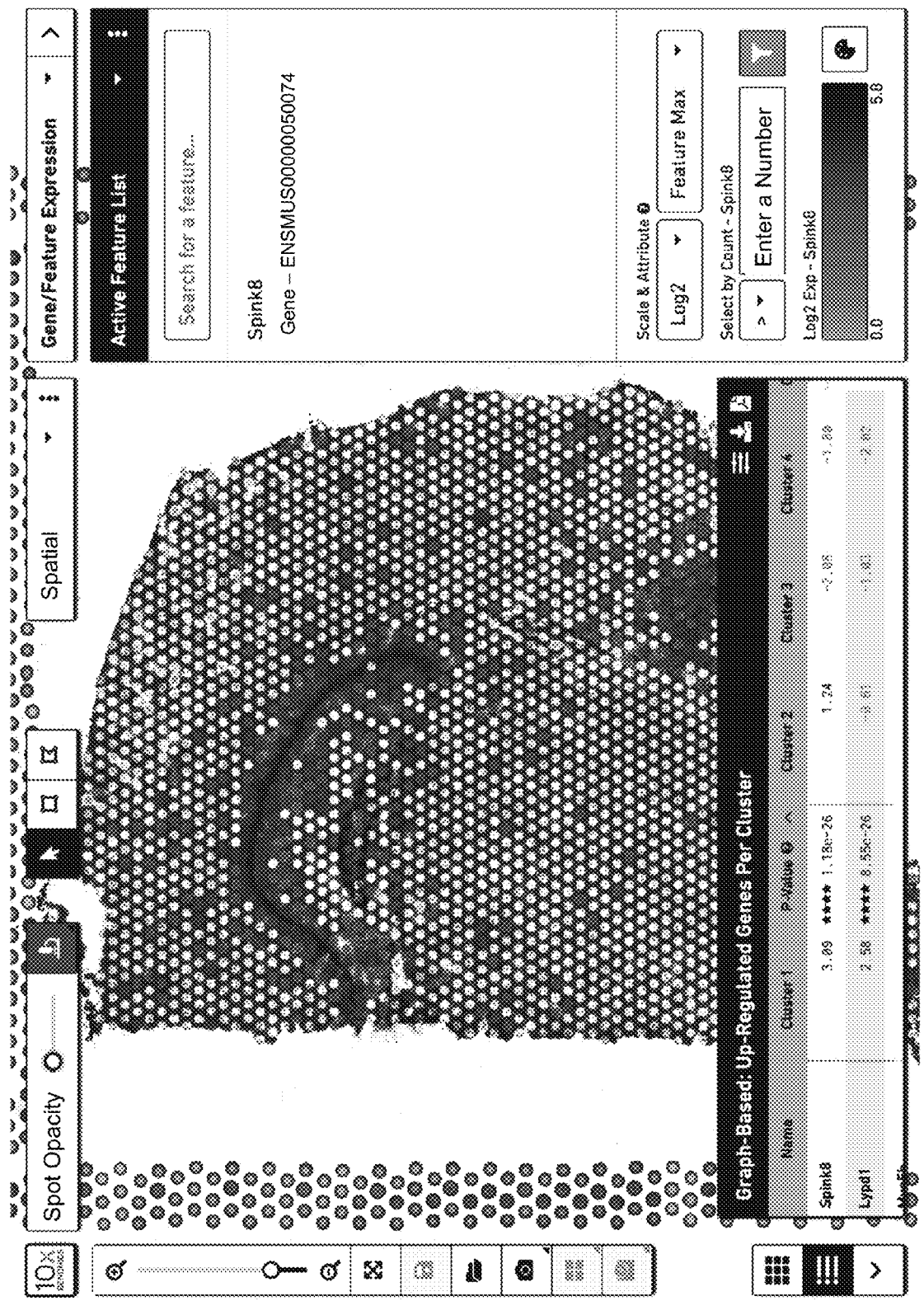
FIG. 10 illustrates selection of a single gene for visualization, in accordance with some embodiments of the present disclosure.

In some embodiments, each discrete attribute file dataset 120 includes information identifying one or more significant features (e.g., gene expression, feature barcode analyte count, etc.) corresponding to each cluster in the plurality of clusters. For example, in FIG. 10, a user has selected a single gene (e.g., 'Spink8'). The selection of Spink8 results in display of the expression of this gene within the image (e.g., for each probe spot in the plurality of displayed probe spots). The expression of this gene is clearly highlighted in the resulting image. Thus, users can clearly view the correlation of the expression of particular features overlaid on the underlying image file.

Figure 11A:
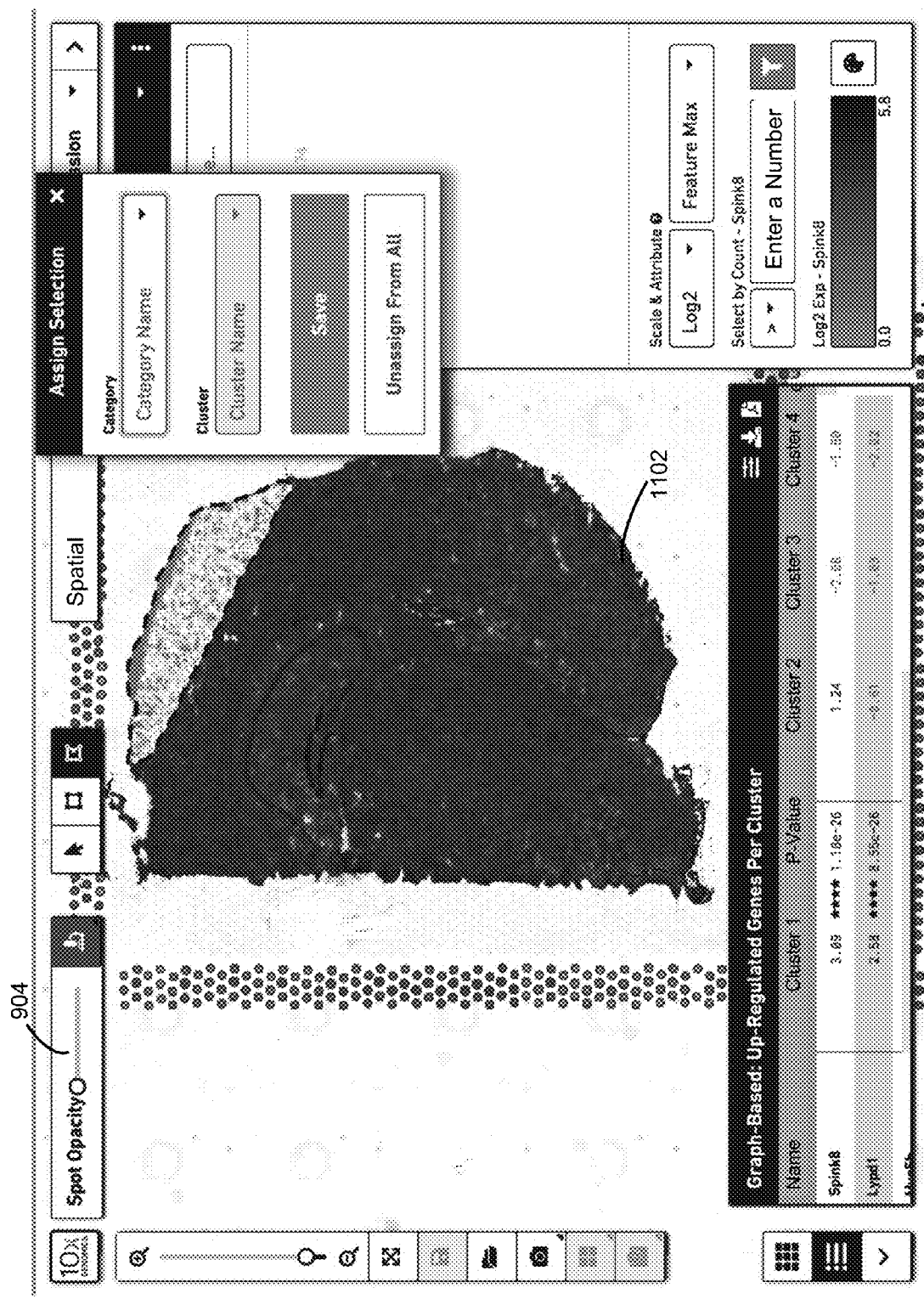
FIGS. 11A and 11B illustrate adjusting the opacity of the probe spots overlaid on an underlying tissue image and creating one or more custom clusters, in accordance with some embodiments of the present disclosure.
Figure 11B:
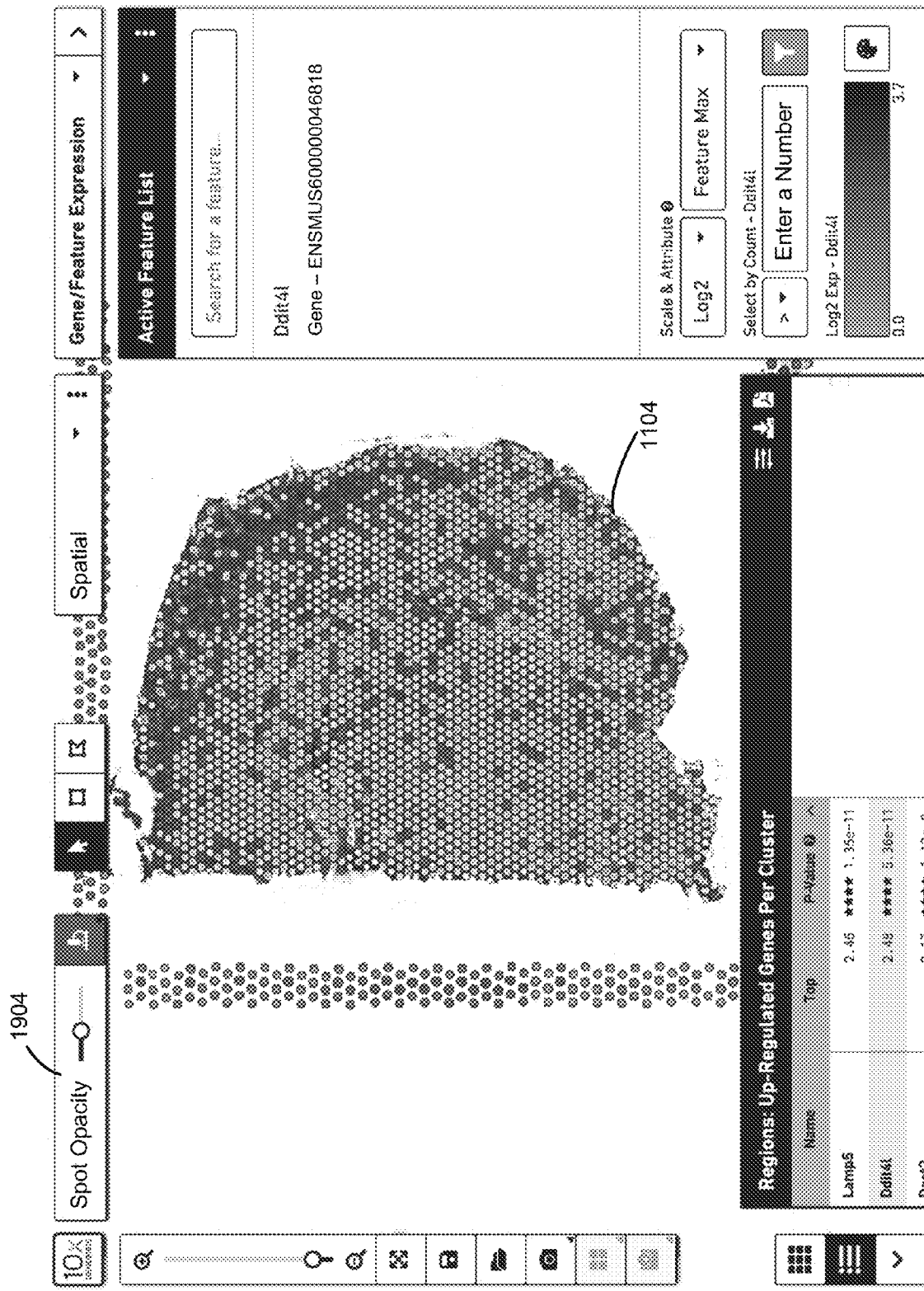

In some embodiments, low probe spot opacity (e.g., as shown in FIG. 11A in spot opacity bar 904) permits visualization of an underlying image file (or set of images files) without any interaction with feature display, which is desirable to view aspects of the tissue itself (e.g., region 1102 represents the tissue sample). FIG. 11B illustrates increased spot opacity (e.g., as seen in spot opacity bar 904), combined with feature information (e.g., here gene expression of 'Ddit4l'). For example, a plurality of probe spots can be seen in region 1104 in FIG. 11B. Switching between the views in FIGS. 11A and 11B enables discovery of patterns of gene expression alongside tissue features in an interactive manner.

Figure 12A:
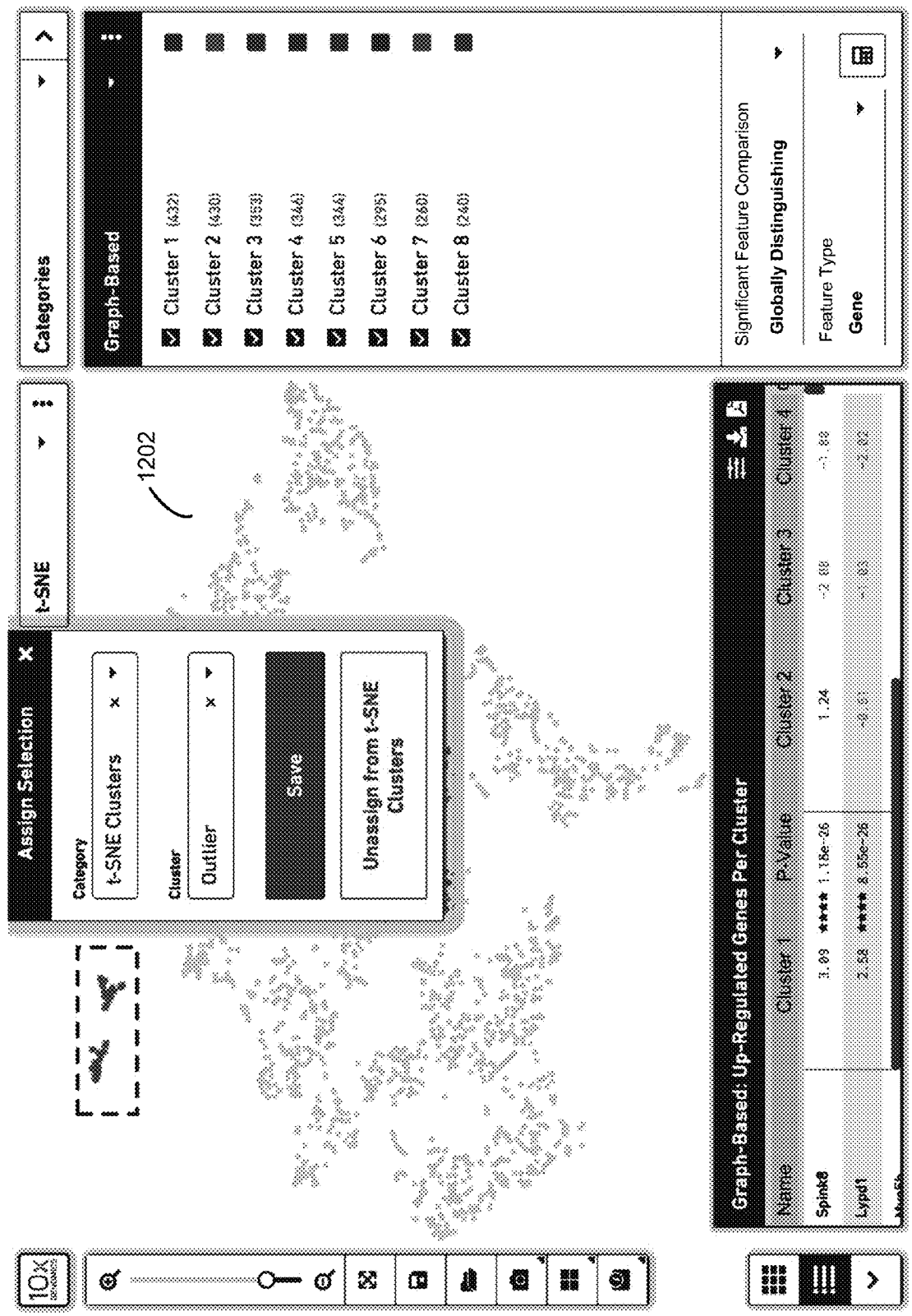
FIGS. 12A and 12B collectively illustrate clusters based on t-SNE and UMAP plots in either computational expression space as shown in FIG. 12A or in spatial projection space as shown in FIG. 12B, in accordance with some embodiments of the present disclosure.
Figure 12B:
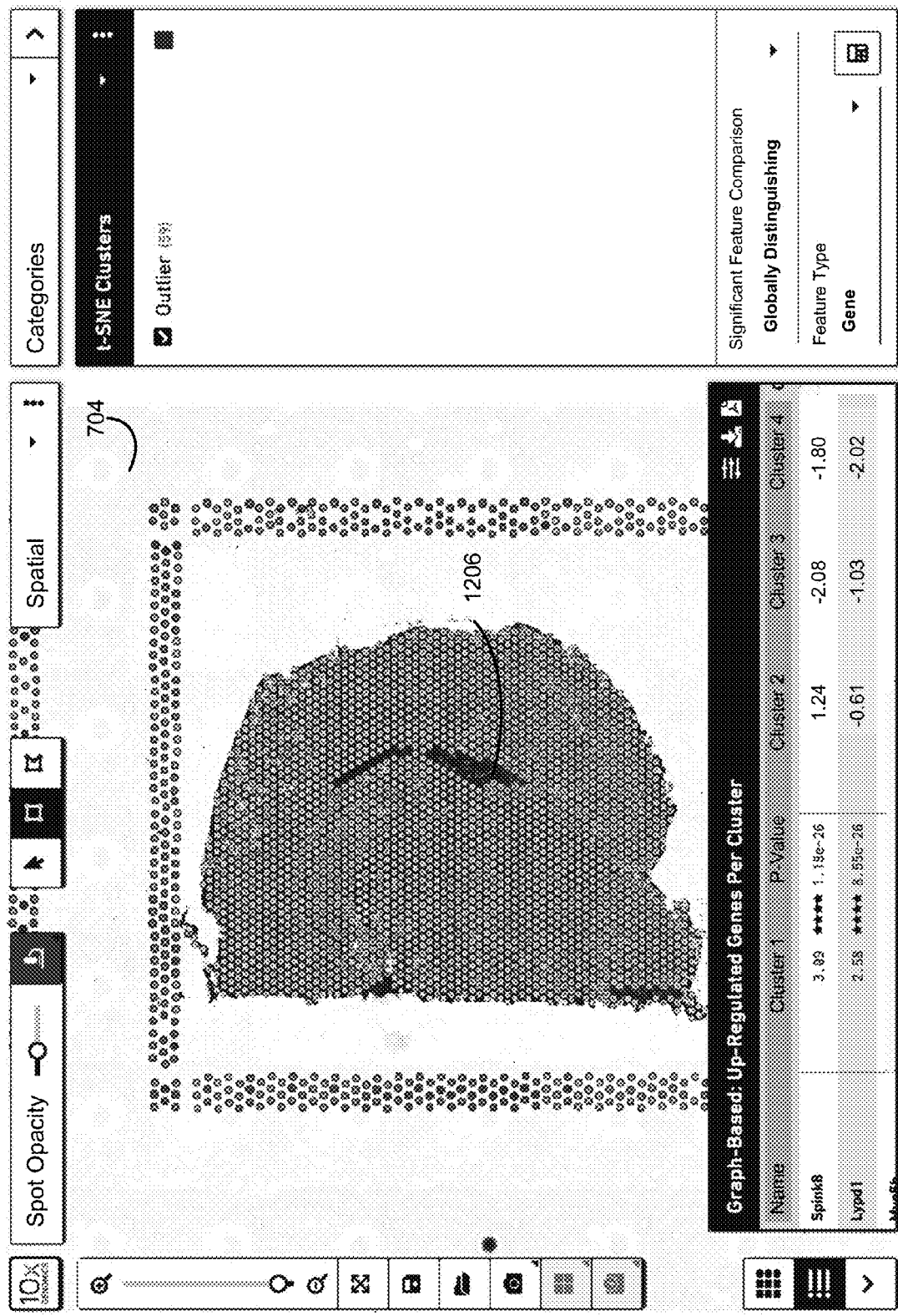

In some embodiments, as shown in FIG. 12A, a projection of probe spot expression information into t-SNE space is provided. In some embodiments, a projection of probe spot expression into UMAP space can also be shown. Such projections illustrate one or more clusters. As described above with regard to other embodiments of the present disclosure, a single cluster (e.g., 'Outliers') can be selected and displayed in either the t-SNE projection space (e.g., region 1202 of FIG. 12A) or in the spatial analysis view panel 704 (e.g., region 1206 in FIG. 12B).

In some embodiments, image display, manipulation, and export are performed as described in U.S. patent application Ser. No. 15/681,290, entitled "Providing Graphical Indication of Label Boundaries in Digital Maps," filed Aug. 18, 2017 or U.S. patent application Ser. No. 15/681,286, entitled "Providing Visual Selection of Map Data for a Digital Map," filed Aug. 18, 2017, which are hereby incorporated by reference.

Embodiments in which Additional Feature Data is Stored and Visualized

Figure 15A:
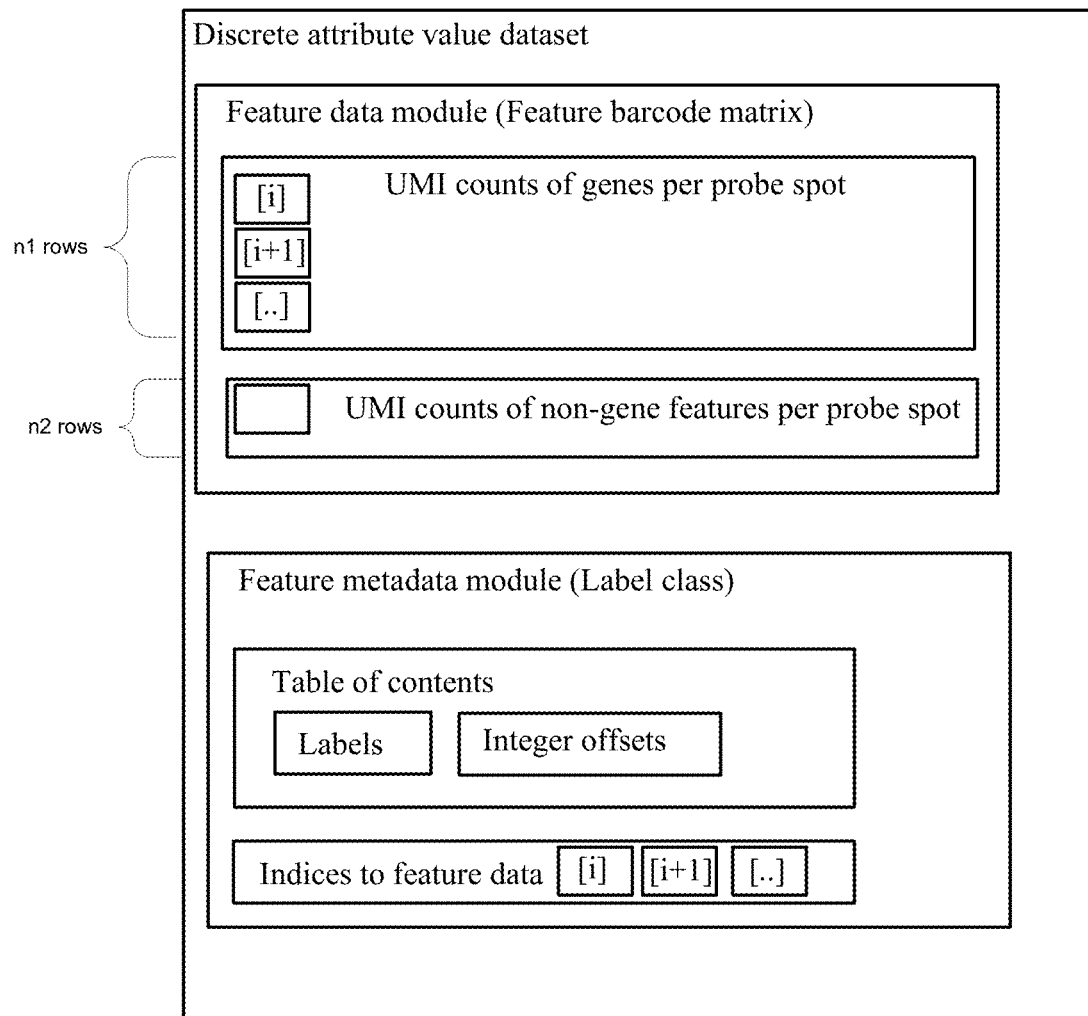
FIG. 15A is a block diagram illustrating a discrete attribute value dataset in accordance with some embodiments of the present disclosure.

In some embodiments, the discrete attribute value dataset 120 (e.g., .cloupe file) stores feature data (read counts) and feature metadata separately, and the feature metadata is stored in a serialized data structure, as shown in FIG. 15. Such a data storage format increases computational efficiency. In particular, FIG. 15 illustrates a discrete attribute dataset for a gene expression pipeline, capable of counting gene and non-gene features per probe spot, that includes a feature data module storing UMI counts per gene per probe spot and UMI counts of non-gene features (e.g., bound antibodies) per probe spots. A feature metadata module, also referred to herein as a "label class," identifies a type of each row the matrix. In some embodiments, as shown in FIG. 15, the feature metadata module is stored on disk as two entities—a table of contents and an indices module. The table of contents includes a labels module (which can store, e.g., an array of labels) and an integer offsets module (which can store, e.g., an array of integer offsets). The indices module can be in the form of a continuous array of indices, where each index in the array (e.g., indices i, i+1, etc.) refers to indices of rows in the feature data storage.

For example, in some embodiments, the feature data module includes an antibody dataset having n1 of rows representing a number (n1, in this example) of UMI counts per gene per probe spot and subsequent n2 rows of representing a number (n2, in this example) of UMI counts of certain one or more bound antibodies in each probe spot. As an example, the antibody dataset can include 20,000 rows representing UMI counts per gene per probe spot (e.g., n1=20,000) and subsequent 17 rows representing the UMI counts of the bound antibody per each probe spot (e.g., n2=17). In this example, the table of contents defines the labels as "Labels: ["Gene", "Antibody"]" and the integer offsets as "Offsets: [0, 20000]." The integer offsets indexes into a contiguous array of 20,017 feature row indices in the indices module. The range of feature row indices corresponding to genes starts at array position 0, and the indices for the antibody start at the position 20,000. The indices module, in this example, can be integers from to n1-1 in the ascending order, where n1 is the number of rows in the feature data module. The table of contents module can be stored in any suitable format. For example, in some embodiments, it can be a compressed JSON string and information stored in the table of contents can be in the form of CSC and CSR indices and data. Such approaches increase computational efficiency. For instance, representation of labels for two different types of loci in this manner improves the computational efficiency of visualization system 100, in part, by reducing the amount of data that needs to be processed in order to visualize the data for the loci of the first type and the loci of the second type.

In some embodiments, the spatial analysis pipeline is configured to generate clusters and/or t-SNE projections based on subsets of features in the discrete attribute dataset. In some such embodiments, discrete attribute values related to select genes in the feature-barcode matrix are used to determine clusters and create a t-SNE projection, and discrete attribute values related to the select genes are used to construct a different projection.

To generate additional projections in the pipeline, in some embodiments, a configuration file is specified that identifies the barcode sequence corresponding to a feature barcode, its type, as well as additional metadata. It will be appreciated that such feature barcodes are for the plurality of loci of the second class and thus are separate and apart from the barcodes for the plurality of loci of the first class.

Figure 15B:
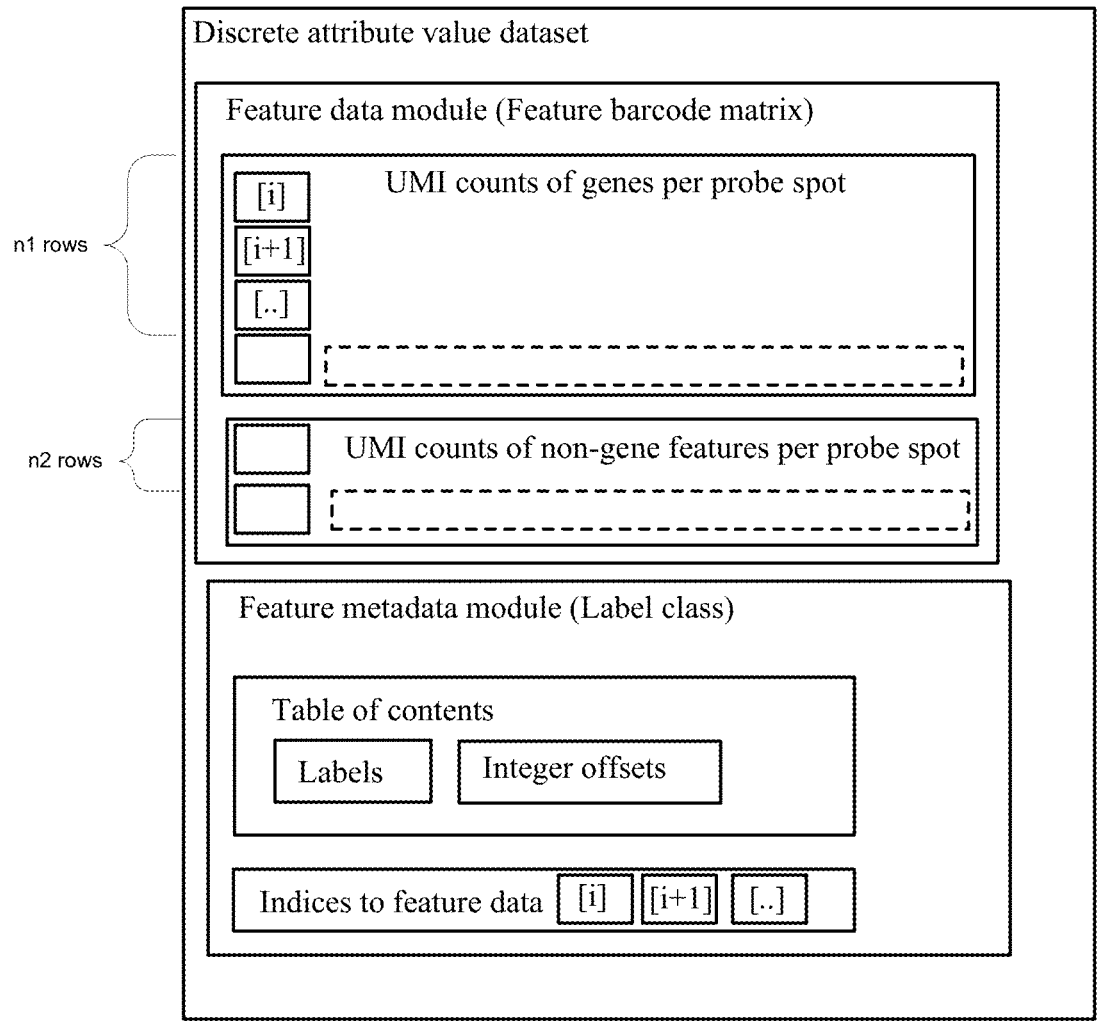
FIG. 15B is another block diagram illustrating the discrete attribute value dataset of FIG. 15A, where aggregate rows are generated in accordance with some embodiments of the present disclosure.

In some embodiments, aggregate features are generated by combining features of the same or similar type. For example, referring to FIG. 15A, additional rows can be generated based on existing rows in the feature data, and these additional rows can be added to the feature data module. FIG. 15B illustrates schematically such additional rows that are shown with a dashed line. In some implementations of the present disclosure, feature rows with similar metadata are combined to generate additional feature rows. For example, in an example where there are 20,000 gene data rows per probe spot and 17 antibody data rows per probe spot, an aggregate gene data row can be generated by combining the 20,000 gene data rows and an aggregate antibody data row can be generated by combining the 17 antibody data rows. In some embodiments, when each row includes respective gene counts per probe spot or antibody counts per probe spot, the respective gene counts and antibody counts can be summed to generate respective aggregate gene count row and aggregate antibody count (or some other feature) row. It should be appreciated, however, that the gene data rows, antibody data rows, or rows storing data for any other types of features can be combined in other ways that can be different from a summation operation. Furthermore, in some cases, a portion of the rows (e.g., in the above example, less than 20,000 gene data rows) in the feature data module can be combined. Regardless of the way in which multiple rows having similar metadata are combined, the resulting aggregate rows can be stored in compressed form (e.g., compressed sparse row (CSR) and compressed sparse matrix (CSC) formats). This advantageously improves computer efficiency. The locations of the aggregate rows are stored in the feature metadata module. In some embodiments, aggregating feature rows having similar metadata (e.g., counts of a particular feature per probe spot) allows for the derivation of a normalized, relative expression for that particular feature.

Example 1

Figure 6:
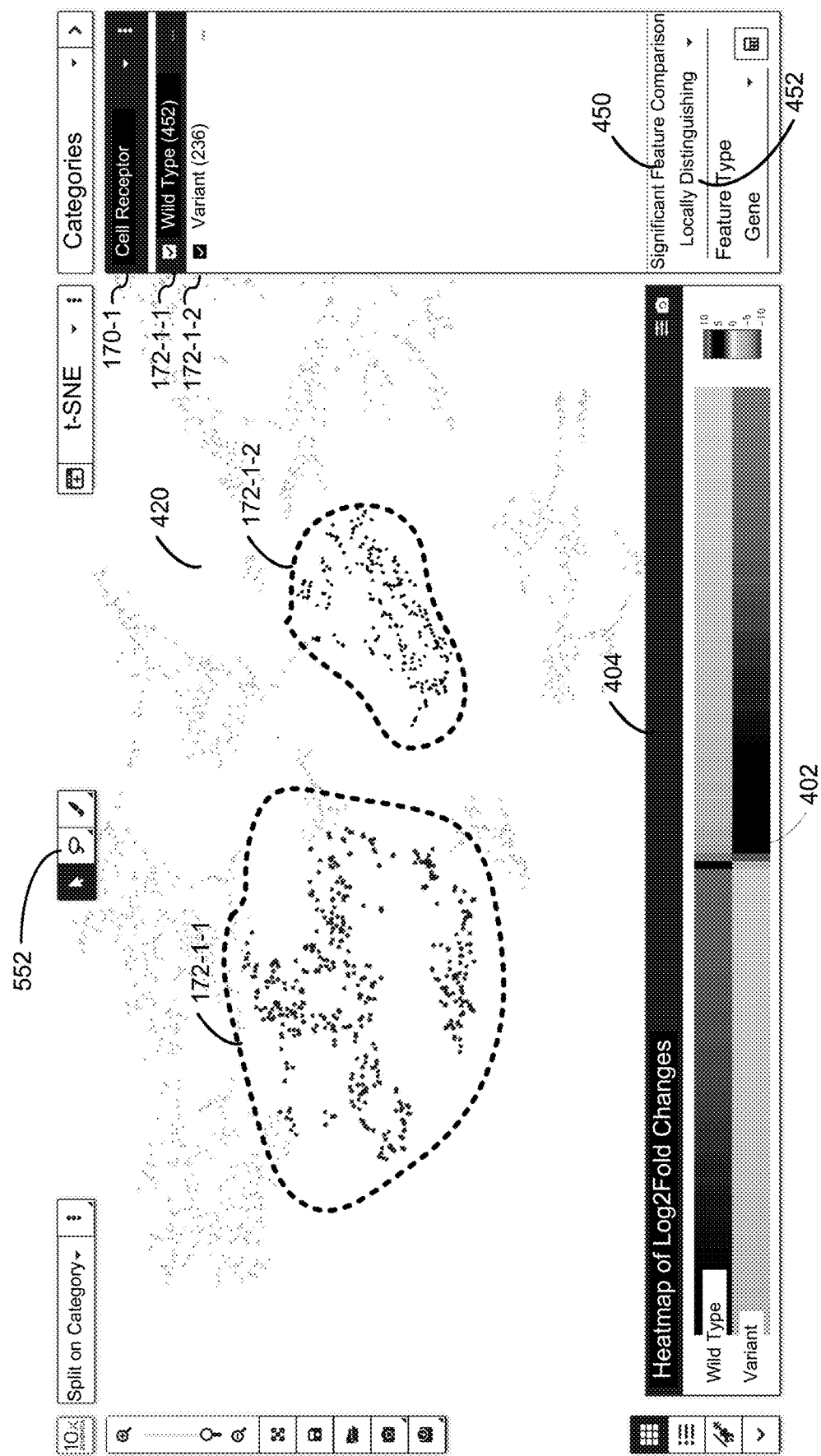
FIG. 6 illustrates the user selection of classes for a user-defined category and the computation of a heat map of $\log_2$ fold changes in the abundance of mRNA transcripts mapping to individual genes, in accordance with some embodiments of the present disclosure.

Referring to FIG. 6, an example visualization system 100 comprising a plurality of processing cores, a persistent memory, and a non-persistent memory was used to perform a method for visualizing a pattern in a dataset. In this example, the example visualization system 100 was a DELL Inspiron 17 7000 with MICROSOFT WINDOWS 10 PRO, 16.0 gigabytes of RAM memory, and Intel i7-8565U CPM operating at 4.50 gigahertz with 4 cores and 8 logical processors with the visualization module 119 installed. The discrete attribute value dataset 120, comprising a single spatial image 125 of a tissue sample with accompanying discrete attribute values 124 for hundreds of loci at each of hundreds of probe spots 126 was stored in persistent memory. The dataset was clustered prior to loading onto the example computer system 100, using principal components derived from the discrete attribute values across each locus in the plurality of loci across each probe spot 126 in the plurality of probe spots thereby assigning each respective probe spot in the plurality of probe spots to a corresponding cluster in a plurality of clusters. These cluster assignments were already assigned prior to loading the dataset into the example computer system 100. Each respective cluster in the plurality of clusters consisted of a unique different subset of the plurality of probe spots 123. For this example dataset 120, there were 8 clusters. Each respective cluster comprises a subset of the plurality of probe spots in a multi-dimensional space. This multi-dimensional space was compressed by t-SNE into two-dimensions for visualization in the upper panel 420.

Next, referring to FIG. 6, a new category, "Cell Receptor," that was not in the loaded discrete attribute value dataset 120 was user defined by selecting a first class of probe spots 172-1-1 ("Wild Type") using Lasso 552 and selecting displayed probe spots in the upper panel 420. A total of 452 probe spots 126 were selected from the Wild Type class. Further, a second class of probe spots 172-1-2 ("Variant") was user defined using Lasso 552 to select the probe spots as illustrated in FIG. 6. Next, the loci whose discrete attribute values 124 discriminate between the identified user defined classes "Wild Type" and "Variant" were computed. For this, the locally distinguishing option 452 described above in conjunction with FIG. 4 was used to identify the loci whose discrete attribute values discriminate between class 172-1-1 (Wild Type) and class 172-1-2 (Variant). The Wild Type class consisted of whole transcriptome mRNA transcript counts for 452 probe spots. The Variant class consisted of whole transcriptome mRNA transcript counts for 236 probe spots. To do this, the differential value for each respective locus in the plurality of loci for class 172-1-1 was computed as a fold change in (i) a first measure of central tendency of the discrete attribute value for the respective locus measured in each of the probe spots in the plurality of probes spots in the class 172-1-1 and (ii) a second measure of central tendency of the discrete attribute value for the respective locus measured in each of the probe spots in the class 172-1-2. Then the heat map 402 of this computation for each of the loci was displayed in the lower panel 404 as illustrated in FIG. 6. In heat map 402, the first row represents the Wild Type class and the second row represents the Variant class. Each column in the heat map shows the average expression of a corresponding gene across the probe spots of the corresponding class 172. The heat map includes more than 1000 different columns, each for a different human gene. The heat map shows which loci discriminate between the two classes. An absolute definition for what constitutes discrimination between the two classes is not provided because such definitions depend upon the technical problem to be solved. Moreover, those of skill in the art will appreciate that many such metrics can be used to define such discrimination and any such definition is within the scope of the present disclosure. Advantageously, the computation and display of the heat map 402 took less than two seconds on the example system using the disclosed clustering module 152.

Had more classes been defined, more computations would be needed. For instance, had there been a third class in this category and this third class selected, the computation of the fold change for each respective locus would comprise:

for the first class 172-1-1, computing (i) a first measure of central tendency of the discrete attribute value for the respective locus measured in each of the probe spots in the plurality of probe spots of the first class 172-1-1 and (ii) a second measure of central tendency of the discrete attribute value for the respective locus measured in each of the probe spots in the second 172-1-2 and third classes 172-1-3 collectively, for the second class 172-1-1, computing (i) a first measure of central tendency of the discrete attribute value for the respective locus measured in each of the probe spots in the plurality of probe spots of the second class 172-1-2 and (ii) a second measure of central tendency of the discrete attribute value for the respective locus measured in each of the probe spots in the first class 172-1-1 and the third class 172-1-3 collectively, and for the third class 172-1-3, computing (i) a first measure of central tendency of the discrete attribute value for the respective locus measured in each of the probe spots in the plurality of probe spots of the third class 172-1-3 and (ii) a second measure of central tendency of the discrete attribute value for the respective locus measured in each of the probe spots in the first class 172-1-1 and the second class 172-1-2 collectively.

Example 2

Triple negative breast cancer (TNBC) accounts for 10-20% of all diagnosed breast cancer cases in the United States. TNBC is aggressive and exhibits poor prognosis due to resistance to traditional therapies. TNBC is complex, making it important to understand the underlying biology to improve outcomes.

Spatial transcriptomics technology has helped address the limitations of traditional pathological examination, combining the benefits of histological techniques and massive throughput of RNA-seq. Serial sections of TNBC were investigated using the 10× Genomics Visium Spatial Gene Expression Solution disclosed in the present disclosure, and also disclosed in U.S. patent application Ser. No. 16/992,569, entitled "Systems and Methods for Using the Spatial Distribution of Haplotypes to Determine a Biological Condition," filed Aug. 13, 2020, which is hereby incorporated by reference, to resolve its tumorigenic expression profile. The assay in this example incorporates ~5000 molecularly barcoded, spatially encoded capture probes in probe spots 122 over which a tissue is placed, imaged, and permeabilized, capturing native mRNA in an unbiased fashion. Imaging and next-generation sequencing data were processed together resulting in gene expression mapped to image position. By capturing and sequencing of polyadenylated RNA transcripts from 10 μm thick sections of tissue combined with histological visualization of the tissue, the Visium platform generated an unbiased map of gene expression of cells within the native tissue morphology.

Through this, spatial patterns of gene expression were demonstrated that agreed with annotations from pathological examination combined with immunohistochemical staining for tumor infiltrating lymphocytes, a hallmark of TNBC. By aggregating data from serial sections, the delineation of gene expression patterns was improved and furthermore, improved statistical power for cell-type identification was demonstrated. This data was compared with 3' single-nucleus RNA-seq data from the same sample, generating cell-type expression profiles that were used to estimate the proportion of cell-types observed at a given position. Furthermore, an enrichment strategy was used to select for cancer-associated genes using the cancer probes of Table 1 of U.S. Provisional Patent Application No. 62/979,889, entitled "Capturing Targeted Genetic Targets Using a Hybridization/Capture Approach," Feb. 21, 2020. The spatial patterns of gene expression using this pull-down approach showed concordance with the whole transcriptome assay, suggesting that a targeted transcriptome sequencing approach can be used where a fixed gene panel is appropriate.

Results from these efforts suggest that spatial gene expression profiling can provide a powerful complement to traditional histopathology, enabling both targeted panels and whole-transcriptome discovery of gene expression. This detailed view of the tumor microenvironment, as it varies across the tissue space, provides essential insight into disease understanding and the development of potential new therapeutic targets.

Example 3

The gut microbiome, populated by trillions of microbes, interacts closely with the host's cell system. Studies have revealed information about the average microbiota diversity and bacterial activity in the gut. However, this study of expression-based host-microbiome interactions in a spatial and high-throughput manner is a novel approach. Understanding the cartography of gene expression of host-microbiome interactions provides insights into the molecular basis and the widespread understanding of bacterial communication mechanisms. Using the techniques disclosed herein and as also described in U.S. patent application Ser. No. 16/992,569, entitled "Systems and Methods for Using The Spatial Distribution of Haplotypes to Determine a Biological Condition," filed Aug. 13, 2020, which is hereby incorporated by reference, a spatial transcriptomics method was developed that enables visualization and quantitative analysis of gene expression data directly from tissue sections by positioning the section on a barcoded array matrix. With this approach, both polyadenylated host and 16S bacterial transcripts are concurrently transcribed in situ and the spatial cDNAs are sequenced. More than 11,000 mouse genes were concurrently analyzed and more than nine bacterial families in the proximal and distal mouse colon were identified as a pilot study. The processing pipelines of the present disclosure were applied to determine spatial variance analysis across the collected tissue volume. This approach generated a large cell-interaction dataset with the ability to call changes significantly occurring in multiple host cell types dependent on the nearby microbiome composition. These findings demonstrate the power of spatially resolved, transcriptome-wide gene expression analysis identifying morphological patterns and thus understanding the molecular basis of host-microbiome interactions.

Example 4

Figure 20:
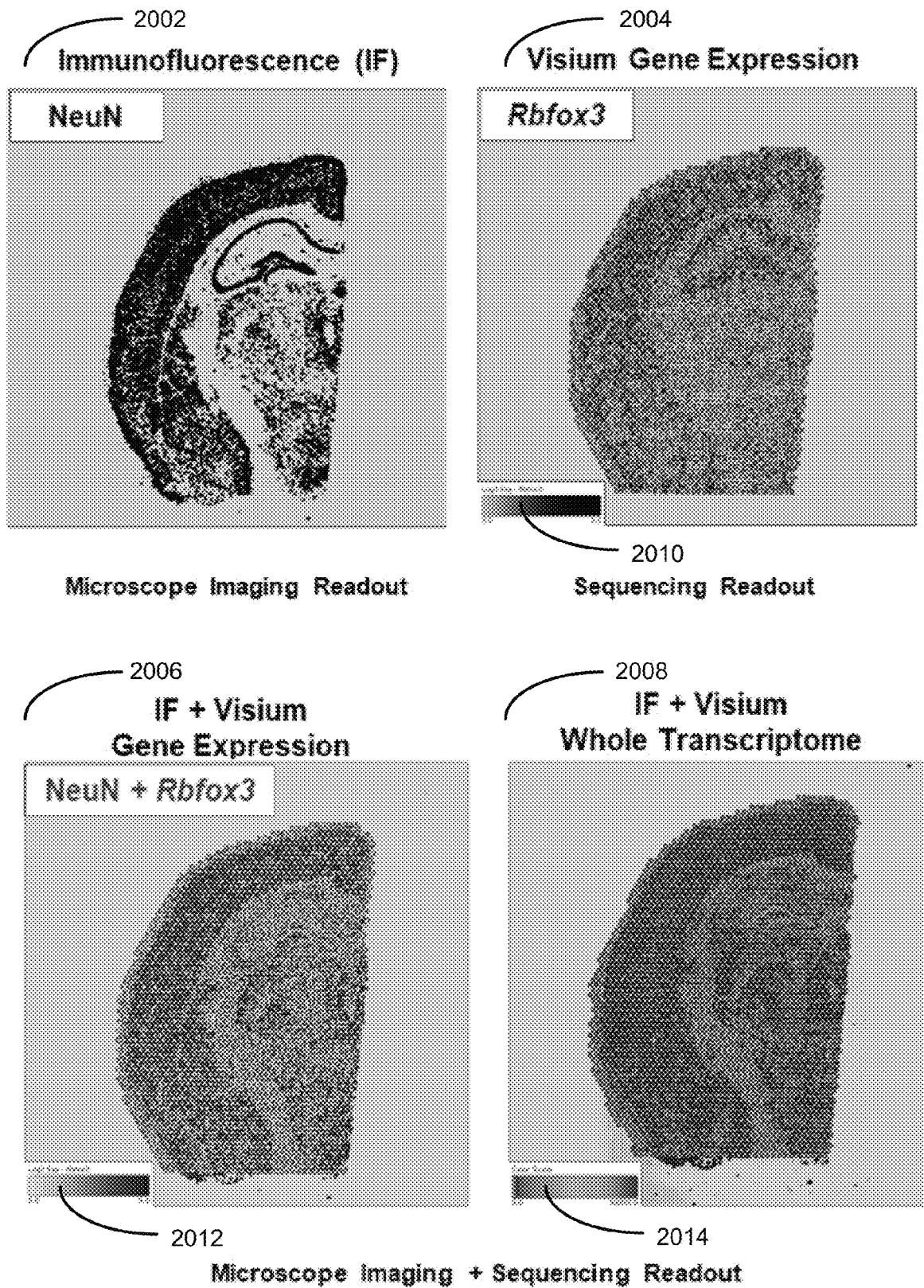
FIG. 20 illustrates an immunofluorescence image, a representation of all or a portion of each subset of sequence reads at each respective position within one or more images that maps to a respective capture spot corresponding to the respective position, as well as composite representations in accordance with embodiments of the present disclosure.

FIG. 20 illustrates an embodiment of the present disclosure in which a biological sample has an image 2002 that has been collected by immunofluoresence. Moreover, the sequence reads of the biological sample have been spatially resolved using the methods disclosed herein. More specifically, a plurality of spatial barcodes has been used to localize respective sequence reads in a plurality of sequence reads obtained from the biological sample (using the methods disclosed herein) to corresponding capture spots in a set of capture spots (through their spatial barcodes), thereby dividing the plurality of sequence reads into a plurality of subsets of sequence reads, each respective subset of sequence reads corresponding to a different capture spot (through their spatial barcodes) in the plurality of capture spots. As such, panel 2004 shows a representation of a portion (that portion that maps to the gene Rbfox3) of each subset of sequence reads at each respective position within image 2002 that maps to a respective capture spot corresponding to the respective position. Panel 2006 of FIG. 20 shows a composite representation comprising (i) the image 2002 and (ii) a representation of a portion (that portion that maps to the gene Rbfox3) of each subset of sequence reads at each respective position within image 2002 that maps to a respective capture spot corresponding to the respective position. Finally, panel 2008 of FIG. 20 shows a composite representation comprising (i) the image 2002 and (ii) a whole transcriptome representation of each subset of sequence reads at each respective position within image 2002 that maps to a respective capture spot corresponding to the respective position. In panels 2004, 2006, and 2008, each representation of sequence reads in each subset represents a number of unique UMI, on a capture spot by capture spot basis, in the subsets of sequence reads on a color scale basis as outlined by respective scales 2010, 2012, and 2014. While panel 2008 shows mRNA-based UMI abundance overlayed on a source images, the present disclosure can also be used to illustrate the spatial quantification of other analytes such as proteins, either superimposed on images of their source tissue or arranged in two-dimensional space using dimension reduction algorithms such as t-SNE or UMAP, including cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). For general disclosure on how ATAC is spatially quantified using, for example clustering and/or t-SNE (where such cluster and/or t-SNE plots can be displayed in linked windows), see, United States Publication No. US-2020105373-A1 entitled "Systems and Methods for Cellular Analysis Using Nucleic Acid Sequencing" which is hereby incorporated by reference. For general disclosure on how V(D)J sequences are spatially quantified using, for example clustering and/or t-SNE (where such cluster and/or t-SNE plots can be displayed in linked windows), see, U.S. patent application Ser. No. 15/984,324, entitled "Systems and Methods for Clonotype Screening," filed May 19, 2018, which is hereby incorporated by reference.

Example 5—Differential Values

In some embodiments, the techniques of this Example 5 are run on any of the discrete attribute value datasets of the present disclosure.

Once each probe spot 126 has been assigned to a respective cluster 158, the systems and methods of the present disclosure are able to compute, for each respective locus 122 in the plurality of loci for each respective cluster 158 in the plurality of clusters, a difference in the discrete attribute value 124 for the respective locus 122 across the respective subset of probe spots 126 in the respective cluster 158 relative to the discrete attribute value 124 for the respective locus 122 across the plurality of clusters 158 other than the respective cluster, thereby deriving a differential value 162 for each respective locus 122 in the plurality of loci for each cluster 158 in the plurality of clusters. For instance, in some such embodiments, a differential expression algorithm is invoked to find the top expressing genes that are different between probe spot classes or other forms of probe spot labels. This is a form of the general differential expressional problem in which there is one set of expression data and another set of expression data and the question to be addressed is determining which genes are differentially expressed between the datasets.

In some embodiments, differential expression is computed as the $\log_2$ fold change in (i) the average number of transcripts (discrete attribute value 124 for locus 122) measured in each of the probe spots 126 of the subject cluster 158 that map to a particular gene (locus 122) and (ii) the average number of transcripts measured in each of the probe spots of all clusters other than the subject cluster that map to the particular gene. Thus, consider the case in which the subject cluster contains 50 probe spots and on average each of the 50 probe spots contain 100 transcripts for gene A. The remaining clusters collectively contain 250 probe spots and, on average, each of the 250 probe spots contains 50 transcripts for gene A. Here, the fold change in expression for gene A is 100/50 and the $\log_2$ fold change is $\log_2(100/50)=1$. In FIG. 4, lower panel, the $\log_2$ fold change is computed in this manner for each gene in the human genome.

In some embodiments, the differential value 162 for each respective locus 122 in the plurality of loci for each respective cluster 158 in the plurality of clusters is a fold change in (i) a first measure of central tendency of the discrete attribute value 124 for the locus measured in each of the probe spots 126 in the plurality of probe spots in the respective cluster 158 and (ii) a second measure of central tendency of the discrete attribute value 124 for the respective locus 122 measured in each of the probe spots 126 of all clusters 158 other than the respective cluster. In some embodiments, the first measure of central tendency is an arithmetic mean, weighted mean, midrange, midhinge, trimean, Winsorized mean, median, or mode of all the discrete attribute value 124 for the locus measured in each of the probe spots 126 in the plurality of probe spots in the respective cluster 158. In some embodiments, the second measure of central tendency is an arithmetic mean, weighted mean, midrange, midhinge, trimean, Winsorized mean, median, or mode of all the discrete attribute value 124 for the locus 122 measured in each of the probe spots 126 in the plurality of probe spots 126 in all clusters other than the respective cluster. Referring to block 222, in some embodiments, the fold change is a $\log_2$ fold change. Referring to block 224, in some embodiments, the fold change is a $\log_{10}$ fold change.

Given that measurement of discrete attribute values 124 for loci 122 (e.g., count of mRNA that maps to a given gene in a given probe spot) is typically noisy, the variance of the discrete attribute values 124 for loci 122 in each probe spot 126 (e.g., count of mRNA that maps to given gene in a given probe spot) in a given cluster 158 of such probe spots 126 is taken into account in some embodiments. This is analogous to the t-test, which is a statistical way to measure the difference between two samples. Here, in some embodiments, statistical methods that take into account that a discrete number of loci 122 are being measured (as the discrete attribute values 124 for a given locus 122) for each probe spot 126 and that model the variance that is inherent in the system from which the measurements are made are implemented.

Thus, in some embodiments, each discrete attribute value 124 is normalized prior to computing the differential value 162 for each respective locus 122 in the plurality of loci for each respective cluster 158 in the plurality of clusters. Referring to block 228 of FIG. 2B, in some embodiments, the normalizing comprises modeling the discrete attribute value 124 of each locus associated with each probe spot in the plurality of probe spots with a negative binomial distribution having a consensus estimate of dispersion without loading the entire dataset into non-persistent memory 111. Such embodiments are useful, for example, for RNA-seq experiments that produce discrete attribute values 124 for loci 122 (e.g., digital counts of mRNA reads that are affected by both biological and technical variation). To distinguish the systematic changes in expression between conditions from noise, the counts are frequently modeled by the Negative Binomial distribution. See Yu, 2013, "Shrinkage estimation of dispersion in Negative Binomial models for RNA-seq experiments with small sample size," Bioinformatics 29, pp. 1275-1282, which is hereby incorporated by reference.

The negative binomial distribution for a discrete attribute value 124 for a given locus 122 includes a dispersion parameter for the discrete attribute value 124, which tracks the extent to which the variance in the discrete attribute value 124 exceeds an expected value. See Yu, 2013, "Shrinkage estimation of dispersion in Negative Binomial models for RNA-seq experiments with small sample size," Bioinformatics 29, pp. 1275-1282, and Cameron and Trivedi, 1998, "Regression Analysis of Count Data," Econometric Society Monograph 30, Cambridge University Press, Cambridge, UK, each of which is hereby incorporated by reference. Rather than relying upon an independent dispersion parameter for the discrete attribute value 124 of each locus 122, some embodiments of the disclosed systems and methods advantageously use a consensus estimate across the discrete attribute values 124 of all the loci 122. This is termed herein the "consensus estimate of dispersion." The consensus estimate of dispersion is advantageous for RNA-seq experiments in which whole transcriptome sequencing (RNA-seq) technology quantifies gene expression in biological samples in counts of transcript reads mapped to the genes, which is one form of experiment used to acquire the disclosed discrete attribute values 124 in some embodiments, thereby concurrently quantifying the expression of many genes. The genes share aspects of biological and technical variation, and therefore a combination of the gene-specific estimates and of consensus estimates can yield better estimates of variation. See Yu, 2013, "Shrinkage estimation of dispersion in Negative Binomial models for RNA-seq experiments with small sample size," Bioinformatics 29, pp. 1275-1282 and Anders and Huber, 2010, "Differential expression analysis for sequence count data," Genome Biol 11, R106, each of which are hereby incorporated by reference. For instance, in some such embodiments, sSeq is applied to the discrete attribute value 124 of each locus 122. sSeq is disclosed in Yu, 2013, "Shrinkage estimation of dispersion in Negative Binomial models for RNA-seq experiments with small sample size," Bioinformatics 29, pp. 1275-1282, which is hereby incorporated by reference. sSeq scales very well with the number of genes that are being compared. In typical experiments in accordance with the present disclosure, each cluster 158 may include hundreds, thousands, tens of thousands, hundreds of thousands, or more probe spots 126, and each respective probe spot 126 may contain mRNA expression data for hundreds, or thousands of different genes. As such, sSeq is particularly advantageous when testing for differential expression in such large discrete attribute value datasets 120. Of all the RNA-seq methods, sSeq is advantageously faster. Other single-probe spot differential expression methods exist and can be used in some embodiments, but they are designed for smaller-scale experiments. As such sSeq, and more generally techniques that normalize discrete attribute values by modeling the discrete attribute value 124 of each locus 122 associated with each probe spot 126 in the plurality of probe spots with a negative binomial distribution having a consensus estimate of dispersion without loading the entire discrete attribute value dataset 120 into non-persistent memory 111, are practiced in some embodiments, of the present disclosure. In some embodiments, in the case where parameters for the sSeq calculations are calculated, the discrete attribute values for each of the loci is examined in order to get a dispersion value for all the loci. Here, although all the discrete attribute values for the loci are accessed to make the calculation, the discrete attribute values are not all read from persistent memory 112 at the same time. In some embodiments, discrete attribute values are obtained by traversing through blocks of compressed data, a few blocks at a time. That is, a set of blocks (e.g., consisting of the few compressed blocks) in the dataset are loaded into non-persistent memory from persistent memory and are analyzed to determine which loci the set of blocks represent. An array of discrete attribute values across the plurality of probe spots, for each of the loci encoded in the set of blocks, is determined and used calculate the variance, or other needed parameters, for these loci across the plurality of probe spots. This process is repeated in which new set of blocks is loaded into non-persistent memory from persistent memory, analyzed to determine which loci are encoded in the new set of blocks, and then used to compute the variance, or other needed parameters, for these loci across the plurality of probe spots for each of the loci encoded in the new set of blocks, before discarding the set of blocks from non-persistent memory. In this way, only a limited amount of the discrete attribute value dataset 120 is stored in non-persistent memory 111 at any given time (e.g., the data for a particular block that contain the discrete attribute values for a particular locus). Further, the systems and methods of the present disclosure are able to compute variance in discrete attribute values for a given locus because it has got stored the discrete attribute values for that particular locus across one or more images and/or one or more spatial projections 121 of the discrete attribute value dataset 120 stored in a single bgzf block, in some embodiments. Once the variance, or other needed parameter is computed for the loci (or discrete attribute values of the loci), the accessed set of bgzf blocks (which is a subset of the total number of bgzf blocks in the dataset), which had been loaded into non-persistent memory 111 to perform the computation, is dropped from non-persistent memory and another set of bgzf blocks for which such computations is to be performed is loaded into the non-persistent memory 111 from the persistent memory 112. In some embodiments, such processes run in parallel (e.g., one process for each locus) when there are multiple processing cores 102. That is, each processing core concurrently analyzes a different respective set of blocks in the dataset and computes loci statistics for those loci represented in the respective set of blocks.

Following such normalization, in some embodiments, for each respective locus 122, an average (or some other measure of central tendency) discrete attribute value 124 (e.g., count of the locus 122) for each locus 122 is calculated for each cluster 158 of probe spots 126. Thus, in the case where there is a first and second cluster 158 of probe spots 126, the average (or some other measure of central tendency) discrete attribute value 124 of the locus A across all the probe spots 126 of the first cluster 158, and the average (or some other measure of central tendency) discrete attribute value 124 of locus A across all the probe spots 126 of the second cluster 158 is calculated and, from this, the differential value 162 for each the locus with respect to the first cluster is calculated. This is repeated for each of the loci 122 in a given cluster. It is further repeated for each cluster 158 in the plurality of clusters. In some embodiments, there are other factors that are considered, like adjusting the initial estimate of the variance in the discrete attribute value 124 when the data proves to be noisy. In the case where there are more than two clusters, the average (or some other measure of central tendency) discrete attribute value 124 of the locus A across all the probe spots 126 of the first cluster 158 and the average (or some other measure of central tendency) discrete attribute value 124 of locus A across all the probe spots 126 of the remaining cluster 158, is calculated and used to compute the differential value 162.

Example 6—Display a Heat Map

In some embodiments, the techniques of this Example 6 are run on any of the discrete attribute value datasets of the present disclosure.

With reference to FIG. 4, once the differential value 162 for each respective locus 122 in the plurality of loci for each respective cluster 158 in the plurality of clusters has been computed in accordance with Example 5, a heat map 402 of these differential values is displayed in a first panel 404 of an interface 400. The heat map 402 comprises a representation of the differential value 162 for each respective locus 122 in the plurality of loci for each cluster 158 in the plurality of clusters. As illustrated in FIG. 4, the differential value 162 for each locus 122 in the plurality of probe spots (e.g., loci from 122-1 to 122-M) for each cluster 158 (e.g., clusters 158-1, and 158-11) is illustrated in a color coded way to represent the $\log_2$ fold change in accordance with color key 408. In accordance with color key 408, those loci 122 that are upregulated in the probe spots of a particular cluster 158 relative to all other clusters are assigned more positive values, whereas those loci 122 that are downregulated in the probe spots of a particular cluster 158 relative to all other clusters are assigned more negative values. In some embodiments, the heat map can be exported to persistent storage (e.g., as a PNG graphic, JPG graphic, or other file formats).

Example 7—Two Dimensional Plot of the Probe Spots in the Dataset

In some embodiments, the techniques of this Example 7 are run on any of the discrete attribute value datasets of the present disclosure.

With reference to FIG. 4, in some embodiments, a two-dimensional visualization of the discrete attribute value dataset 120 is also provided in a second panel 420. In some embodiments, the two-dimensional visualization in the second panel 420 is computed by a back end pipeline that is remote from visualization system 100 and is stored as two-dimensional data points 166 in the discrete attribute value dataset 120 as illustrated in FIG. 1B. In some embodiments, the two-dimensional visualization 420 is computed by the visualization system.

Because the initial data is sparse, in some embodiments, the two-dimensional visualization is prepared by computing a corresponding plurality of principal component values 164 for each respective probe spot 126 in the plurality of probe spots based upon respective values of the discrete attribute value 124 for each locus 122 in the respective probe spot 126. In some embodiments, the plurality of principal component values is ten. In some embodiments, the plurality of principal component values is between 5 and 100. In some embodiments, the plurality of principal component values is between 5 and 50. In some embodiments, the plurality of principal component values is between 8 and 35. In some embodiments, a dimension reduction technique is then applied to the plurality of principal components values for each respective probe spot 126 in the plurality of probe spots, thereby determining a two-dimensional data point 166 for each probe spot 126 in the plurality of probe spots. Each respective probe spot 126 in the plurality of probe spots is then plotted in the second panel based upon the two-dimensional data point for the respective probe spot.

For instance, one embodiment of the present disclosure provides a back end pipeline that is performed on a computer system other than the visualization system 100. The back end pipeline comprises a two stage data reduction. In the first stage, the discrete attribute values 124 (e.g., mRNA expression data) for each locus 122 in a probe spot 126 is treated as a high-dimensional data point. For instance, the data point is, in some embodiments, a one-dimensional vector that includes a dimension for each of the 19,000-20,000 genes in the human genome, with each dimension populated with the measured mRNA expression level for the corresponding gene. More generally, a one-dimensional vector includes a dimension for each discrete attribute value 124 of the plurality of loci, with each dimension populated with the discrete attribute value 124 for the corresponding locus 122. This data is considered somewhat sparse and so principal component analysis is suitable for reducing the dimensionality of the data down to ten dimensions in this example. In some embodiments, application of principal component analysis can drastically reduce (reduce by at least 5-fold, at least 10-fold, at least 20-fold, or at least 40-fold) the dimensionality of the data (e.g., from approximately 20,000 to ten dimensions). That is, principal component analysis is used to assign each respective probe spot those principal components that describe the variation in the respective probe spot's mRNA expression levels with respect to expression levels of corresponding mRNA of other probe spots in the dataset. Next, the data reduction technique t-Distributed Stochastic Neighboring Entities (t-SNE) is used to further reduce the dimensionality of the data from ten to two. See, block 236 of FIG. 2C. t-SNE is a machine learning algorithm that is used for dimensionality reduction. See van der Maaten and Hinton, 2008, "Visualizing High-Dimensional Data Using t-SNE," Journal of Machine Learning Research 9, 2579-2605, which is hereby incorporated by reference. The nonlinear dimensionality reduction technique t-SNE is particularly well-suited for embedding high-dimensional data (here, the ten principal components values 164) computed for each measured probe spot based upon the measured discrete attribute value (e.g., expression level) of each locus 122 (e.g., expressed mRNA) in a respective probe spot as determined by principal component analysis into a space of two, which can then be visualized as a two-dimensional visualization (e.g., the scatter plot of second panel 420). In some embodiments, t-SNE is used to model each high-dimensional object (the 10 principal components of each measured probe spot) as a two-dimensional point in such a way that similarly expressing probe spots are modeled as nearby two-dimensional data points 166 and dissimilarly expressing probe spots are modeled as distant two-dimensional data points 166 in the two-dimensional plot. The t-SNE algorithm comprises two main stages. First, t-SNE constructs a probability distribution over pairs of high-dimensional probe spot vectors in such a way that similar probe spot vectors (probe spots that have similar values for their ten principal components and thus presumably have similar discrete attribute values 124 across the plurality of loci 122) have a high probability of being picked, while dissimilarly dissimilar probe spot vectors (probe spots that have dissimilar values for their ten principal components and thus presumably have dissimilar discrete attribute values 124 across the plurality of loci 122) have a small probability of being picked. Second, t-SNE defines a similar probability distribution over the plurality of probe spots 126 in the low-dimensional map, and it minimizes the Kullback-Leibler divergence between the two distributions with respect to the locations of the points in the map. In some embodiments, the t-SNE algorithm uses the Euclidean distance between objects as the base of its similarity metric. In other embodiments, other distance metrics are used (e.g., Chebyshev distance, Mahalanobis distance, Manhattan distance, etc.).

In some embodiments, referring to block 238 of FIG. 2C, rather than using t-SNE, the dimension reduction technique used to reduce the principal component values 164 to a two-dimensional data point 166 is Sammon mapping, curvilinear components analysis, stochastic neighbor embedding, Isomap, maximum variance unfolding, locally linear embedding, or Laplacian Eigenmaps. These techniques are described in van der Maaten and Hinton, 2008, "Visualizing High-Dimensional Data Using t-SNE," Journal of Machine Learning Research 9, 2579-2605, which is hereby incorporated by reference. In some embodiments, the user has the option to select the dimension reduction technique. In some embodiments, the user has the option to select the dimension reduction technique from a group comprising all or a subset of the group consisting of t-SNE, Sammon mapping, curvilinear components analysis, stochastic neighbor embedding, Isomap, maximum variance unfolding, locally linear embedding, and Laplacian Eigenmaps.

CONCLUSION

The information types described above are presented on a user interface of a computing device in an interactive manner, such that the user interface can receive user input instructing the user interface to modify representation of the information. Various combinations of information can be displayed concurrently in response to user input. Using the information visualization methods described herein, previously unknown patterns and relationships can be discovered from discrete attribute value datasets. In this way, biological samples can be characterized.

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A computer system comprising one or more processing cores, a memory, and a display, wherein the memory stores instructions for performing a method for identifying a morphological pattern, the method comprising:
   A) obtaining a discrete attribute value dataset associated with a plurality of probe spots having a spatial arrangement, the discrete attribute value dataset comprising:
      (i) one or more spatial projections of a biological sample,
      (ii) one or more two-dimensional images, for a first spatial projection in the one or more spatial projections, wherein each respective two-dimensional image in the one or more two-dimensional images (a) is taken of a corresponding first tissue section, obtained from the biological sample, overlaid on a substrate having the plurality of probe spots arranged in the spatial arrangement, and
      (iii) a corresponding plurality of discrete attribute values for each respective probe spot in the plurality of probe spots obtained from two-dimensional spatial sequencing of the first tissue section, wherein each respective discrete attribute value in the corresponding plurality of discrete attribute values is for a locus in a plurality of loci and each corresponding plurality of discrete attribute values comprises at least 500 discrete attribute values;
   B) obtaining a corresponding cluster assignment in a plurality of clusters, of each respective probe spot in at least a subset of the plurality of probe spots of the discrete attribute value dataset, wherein the corresponding cluster assignment is based, at least in part, on the corresponding plurality of discrete attribute values of the respective probe spot, or a corresponding plurality of dimension reduction components derived, at least in part, from the corresponding plurality of discrete attribute values of the respective probe spot;
   C) displaying, on the display, pixel values of all or portion of a first two-dimensional image in the one or more two-dimensional images of the first spatial projection; and
   D) overlaying on the first two-dimensional image first indicia for one or more probe spots in the plurality of probe spots that have been assigned to a first cluster in the plurality of clusters, thereby identifying the morphological pattern.

2. The computer system of claim 1, wherein:
   the one or more spatial projections is a plurality of spatial projections of the biological sample,
   the plurality of spatial projections comprises the first spatial projection for a first tissue section of the biological sample, and
   the plurality of spatial projections comprises a second spatial projection for a second tissue section of the biological sample.

3. The computer system of claim 2, wherein:
   the one or more two-dimensional images for the first spatial projection comprises a first plurality of two-dimensional images, and
   the second spatial projection comprises a second plurality of two-dimensional images.

4. The computer system of claim 3, wherein:
   each two-dimensional image in the first plurality of two-dimensional images is taken of the first tissue section of the biological sample, and
   each two-dimensional image in the second plurality of two-dimensional images is taken of a second tissue section of the biological sample.

5. The computer system of claim 3, wherein each two-dimensional image of the first plurality of two-dimensional images is displayed, co-aligned with the first indicia for each probe spot in the plurality of probe spots that have been assigned to the first cluster.

6. The computer system of claim 5, the method further comprising, responsive to receiving user display instructions, displaying or removing from display one or more two-dimensional images in the first plurality of two-dimensional images.

7. The computer system of claim 3, wherein each respective two-dimensional image in the first plurality of two-dimensional images is acquired from the first tissue section using a different wavelength or different wavelength band.

8. The computer system of claim 1, wherein:
   the one or more spatial projections is a single spatial projection,
   the one or more two-dimensional images of the first spatial projection is a plurality of two-dimensional images,
   a first two-dimensional image in the plurality of two-dimensional images is a bright-field image of the first tissue section,
   a second two-dimensional image in the plurality of two-dimensional images is a first immunohistochemistry (IHC) image of the first tissue section taken at a first wavelength or a first wavelength range, and
   a third two-dimensional image in the plurality of two-dimensional images is a second immunohistochemistry (IHC) image of the first tissue section taken at a second wavelength or a second wavelength range that is different than the first wavelength or the first wavelength range.

9. The computer system of claim 8, wherein:
   the first two-dimensional image is acquired using Haemotoxylin and Eosin, a Periodic acid-Schiff reaction stain, a Masson's trichrome stain, an Alcian blue stain, a van Gieson stain, a reticulin stain, an Azan stain, a Giemsa stain, a Toluidine blue stain, an isamin blue/eosin stain, a Nissl and methylene blue stain, a sudan black and/or osmium staining of the biological sample.

10. The computer system of claim 1, the method further comprising:
storing the first two-dimensional image in a first schema, wherein the first schema comprises a first number of tiles; and
storing the first two-dimensional image in a second schema, wherein the second schema comprises a second number of tiles, wherein the second number of tiles is less than the first number of tiles.

11. The computer system of claim 10, the method further comprising, responsive to receiving display instructions for a user:
switching from the first schema to the second schema in order to display all or a portion of the first two-dimensional image, or
switching from the second schema to the first schema in order to display all or a portion of the first two-dimensional image.

12. The computer system of claim 10, wherein:
at least a first tile in the first number of tiles comprises a first predetermined tile size,
at least a second tile in the first number of tiles comprises a second predetermined tile size, and
at least a first tile in the second number of tiles comprises of a third predetermined tile size.

13. The computer system of claim 1, wherein the obtaining B) comprises clustering at least the subset of the plurality of probe spots across the one or more spatial projections using the discrete attribute values assigned to each respective probe spot, in at least the subset of the plurality of probe spots, in each of the one or more spatial projections as a multi-dimensional vector, wherein the clustering is configured to load less than the entirety of the discrete attribute value dataset into a non-persistent memory during the clustering thereby allowing the clustering of the discrete attribute value dataset having a size that exceeds storage space in a non-persistent memory allocated to the discrete attribute value dataset.

14. The computer system of claim 1, wherein each respective cluster in the plurality of clusters consists of a unique subset of the plurality of probe spots.

15. The computer system of claim 1, wherein:
each locus in the plurality of loci is a respective gene in a plurality of genes, and
each discrete attribute value in the corresponding plurality of discrete attribute values is a count of unique molecular identifiers that map to a corresponding probe spot and that also map to a respective gene in the plurality of genes.

16. The computer system of claim 15, wherein the discrete attribute value dataset represents a whole transcriptome sequencing experiment that quantifies gene expression in counts of transcript reads mapped to the plurality of genes or the discrete attribute value dataset represents a targeted transcriptome sequencing experiment that quantifies gene expression in unique molecular identifier counts mapped to probes in the plurality of probes.

17. The computer system of claim 1, wherein the first indicia is a first graphic or a first color.

18. The computer system of claim 1, wherein:
each locus in the plurality of loci is a respective feature in a plurality of features,
each discrete attribute value in the corresponding plurality of discrete attribute values is a count of unique molecular identifiers that map to a corresponding probe spot and that also map to a respective feature in the plurality of features, and
each feature in the plurality of features is an open-reading frame, an intron, an exon, an entire gene, an RNA transcript, a predetermined non-coding part of a reference genome, an enhancer, a repressor, a predetermined sequence encoding a variant allele, or any combination thereof.

19. The computer system of claim 1, wherein each probe spot in the plurality of probe spots is assigned a unique barcode in a plurality of barcodes.

20. The computer system of claim 1, wherein the plurality of probe spots comprises at least 1000 probe spots.

21. The computer system of claim 1, wherein each respective two-dimensional image in the one or more two-dimensional images comprises at least 100,000 pixel values.

22. The computer system of claim 1, wherein the overlaying D) (i) co-aligns the first indicia for the one or more probe spots in the plurality of probe spots that have been assigned to a first cluster in the plurality of clusters with the first two-dimensional image, and (ii) further comprises overlaying, on the first two-dimensional image, second indicia for each probe spot in the plurality of probe spots that have been assigned to a second cluster in the plurality of clusters.

23. The computer system of claim 1, wherein each respective probe spot in the plurality of probe spots has a center to center distance to a neighboring probe spot in the plurality of probe spots of 100 μM or less.

24. The computer system of claim 1, the method further comprising, for each respective probe spot overlayed on the first two-dimensional image, displaying a corresponding discrete attribute value, associated with the respective probe spot, for a first locus in the plurality of loci.

25. The computer system of claim 24, wherein the corresponding discrete attribute value is a unique molecular identifier count indicating a number of copies of a product of the first locus that were detected in the respective probe spot.

26. The computer system of claim 24, wherein the corresponding discrete attribute value is displayed in color coded log-space in accordance with a log-space heat map scale.

27. A non-transitory computer-readable medium storing one or more computer programs executable by a computer for identifying a morphological pattern, the computer comprising a memory, the one or more computer programs collectively encoding computer executable instructions for performing a method comprising:
A) obtaining a discrete attribute value dataset associated with a plurality of probe spots having a spatial arrangement, the discrete attribute value dataset comprising:
(i) one or more spatial projections of a biological sample,
(ii) one or more two-dimensional images, for a first spatial projection in the one or more spatial projections, wherein each respective two-dimensional image in the one or more two-dimensional images (a) is taken of a corresponding first tissue section, obtained from the biological sample, overlaid on a substrate having the plurality of probe spots arranged in the spatial arrangement, and
(iii) a corresponding plurality of discrete attribute values for each respective probe spot in the plurality of probe spots obtained from two-dimensional spatial sequencing of the first tissue section, wherein each respective discrete attribute value in the corresponding plurality of discrete attribute values is for a locus in a plurality of loci and each corresponding plurality of discrete attribute values comprises at least 500 discrete attribute values;

B) obtaining a corresponding cluster assignment in a plurality of clusters, of each respective probe spot in at least a subset of the plurality of probe spots of the discrete attribute value dataset, wherein the corresponding cluster assignment is based, at least in part, on the corresponding plurality of discrete attribute values of the respective probe spot, or a corresponding plurality of dimension reduction components derived, at least in part, from the corresponding plurality of discrete attribute values of the respective probe spot;

C) displaying, on the display, pixel values of all or portion of a first two-dimensional image in the one or more two-dimensional images of the first spatial projection; and D) overlaying on the first two-dimensional image first indicia for one or more probe spots in the plurality of probe spots that have been assigned to a first cluster in the plurality of clusters, thereby identifying the morphological pattern.

28. The non-transitory computer-readable medium of claim 27, wherein each probe spot in the plurality of probe spots is assigned a unique barcode in a plurality of barcodes.

29. The non-transitory computer-readable medium of claim 27, wherein the plurality of probe spots comprises at least 1000 probe spots.

30. The non-transitory computer-readable medium of claim 27, wherein each respective two-dimensional image in the one or more two-dimensional images comprises at least 100,000 pixel values.

31. The non-transitory computer-readable medium of claim 27, wherein the overlaying D) (i) co-aligns the first indicia for the one or more probe spots in the plurality of probe spots that have been assigned to a first cluster in the plurality of clusters with the first two-dimensional image, and (ii) further comprises overlaying, on the first two-dimensional image, second indicia for each probe spot in the plurality of probe spots that have been assigned to a second cluster in the plurality of clusters.

32. The non-transitory computer-readable medium of claim 27, wherein each respective probe spot in the plurality of probe spots has a center to center distance to a neighboring probe spot in the plurality of probe spots of 100 μM or less.

33. The non-transitory computer-readable medium of claim 27, the method further comprising, for each respective probe spot overlayed on the first two-dimensional image, displaying a corresponding discrete attribute value, associated with the respective probe spot, for a first locus in the plurality of loci, wherein:

the corresponding discrete attribute value (i) is a unique molecular identifier count indicating a number of copies of a product of the first locus that were detected in the respective probe spot or (ii) is displayed in color coded log-space in accordance with a log-space heat map scale.

34. A method for identifying a morphological pattern, the method comprising:

at a computer system comprising one or more processing cores, a memory, and a display:

A) obtaining a discrete attribute value dataset associated with a plurality of probe spots having a spatial arrangement, the discrete attribute value dataset comprising:
(i) one or more spatial projections of a biological sample,
(ii) one or more two-dimensional images, for a first spatial projection in the one or more spatial projections, wherein each respective two-dimensional image in the one or more two-dimensional images (a) is taken of a corresponding first tissue section, obtained from the biological sample, overlaid on a substrate having the plurality of probe spots arranged in the spatial arrangement, and
(iii) a corresponding plurality of discrete attribute values for each respective probe spot in the plurality of probe spots obtained from two-dimensional spatial sequencing of the first tissue section, wherein each respective discrete attribute value in the corresponding plurality of discrete attribute values is for a locus in a plurality of loci and each corresponding plurality of discrete attribute values comprises at least 500 discrete attribute values;

B) obtaining a corresponding cluster assignment in a plurality of clusters, of each respective probe spot in at least a subset of the plurality of probe spots of the discrete attribute value dataset, wherein the corresponding cluster assignment is based, at least in part, on the corresponding plurality of discrete attribute values of the respective probe spot, or a corresponding plurality of dimension reduction components derived, at least in part, from the corresponding plurality of discrete attribute values of the respective probe spot;

C) displaying, on the display, pixel values of all or portion of a first two-dimensional image in the one or more two-dimensional images of the first spatial projection; and D) overlaying on the first two-dimensional image first indicia for one or more probe spots in the plurality of probe spots that have been assigned to a first cluster in the plurality of clusters, thereby identifying the morphological pattern.

35. The method of claim 34, wherein each probe spot in the plurality of probe spots is assigned a unique barcode in a plurality of barcodes.

36. The method of claim 34, wherein the plurality of probe spots comprises at least 1000 probe spots.

37. The method of claim 34, wherein each respective two-dimensional image in the one or more two-dimensional images comprises at least 100,000 pixel values.

38. The method of claim 34, wherein the overlaying D) (i) co-aligns the first indicia for the one or more probe spots in the plurality of probe spots that have been assigned to a first cluster in the plurality of clusters with the first two-dimensional image, and (ii) further comprises overlaying, on the first two-dimensional image, second indicia for each probe spot in the plurality of probe spots that have been assigned to a second cluster in the plurality of clusters.

39. The method of claim 34, wherein each respective probe spot in the plurality of probe spots has a center to center distance to a neighboring probe spot in the plurality of probe spots of 100 μM or less.

40. The method of claim 34, the method further comprising, for each respective probe spot overlayed on the first two-dimensional image, displaying a corresponding discrete attribute value, associated with the respective probe spot, for a first locus in the plurality of loci, wherein:

the corresponding discrete attribute value (i) is a unique molecular identifier count indicating a number of copies of a product of the first locus that were detected in the respective probe spot or (ii) is displayed in color coded log-space in accordance with a log-space heat map scale.

* * * * *